United States Patent
Wu et al.

(10) Patent No.: US 10,483,468 B2
(45) Date of Patent: Nov. 19, 2019

(54) COMPOUND AND ORGANIC ELECTRONIC DEVICE USING THE SAME

(71) Applicant: NICHEM FINE TECHNOLOGY CO., LTD., Jhubei, Hsinchu County (TW)

(72) Inventors: Hui-Ling Wu, Jhubei (TW); Liang-Di Liao, Jhubei (TW); Shwu-Ju Shieh, Jhubei (TW); Chi-Chung Chen, Jhubei (TW)

(73) Assignee: SHANGHAI NICHEM FINE CHEMICAL CO., LTD., Shanghai (CN)

(*) Notice: Subject to any disclaimer, the term of this patent is extended or adjusted under 35 U.S.C. 154(b) by 236 days.

(21) Appl. No.: 15/829,033

(22) Filed: Dec. 1, 2017

(65) Prior Publication Data

US 2018/0159045 A1 Jun. 7, 2018

Related U.S. Application Data

(60) Provisional application No. 62/430,982, filed on Dec. 7, 2016, provisional application No. 62/433,371, filed on Dec. 13, 2016.

(51) Int. Cl.
*H01L 51/50* (2006.01)
*H01L 51/00* (2006.01)
(Continued)

(52) U.S. Cl.
CPC ........ *H01L 51/0058* (2013.01); *C07D 311/82* (2013.01); *C07D 335/12* (2013.01);
(Continued)

(58) Field of Classification Search
None
See application file for complete search history.

(56) References Cited

FOREIGN PATENT DOCUMENTS

| CN | 105778891 A | | 7/2016 | |
|---|---|---|---|---|
| JP | 2009-057300 | * | 3/2009 | .......... C07D 311/94 |
| WO | WO 2016/087017 A1 | | 6/2016 | |

* cited by examiner

*Primary Examiner* — Gregory D Clark
(74) *Attorney, Agent, or Firm* — Birch, Stewart, Kolasch & Birch, LLP

(57) ABSTRACT

Provided are a novel compound and an organic electronic device using the same. The novel compound is represented by the following Formula (I):

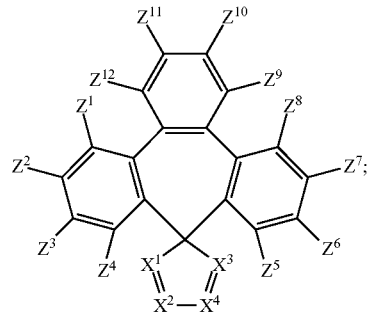

Formula (I)

wherein $X^1$ and $X^2$ are each independently $C(R^3)$, the two $(R^3)$s are the same or different, and the two $(R^3)$s are joined together to form a first aryl ring; $X^3$ and $X^4$ are each independently $C(R^b)$, the two $(R^b)$s are the same or different, the two $(R^b)$s are joined to form a second aryl ring, and the second aryl ring is a polycyclic aromatic ring.

18 Claims, 13 Drawing Sheets

(51) Int. Cl.
*C07D 311/82* (2006.01)
*C07D 335/12* (2006.01)
*C07D 405/04* (2006.01)
*C07D 405/14* (2006.01)
*C07D 409/04* (2006.01)
*C07D 409/14* (2006.01)
*C09K 11/06* (2006.01)
*G01R 33/46* (2006.01)

(52) U.S. Cl.
CPC ......... *C07D 405/04* (2013.01); *C07D 405/14* (2013.01); *C07D 409/04* (2013.01); *C07D 409/14* (2013.01); *C09K 11/06* (2013.01); *H01L 51/0054* (2013.01); *H01L 51/0057* (2013.01); *H01L 51/0067* (2013.01); *H01L 51/0068* (2013.01); *H01L 51/0071* (2013.01); *H01L 51/0072* (2013.01); *H01L 51/0073* (2013.01); *H01L 51/0074* (2013.01); *H01L 51/5072* (2013.01); *C09K 2211/1088* (2013.01); *C09K 2211/1092* (2013.01); *G01R 33/46* (2013.01); *H01L 51/5076* (2013.01)

COMPOUND AND ORGANIC ELECTRONIC DEVICE USING THE SAME

CROSS-REFERENCE TO RELATED APPLICATIONS

Pursuant to 35 U.S.C. § 119(e), this application claims the benefits of the priority to U.S. Provisional Patent Application No. 62/430,982, filed Dec. 7, 2016 and of the priority to U.S. Provisional Patent Application No. 62/433,371, filed Dec. 13, 2016, The contents of the prior applications are incorporated herein by their entirety.

BACKGROUND OF THE INVENTION

1. Field of the Invention

The present invention relates to a novel compound and an organic electronic device using the same, more particularly to a novel compound as electron-transporters and an organic electronic device using the same

2. Description of the Prior Arts

With the advance of technology, various organic electronic devices that make use of organic materials have been energetically developed. Examples of organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching Tang and Steven VanSlyke of Kodak Company deposited an electron transport material, such as tris(8-hydroxyquinoline)aluminum (III) (abbreviated as $Alq_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons thereby emitting light when the excitons decay from excited state to ground state.

Another approach is to modify the materials of ETL for OLEDs to render the electron transport materials to exhibit hole-blocking ability. Examples of conventional electron transport materials include 3,3'-[5'-[3-(3-Pyridinyl)phenyl]][1,1':3',1''-terphenyl]-3,3''-diyl]bispyridine(TmPyPb), 1,3,5-tris(1-phenyl-1H-benzimidazol-2-yl )benzene(TPBi), tris(2,4,6-trimethyl-3-(pyridin-3-yl)phenyl)borane(3TPYMB), 1,3-bis(3,5-dipyrid-3-yl-phenyl)benzene(BmPyPb), and 9,10-bis(3-(pyridin-3-yl)phenyl)anthracene(DPyPA).

However, even using the foresaid electron transport materials, the current efficiency of OLEDs still needs to be improved. Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to improve the efficiency of the organic electronic device.

To achieve the foresaid objectives, the present invention provides a novel compound represented by the following Formula (I):

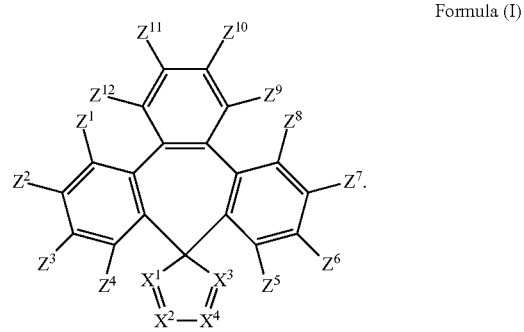

Formula (I)

In Formula (I), $X^1$ and $X^2$ are each independently $C(R^a)$, the two ($R^a$)s are the same or different, and the two ($R^a$)s are joined together to form a first aryl ring.

In Formula (I), $X^3$ and $X^4$ are each independently $C(R^b)$, the two ($R^b$)s are the same or different, and the two $(R^b)^s$ are joined to form a second aryl ring, wherein the second aryl ring is a polycyclic aromatic ring.

In Formula (I), $Z^1$ to $Z^{12}$ are each independently selected from the group consisting of: a hydrogen atom, a deuterium atom, a halogen group, a cyano group, a nitro group, an alkyl group having 1 to 40 carbon atoms, an alkenyl, group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms.

In accordance with the present invention, the polycyclic aromatic ring. extended from $X^3$ and $X^4$ in Formula (I) contains at least two cyclic aryl rings joined or fused together. The at least two cyclic aryl rings of the polycyclic aromatic ring are all constructed by carbon atoms without any heteroatom such as nitrogen, oxygen, or sulfur atoms, while the polycyclic aromatic ring may be attached with any substitution group containing atoms other than carbon atoms.

In accordance with the present invention, the double bond between $X^1$ and $X^2$ in Formula (I) and the bonds between the two joined ($R^a$)s are conjugated and commonly construct the first aryl ring. Likely, the double bond between $X^3$ and $X^4$ in Formula (I) and the bonds between the two joined ($R^b$)s are conjugated and commonly construct the polycyclic aromatic ring. In accordance with the present invention, the first aryl ring extended from $X^1$ and $X^2$ and the polycyclic aromatic ring extended from $X^3$ and $X^4$ are joined and fused to become an aromatic group containing at least six conjugated double bonds, preferably an aromatic group containing at least eight conjugated double bonds.

The polycyclic aromatic ring extended from $X^3$ and $X^4$ may be, for example, but not limited to: a substituted or unsubstituted naphthalene ring, a substituted or unsubstituted anthracene ring, a substituted or unsubstituted phenanthrene ring, a substituted or unsubstituted fluorene ring, a substituted or unsubstituted pyrene ring, a substituted or unsubstituted benzophenanthrene ring, a substituted or unsubstituted benzopyrene ring, a substituted or unsubstituted fluoranthene ring, a substituted or unsubstituted benzofluoranthene ring, or a substituted or unsubstituted triphenylene ring. The foresaid polycyclic aromatic ring may be substituted with at least one deuterium atom, at least one alkyl group having 1 to 12 carbon atoms, at least one alkenyl group having 2 to 12 carbon atoms, at least one alkynyl group having 2 to 12 carbon atoms, or at least one aryl group having 6 to 12 ring carbon atoms. For example, the substituted fluorene ring may be a fluorene ring i.e., substituted with one methyl group, two methyl groups, or two phenyl groups, the substituted fluorene ring may be 9-methylfluorene ring, 9,9-dimethylfluorene ring, or 9,9-diphenylfluorene ring.

Preferably, $Z^1$ to $Z^{12}$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 30 ring carbon atoms, an alkoxy group having 1 to 12 carbon atoms, an aryloxy group having 6 to 30 ring carbon atoms, an alkylsilyl group having 1 to 12 carbon atoms, an arylsilyl group having 6 to 30 ring carbon atoms, an alkylboron group having 1 to 12 carbon atoms, an arylboron group having 6 to 30 ring carbon atoms, a phosphine group having 1 to 12 carbon atoms, and a phosphine oxide group having 1 to 12 carbon atoms.

For example, the compound is represented by any one of the following Formulae (I-I) to (I-XII):

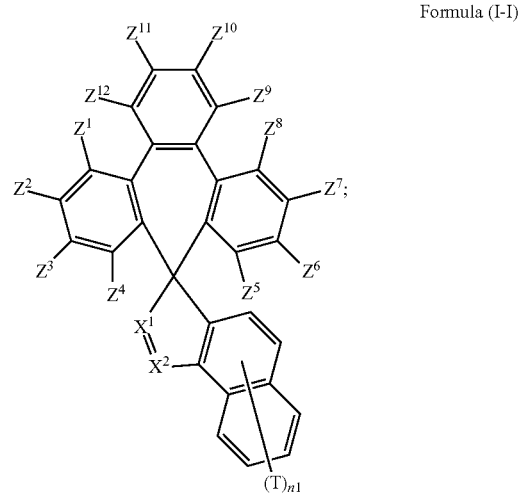

Formula (I-I)

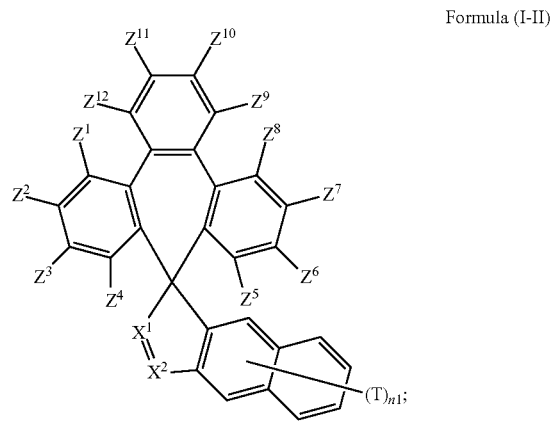

Formula (I-II)

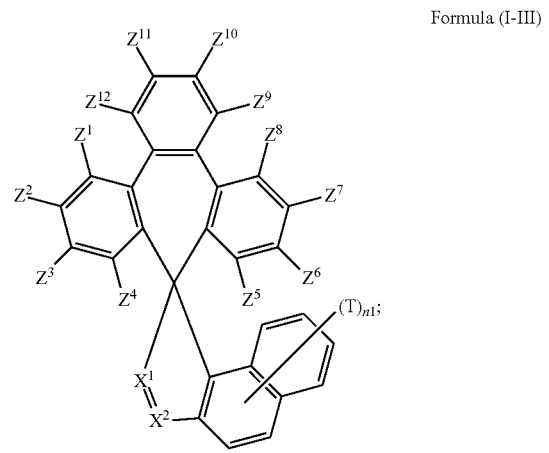

Formula (I-III)

-continued
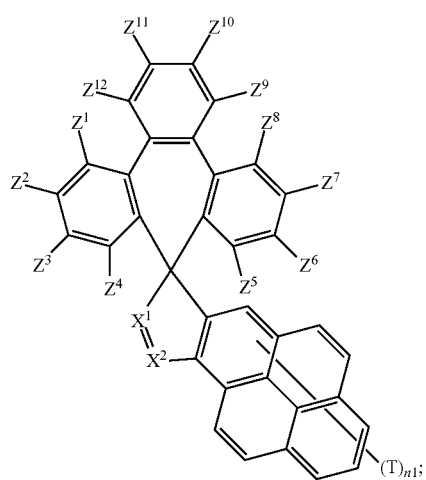
Formula (I-IV)
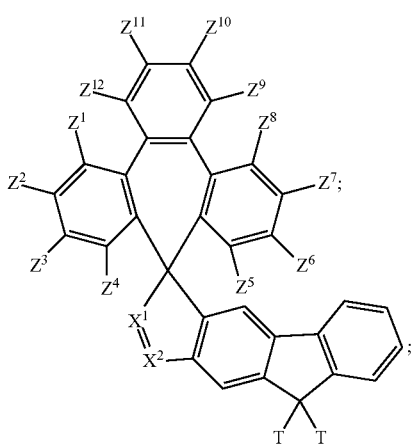
Formula (I-VII)
Formula (I-V)
Formula (I-VIII)
Formula (I-VI)
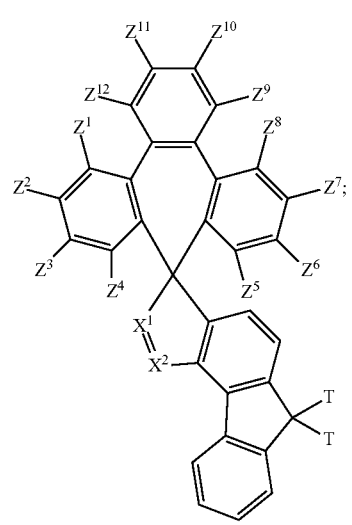
Formula (I-IX)

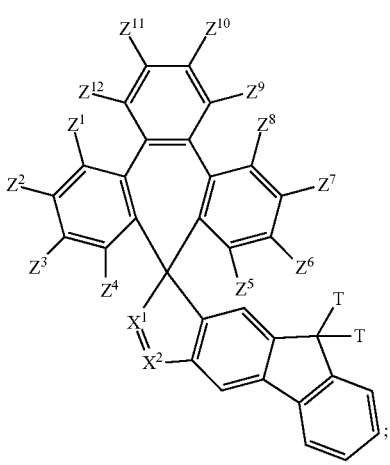

Formula (I-X)

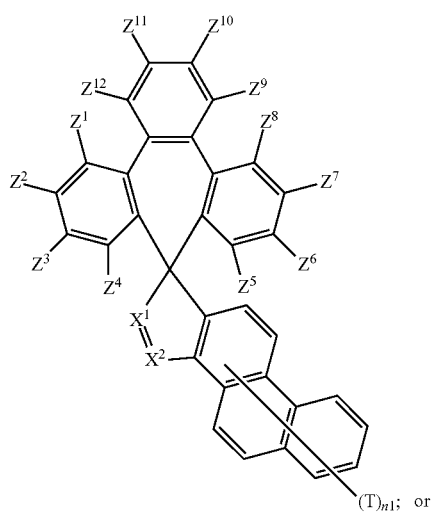

Formula (I-XI)

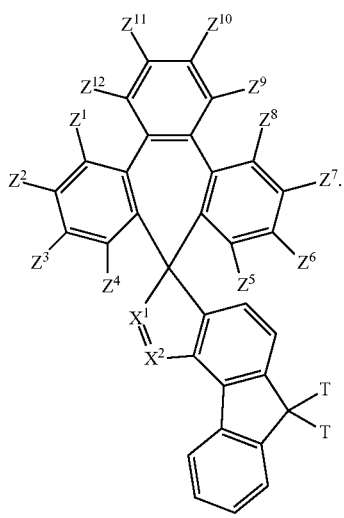

Formula (I-XII)

In the above Formulae (I-I) to (I-XII), n1 may be a positive integral from 0 to 4. T may be, for example, but not limited to: a hydrogen atom, a deuterium atom, a methyl group, an ethyl group, a propyl group, a butyl group, a pentyl group, a hexyl group, or a phenyl group.

Preferably, the first aryl ring extended from $X^1$ and $X^2$ in any one of foresaid formulae may be a substituted or unsubstituted 6 to 60-membered carbon ring, preferably a substituted or unsubstituted 6 to 20-membered carbon ring. For example, the substituted or unsubstituted 6 to 60-membered carbon ring may be selected from the group consisting of a substituted or unsubstituted benzene ring, a substituted or unsubstituted naphthalene ring, a substituted or unsubstituted anthracene ring, a substituted or unsubstituted phenanthrene ring, a substituted or unsubstituted pyrene ring, a substituted or unsubstituted benzophenanthrene ring, a substituted or unsubstituted benzopyrene ring, a substituted or unsubstituted fluoranthene ring, a substituted or unsubstituted benzofluoranthene ring, and a substituted or unsubstituted fluorene ring, but is not limited thereto. More preferably, the substituted or unsubstituted 6 to 60-membered carbon ring is a substituted or unsubstituted benzene structure. The substitution group on the 6 to 60-membered carbon ring may be, but not limited to, a deuterium atom, a halogen group, a cyano group, a nitro group, an alkyl group having 1 to 12 carbon atoms, an alkenyl group having 2 to 12 carbon atoms, or an alkynyl group having 2 to 12 carbon atoms.

Preferably, at least one of $Z^1$ to $Z^8$ in any one of foresaid formulae may be selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, a aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms, a phosphine group having 1 to 40 carbon atoms and substituted with at least one functional group, and a phosphine oxide group having 1 to 40 carbon atoms and substituted with at least one functional group: and the other of $Z^1$ to $Z^8$ in any one of foresaid formulae may be a hydrogen atom, a deuterium atom, or any other substitution groups as mentioned in the specification. Said functional group is selected from the group consisting of: a cyano group, a nitro group, a trifluoromethyl group, a fluoro group, and a chloro group.

More specifically, at least one of $Z^1$ to $Z^8$ in any one of foresaid formulae may be a specific aromatic substitution. The specific aromatic substitution may be selected from the group consisting of:

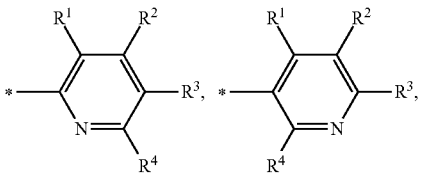

-continued
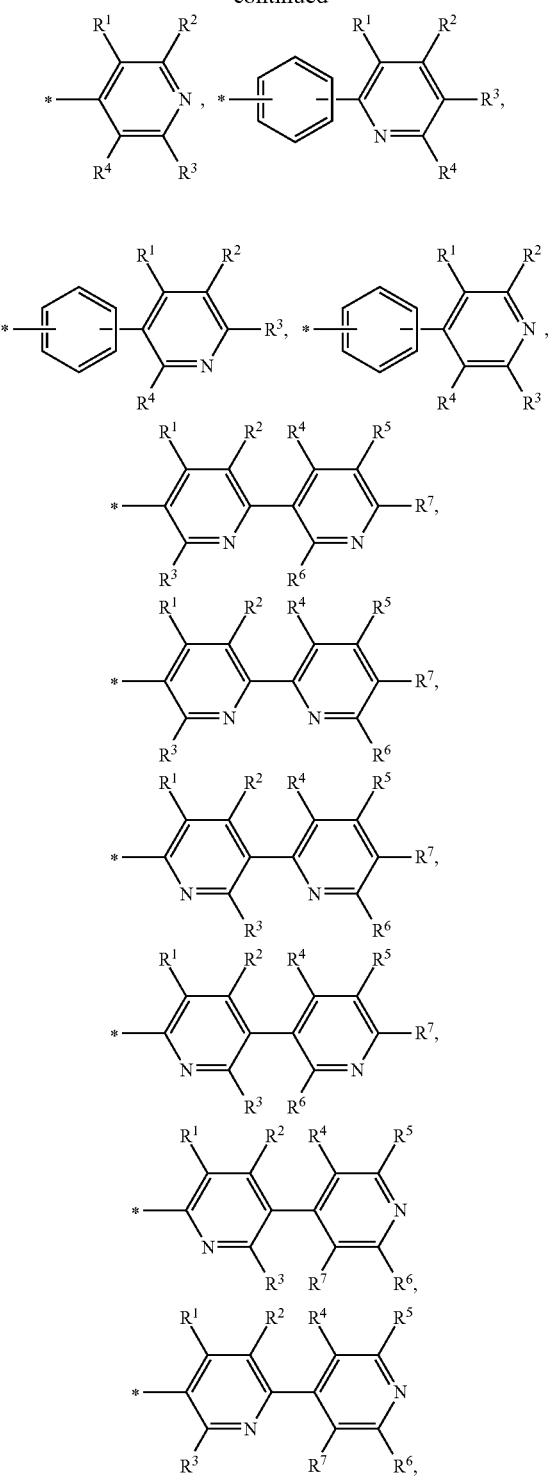
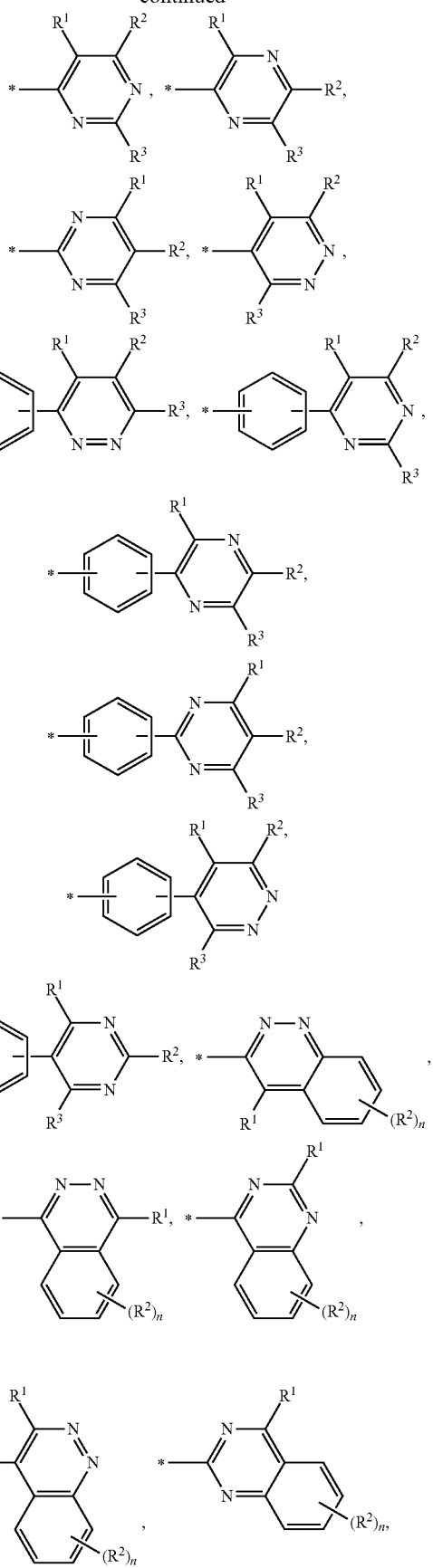

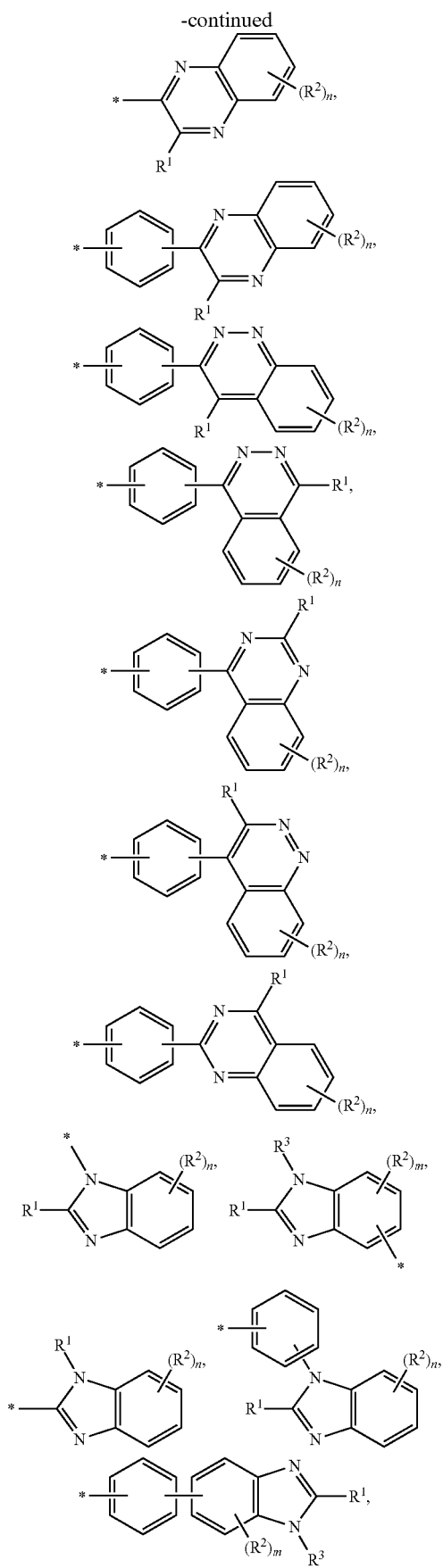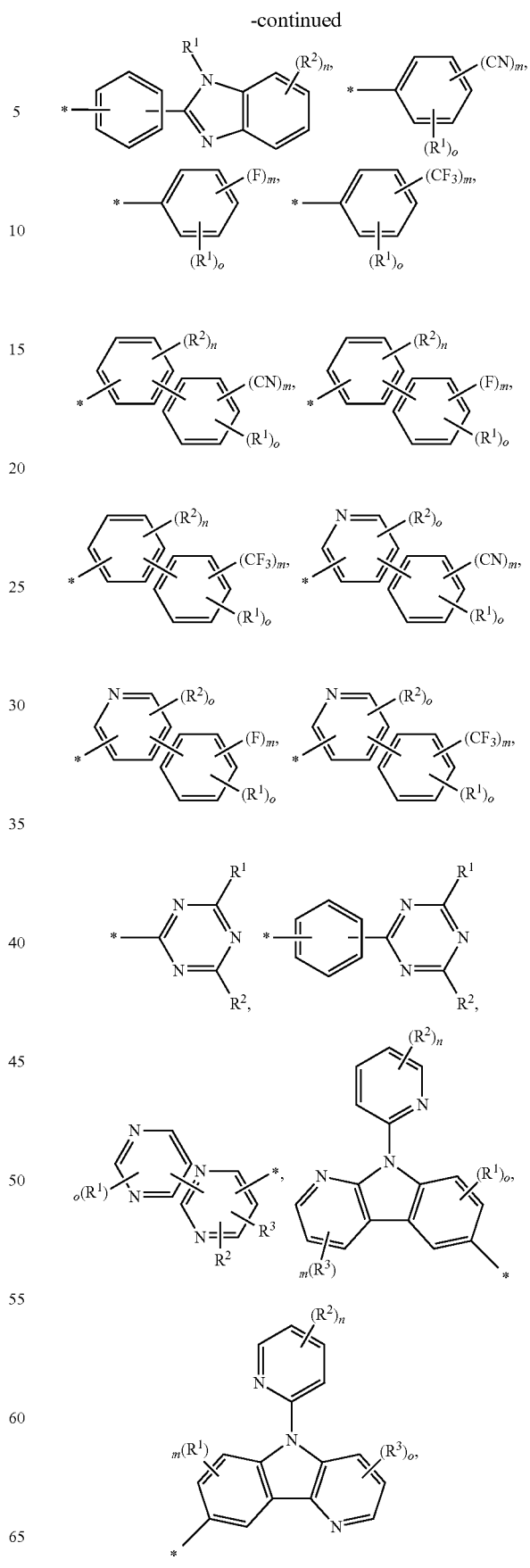

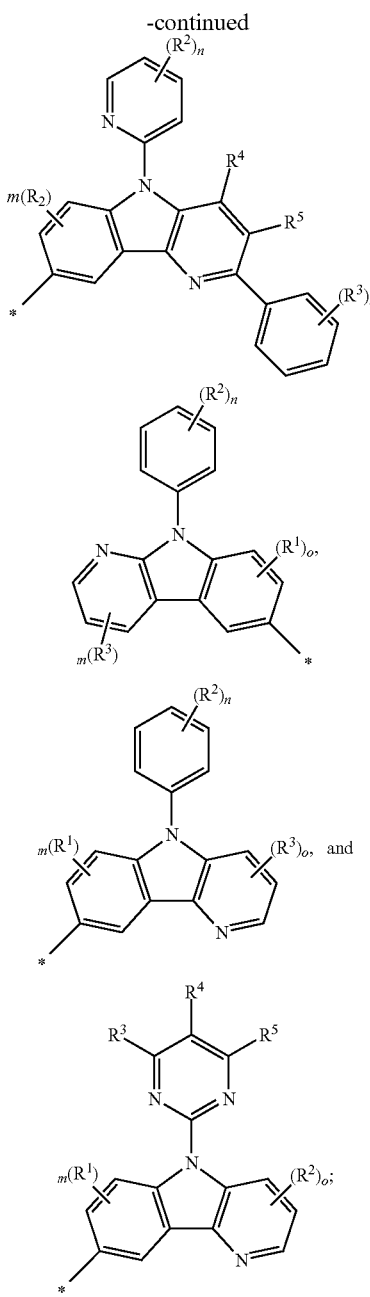

wherein $R^1$ to $R^7$ are each independently selected from the group consisting of a hydrogen atom, a deuterium atom, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

n is a positive integral from 0 to 4, m is a positive integral from 0 to 3, o is a positive integral from 0 to 3, and the total of m and o is not more than 5.

Preferably, $R^1$ to $R^3$ each may independently be, for example, but not limited to, phenyl group, pyridine group, pyrimidine group, pyrazine group, pyridazine group, phenylpyridine group, phenylpyrimidine group, phenylpyrazine group, or phenylpyridazine group.

In an embodiment at least one of $Z^1$ to $Z^8$ in any one of foresaid formulae may preferably be

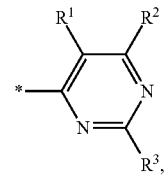

wherein $R^1$ may be pyridinyl group or cyanophenyl group, and $R^2$ and $R^3$ maybe any substitution group as stated above.

In another embodiment, at least one of $Z^1$ to $Z^8$ in any one of foresaid formulae may preferably be

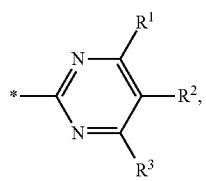

wherein $R^2$ may be pyridinyl group or cyanophenyl group, and $R^1$ and $R^3$ maybe any substitution group as stated above.

Preferably, at least one of $Z^1$, $Z^2$, $Z^3$, $Z^6$, $Z^7$, and $Z^8$ in any one of foresaid formulae is a substituted triazine group with two phenyl groups, two pyridine groups, two pyrimidine groups, two pyrazine groups, two pyridazine groups, two phenylpyridine groups, two phenylpyrimidine groups, two phenylpyrazine groups, or two phenylpyridazine groups.

Preferably, at least one of $Z^1$, $Z^2$, $Z^3$, $Z^6$, $Z^7$, and $Z^8$ in any one of foresaid formulae may be the specific aromatic substitution as stated above, and $Z^4$ and $Z^5$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

Preferably, at least one of $Z^2$, $Z^3$, $Z^6$, and $Z^7$ in any one of foresaid formulae is selected from the group consisting of

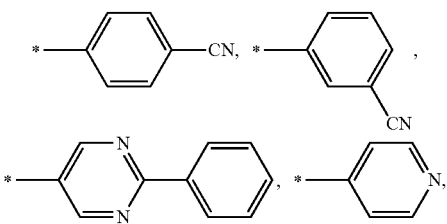

-continued
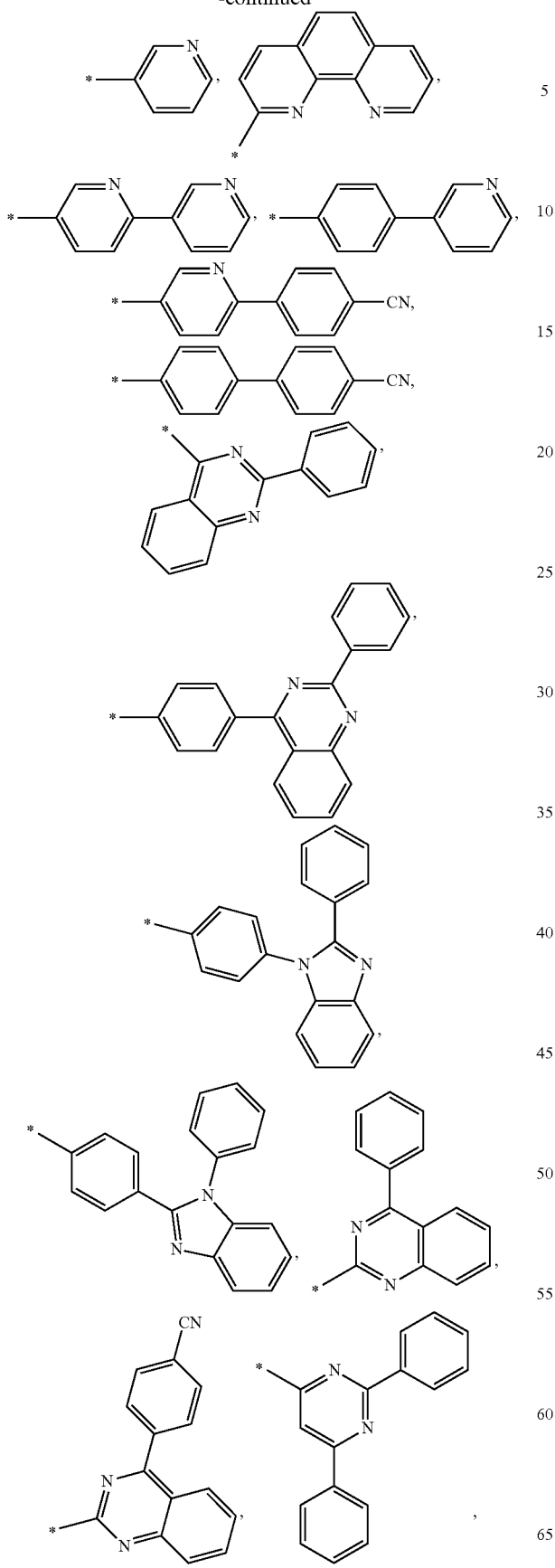
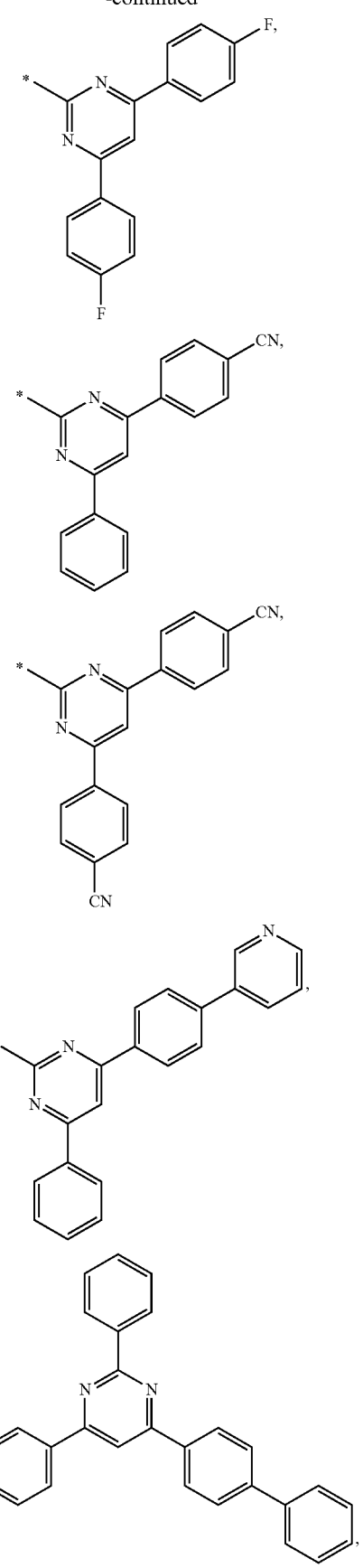

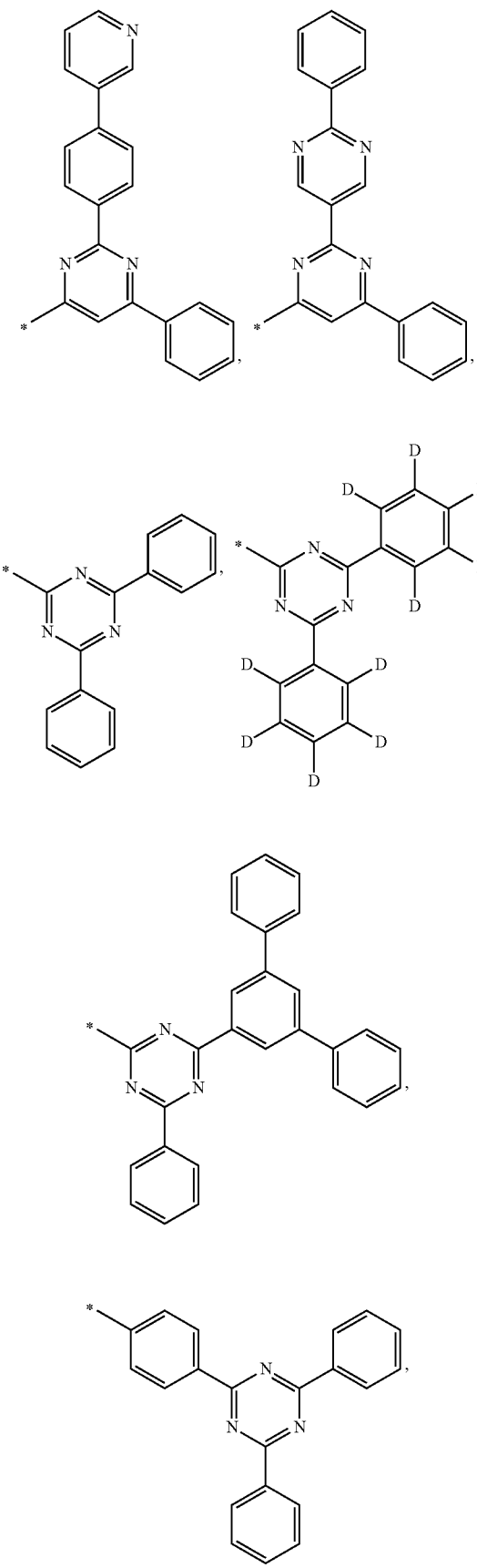

Preferably, $Z^9$ to $Z^{12}$ in any one of foresaid formulae are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

In accordance with the present invention, $Z^1$ and $Z^8$ may be the same or different. In accordance with the present invention, $Z^2$ and $Z^7$ may be the same or different. In accordance with the present invention, $Z^3$ and $Z^8$ may be the same or different. In one embodiment, any two of $Z^1$, $Z^2$, $Z^3$, $Z^6$, $Z^7$, and $Z^8$ may be the same substitution as stated above, and the others of $Z^1$, $Z^2$, $Z^3$, $Z^6$, $Z^7$, and $Z^8$ may be a hydrogen atom, a deuterium atom, a halogen group, a cyano group, a nitro group, an alkyl group having 1 to 12 carbon atoms, an alkenyl group having 2 to 12 carbon atoms, or an alkynyl group having 2 to 12 carbon atoms.

For example, $Z^1$, $Z^4$ to $Z^8$ are each independently a hydrogen atom or a deuterium atom, and $Z^2$ and/or $Z^3$ may be a specific aromatic substitution. Or, $Z^1$, $Z^2$, $Z^4$, $Z^5$, $Z^7$ and $Z^8$ are each independently a hydrogen atom or a deuterium atom, and $Z^3$ and $Z^6$ are both the above specific aromatic substitutions For example, the compound may be selected from the group consisting of:

Compound I

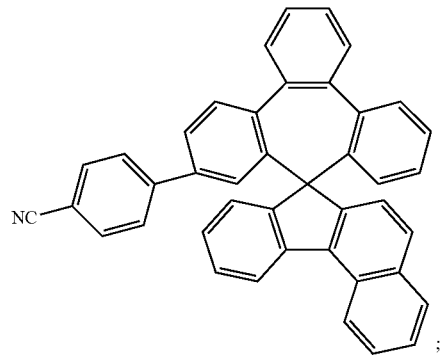

;

Compound II

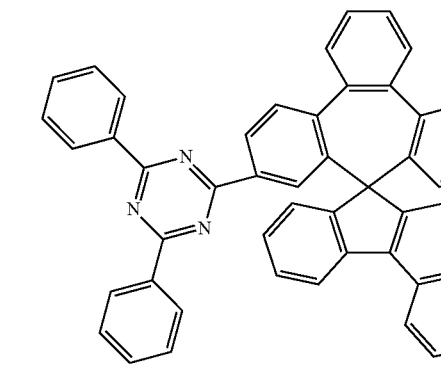

;

Compound III

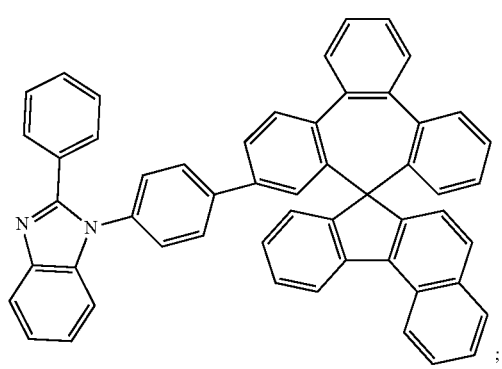

;

Compound IV

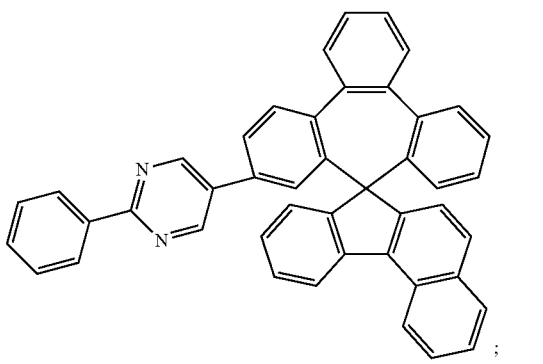

;

Compound V

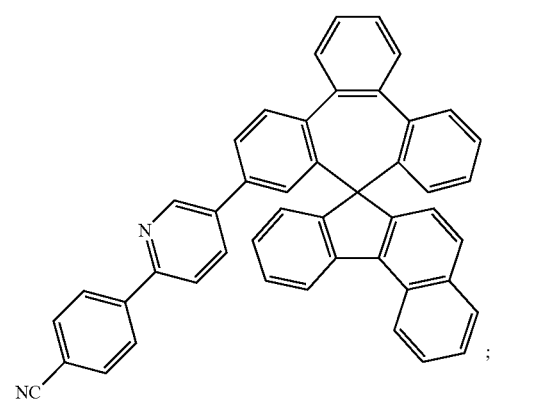

;

Compound VI

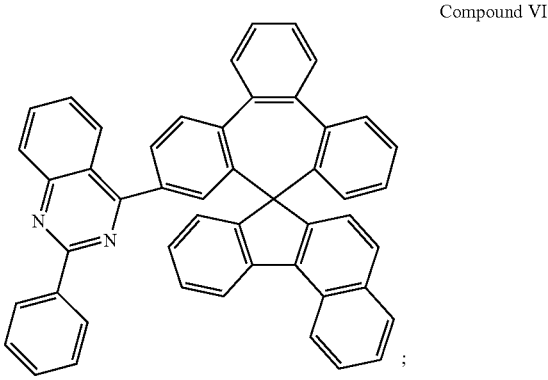

;

Compound VII

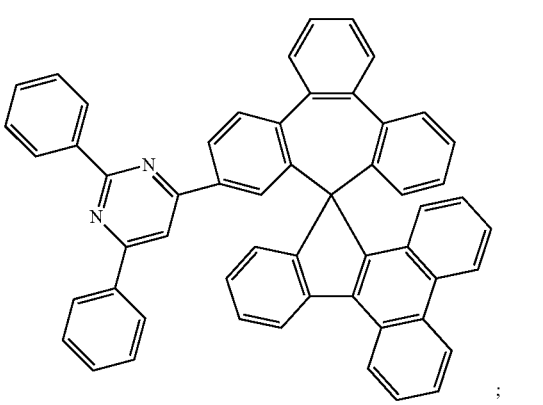

;

Compound VIII
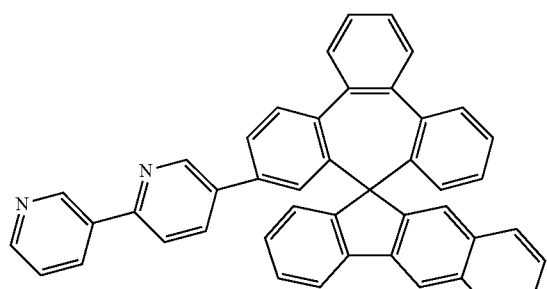
Compound IX
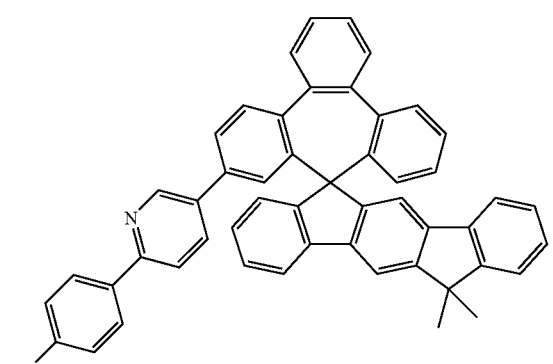
Compound X
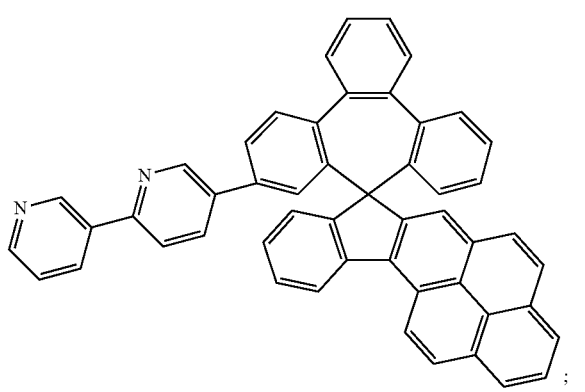
Compound XI
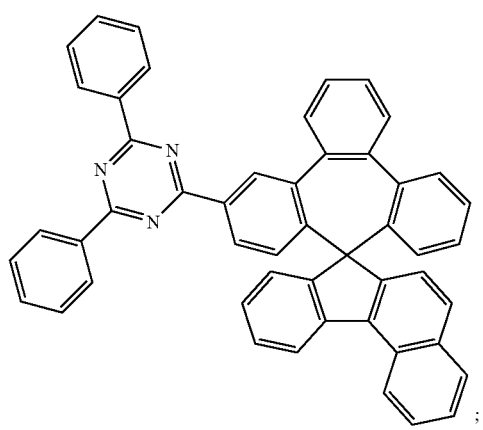
Compound XII
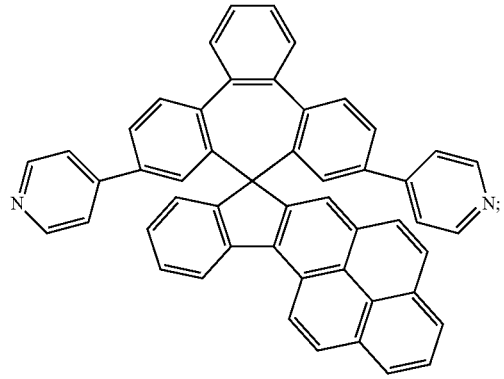
Compound XIII
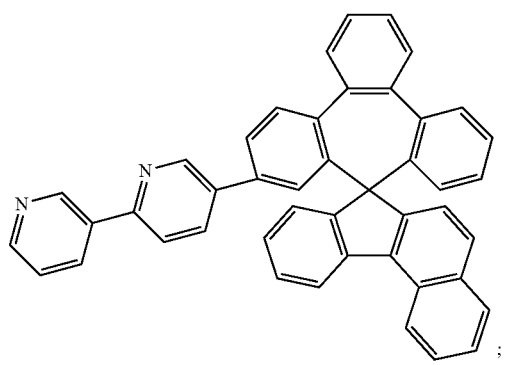
Compound XIV
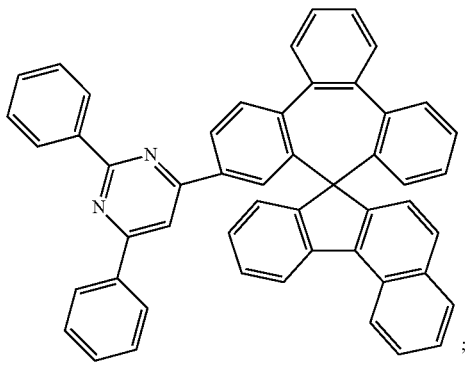
Compound XV
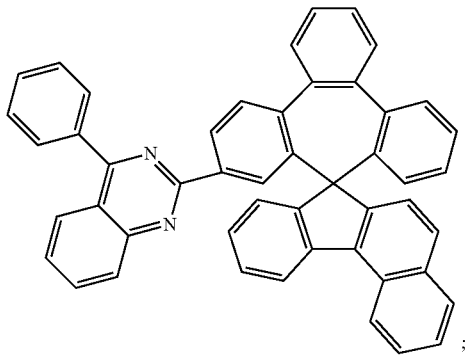

Compound XVI
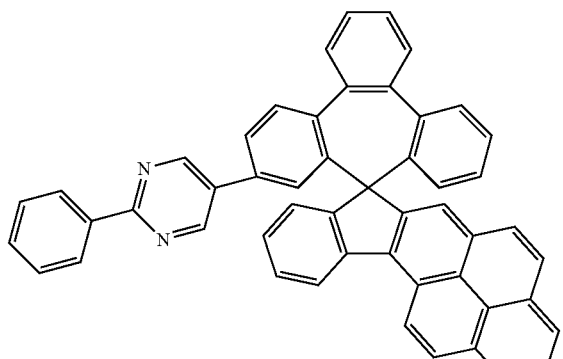
Compound XVII
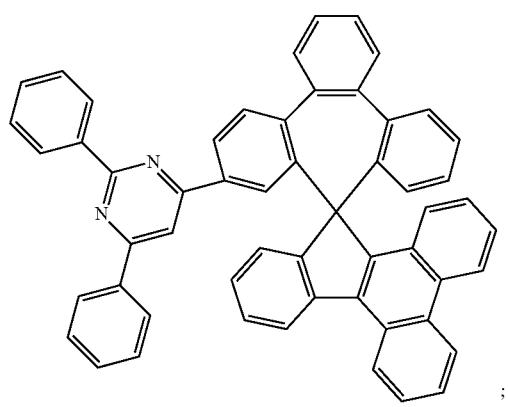
Compound XVIII
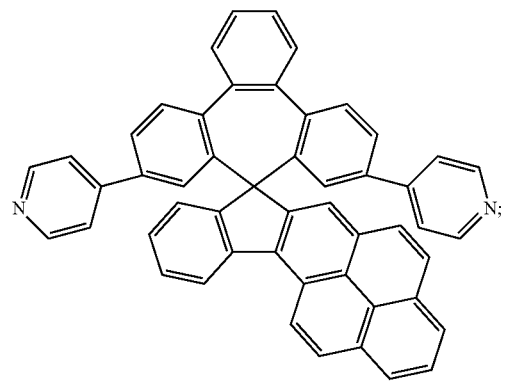
Compound XIX
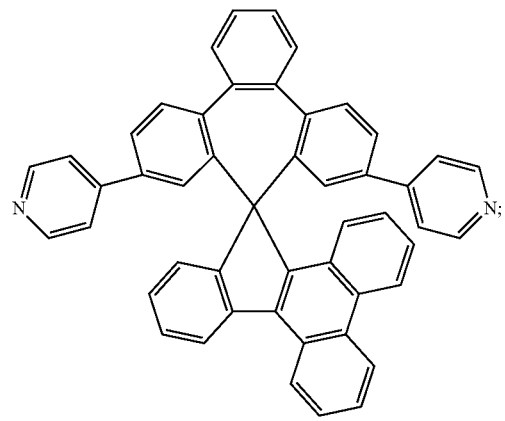
Compound XX
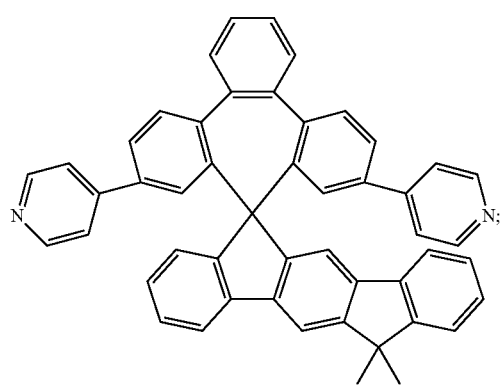
Compound XXI
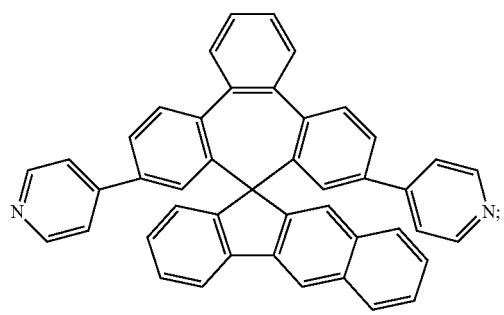
Compound XXII
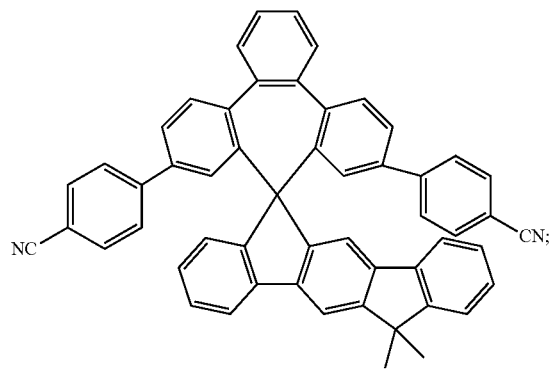
Compound XXIII
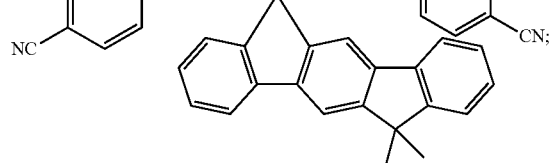

Compound XXIV
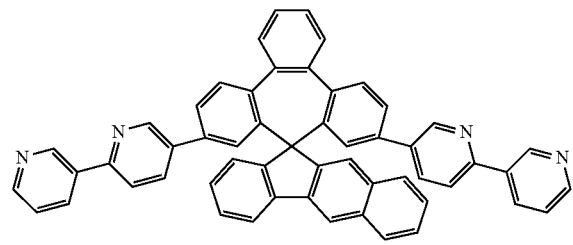
Compound XXV
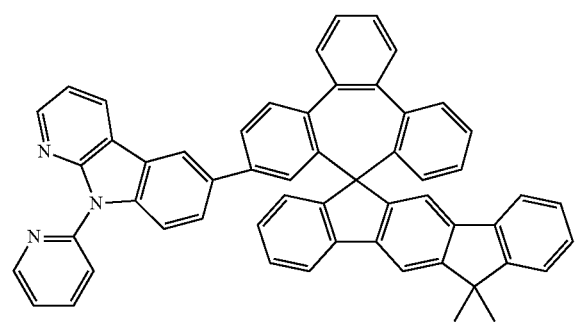
Compound XXVI
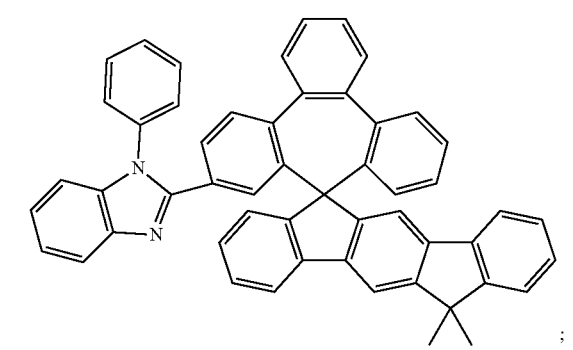
Compound XXVII
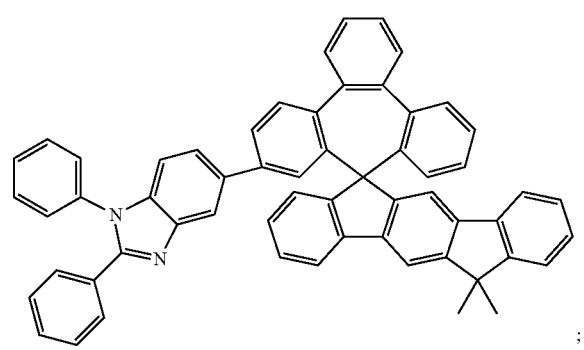
Compound XXVIII
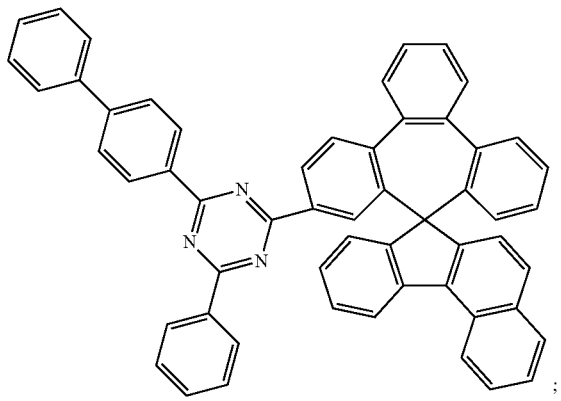
Compound XXIX
Compound XXX
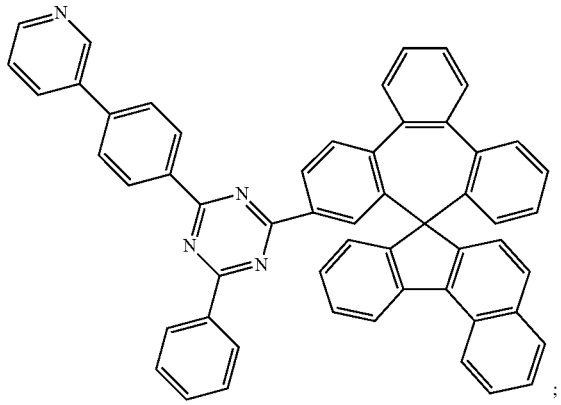

Compound XXXI
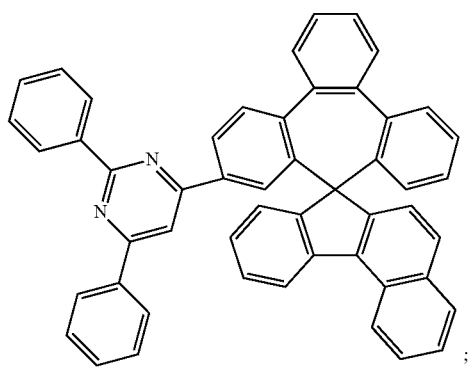
Compound XXXII
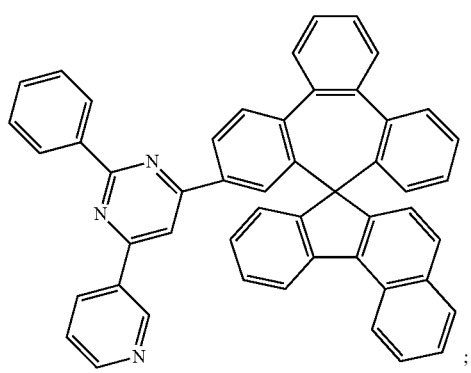
Compound XXXIII
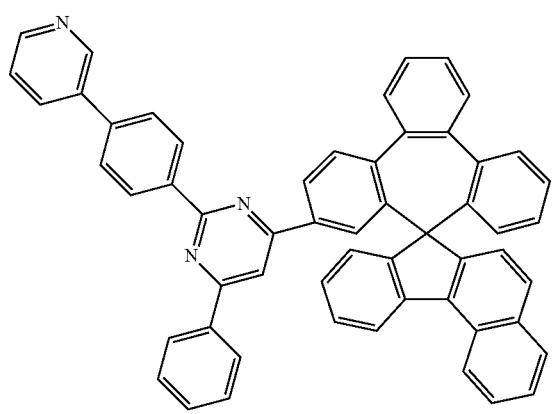
Compound XXXIV
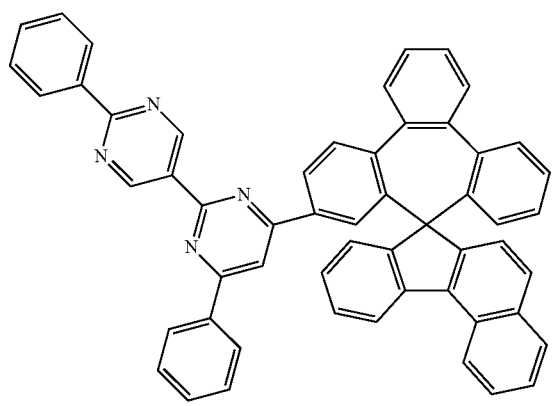
Compound XXXV
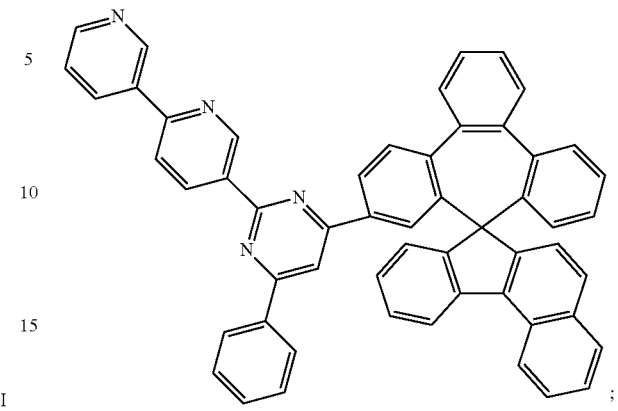
Compound XXXVI
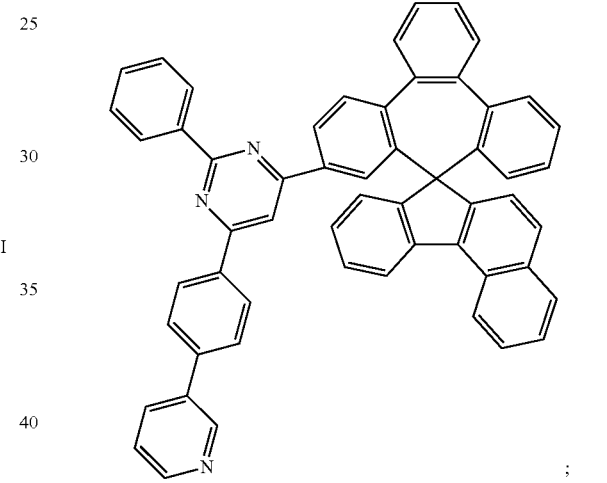
Compound XXXVII
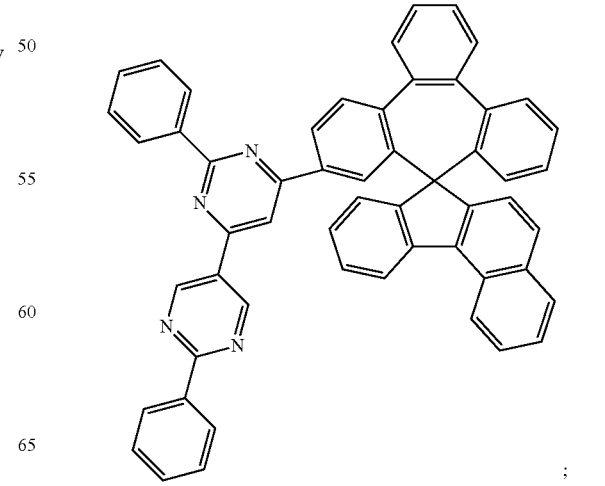

Compound XXXVIII
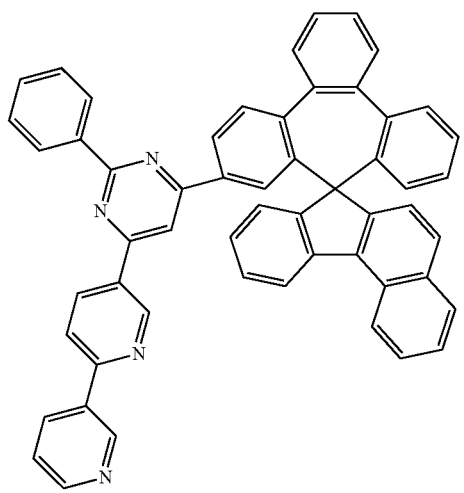
Compound XXXIX
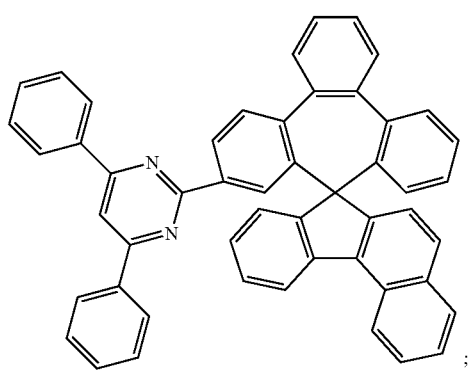
Compound XL
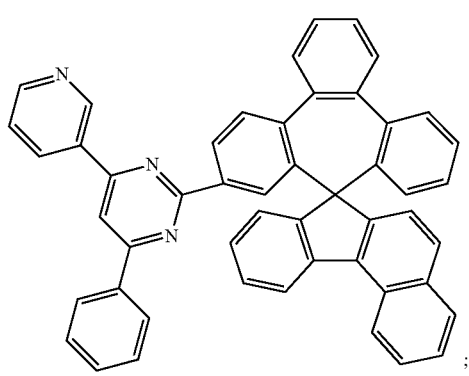
Compound XLI
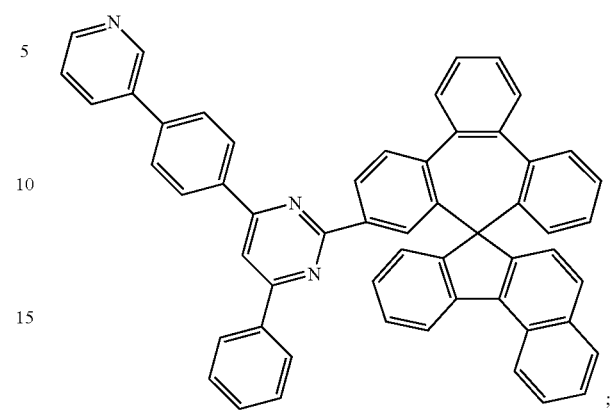
Compound XLII
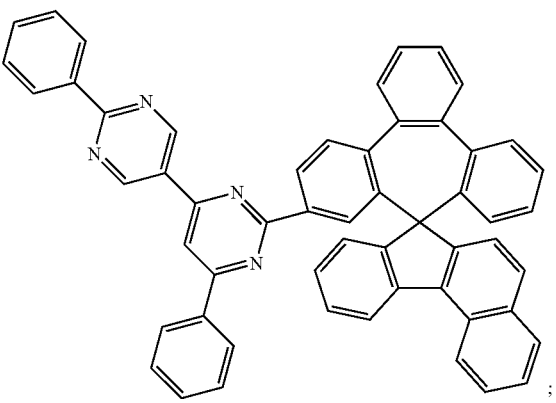
Compound XLIII
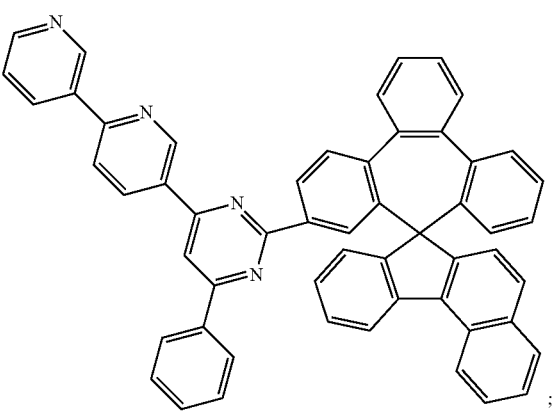

Compound XLIV
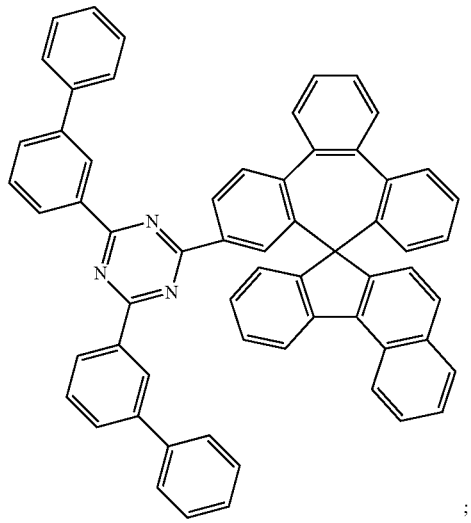
Compound XLV
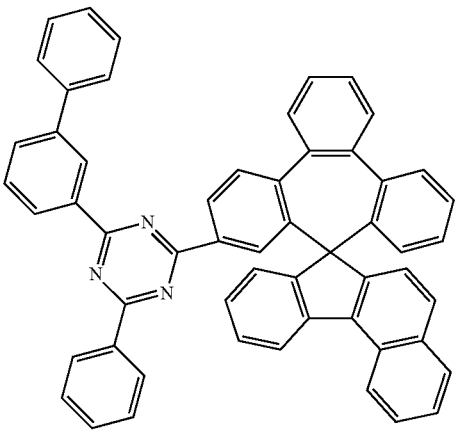
Compound XLVI
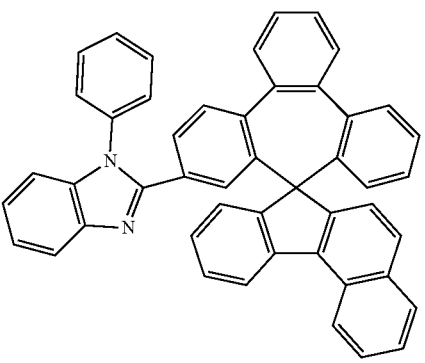
Compound XLVII
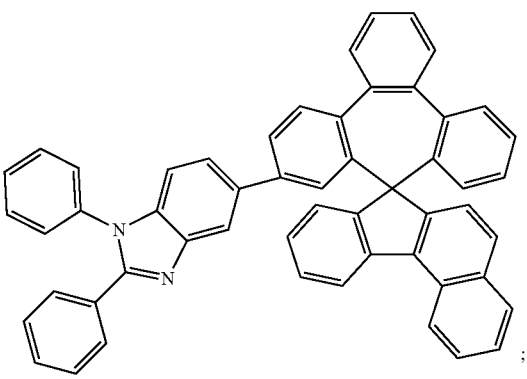
Compound XLVIII
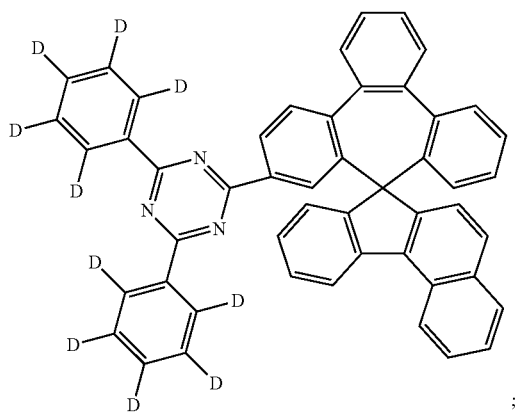
Compound IL
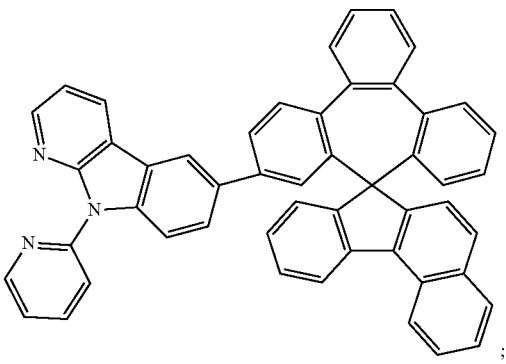
Compound L Compound LI
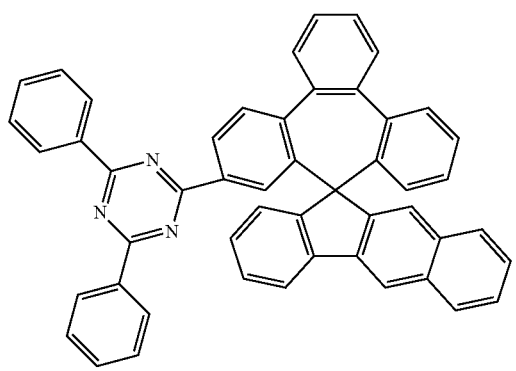
Compound LII
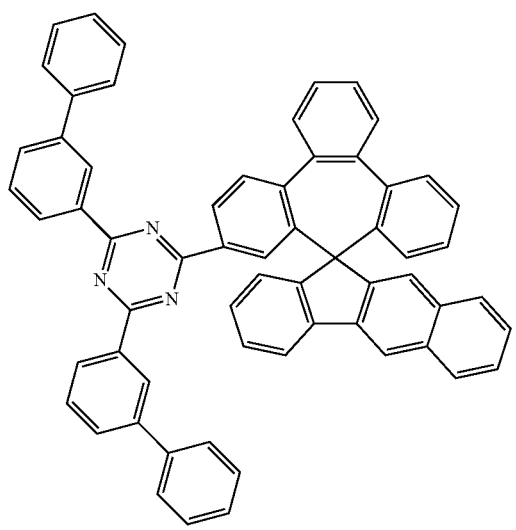
Compound LIII
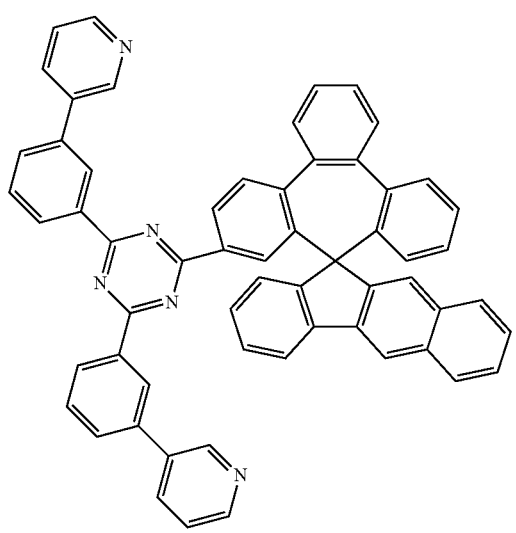
Compound LIV
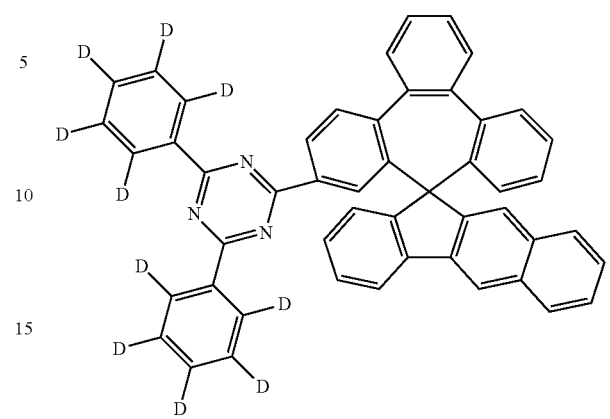
Compound LV
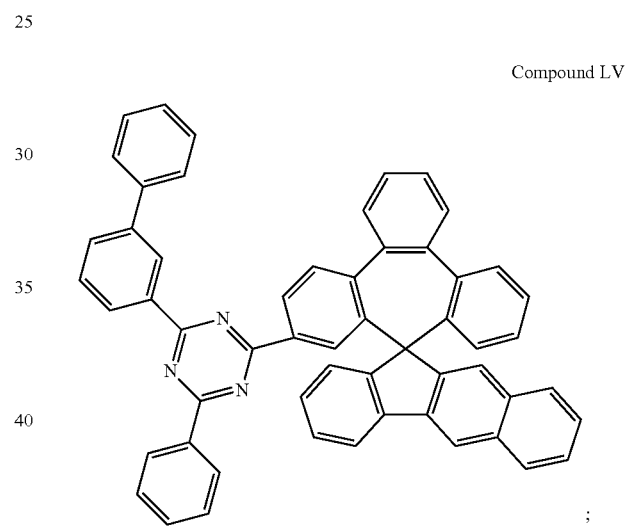
Compound LVI
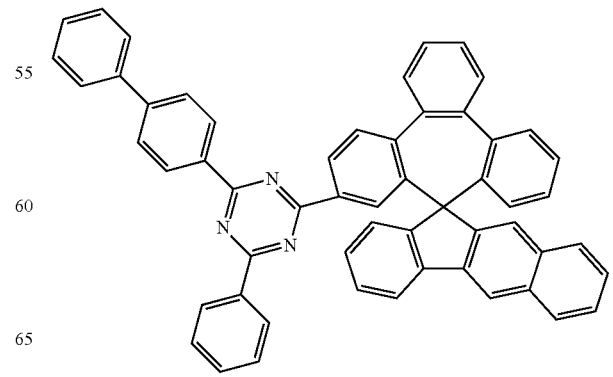

Compound LVII
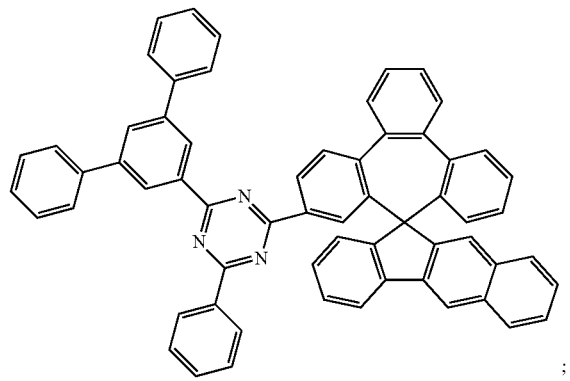
Compound LVIII
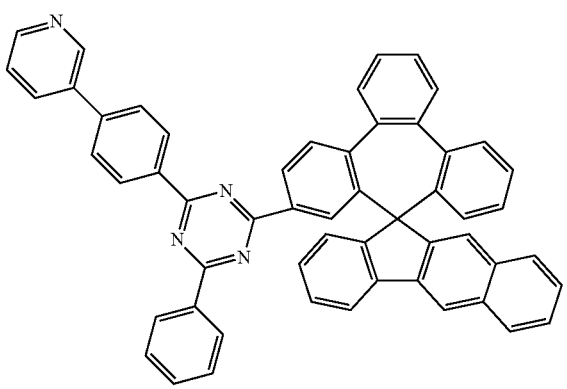
Compound LIX
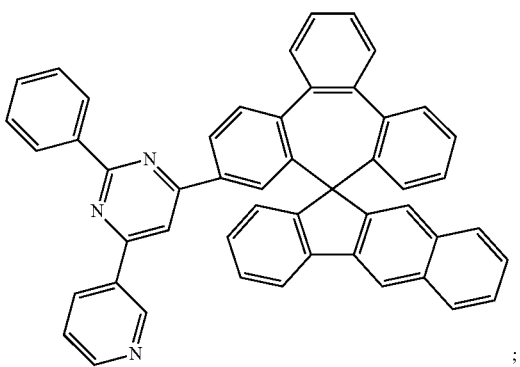
Compound LXI
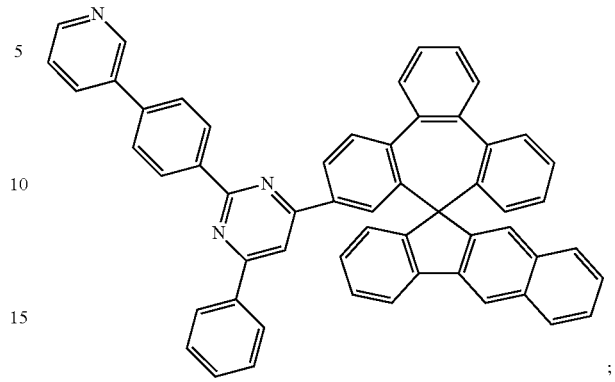
Compound LXII
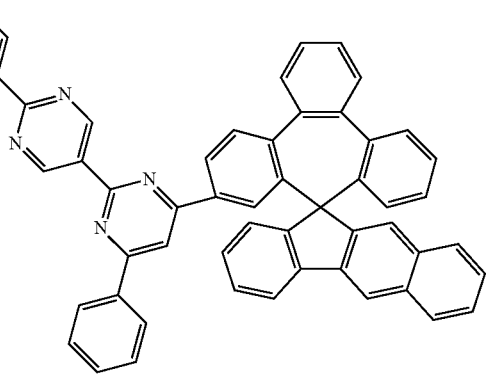
Compound LXIII
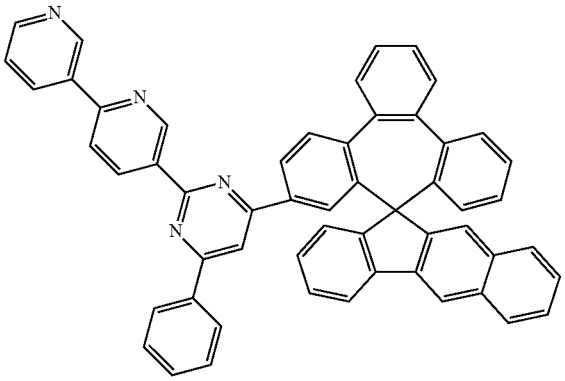

Compound LXIV
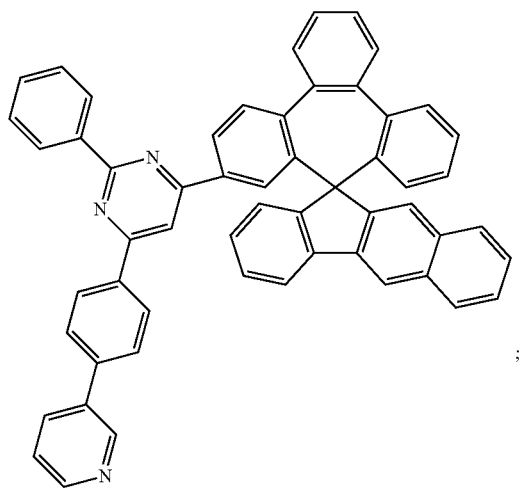
Compound LXV
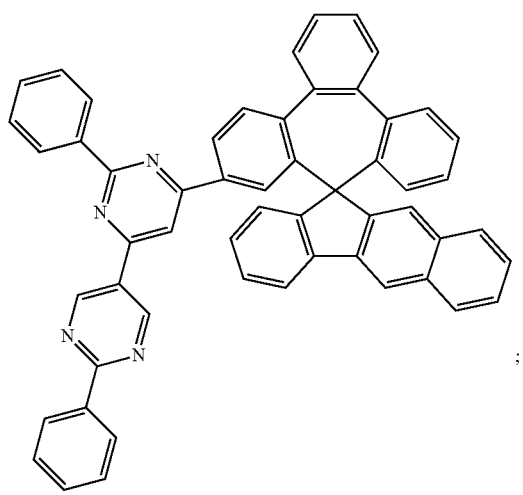
Compound LXVI
Compound LXVII
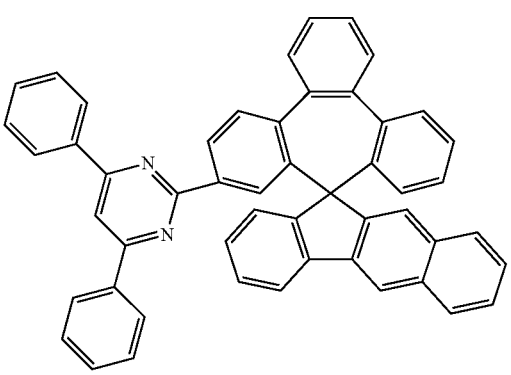
Compound LXVIII
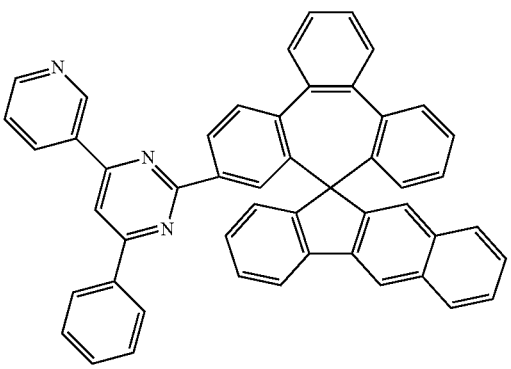
Compound LXIX
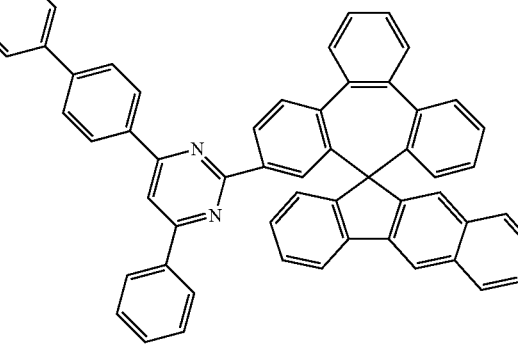
Compound LXX
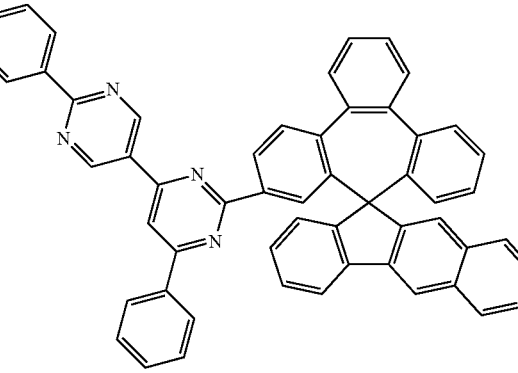

Compound LXXI
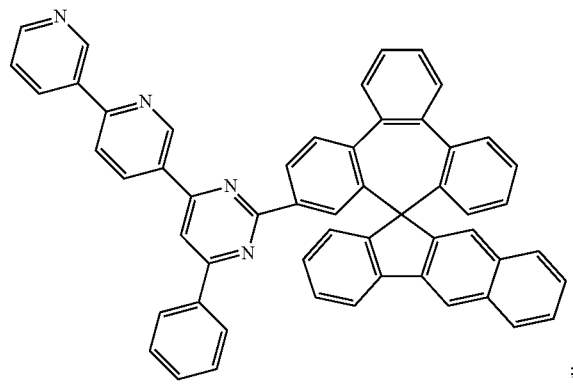
Compound LXXII
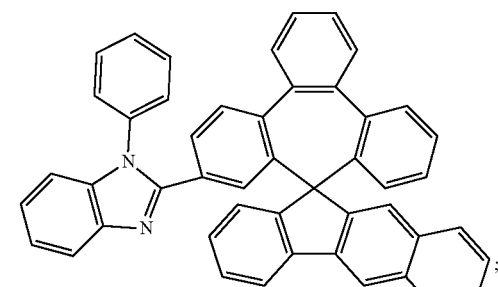
Compound LXXIII
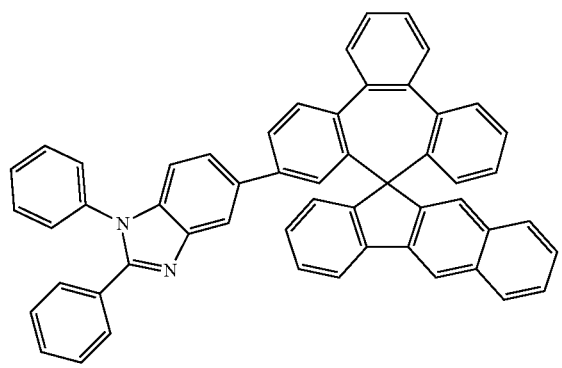
Compound LXXIV
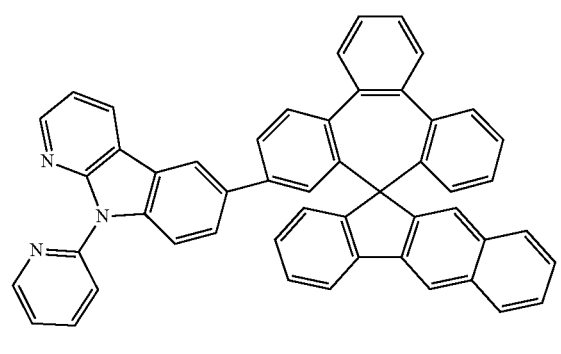
Compound LXXV
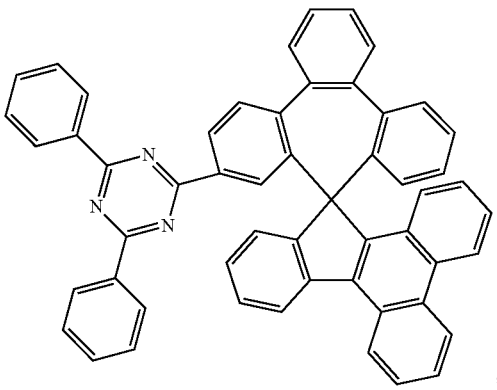
Compound LXXVI
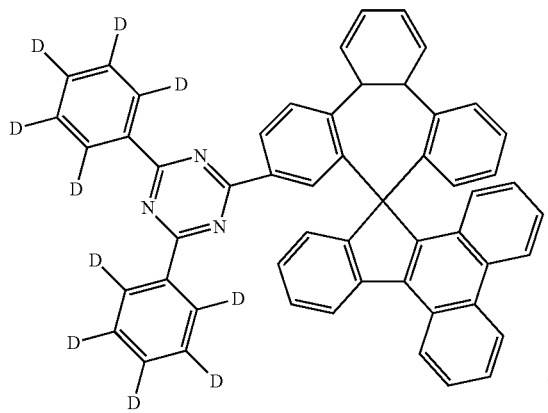
Compound LXXVII
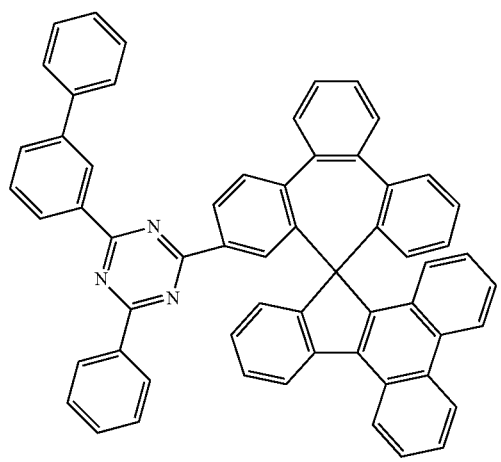

Compound LXXVIII
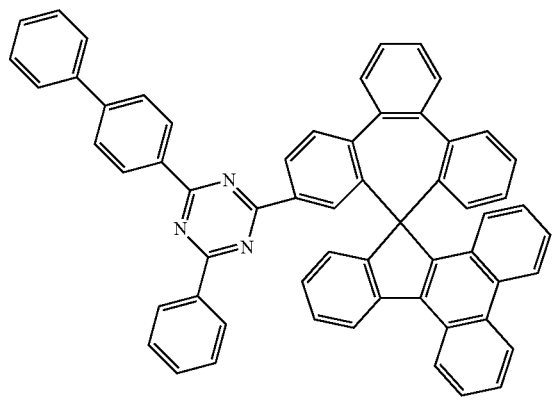
;
Compound LXXIX
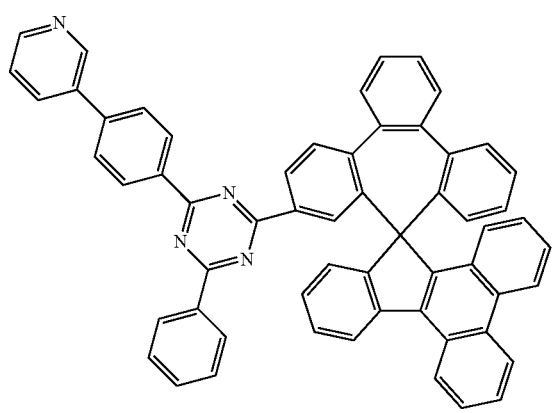
;
Compound LXXX
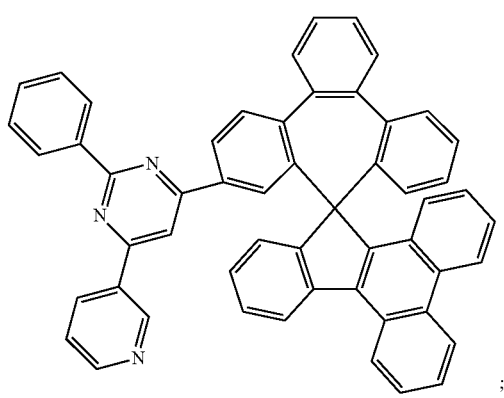
;
Compound LXXXI
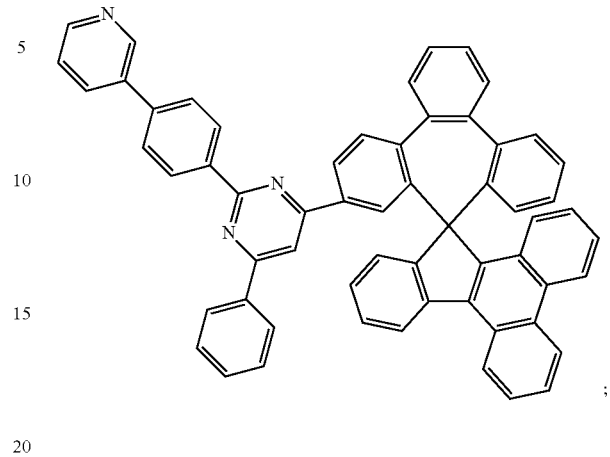
;
Compound LXXXII
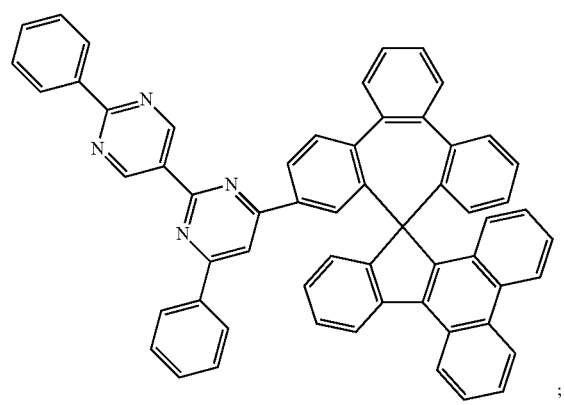
;
Compound LXXXIII
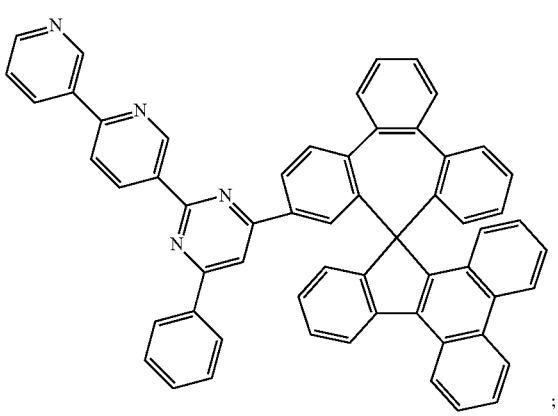
;

Compound LXXXIV
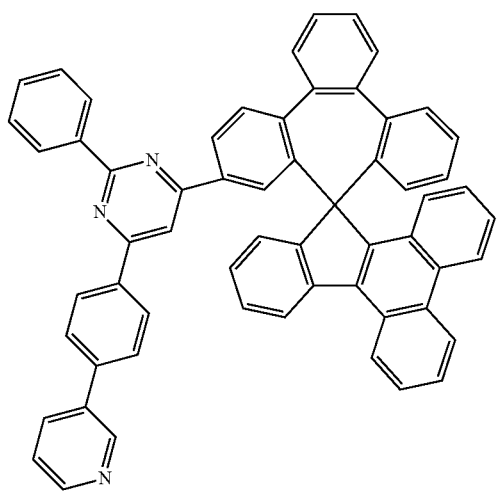
Compound LXXXV
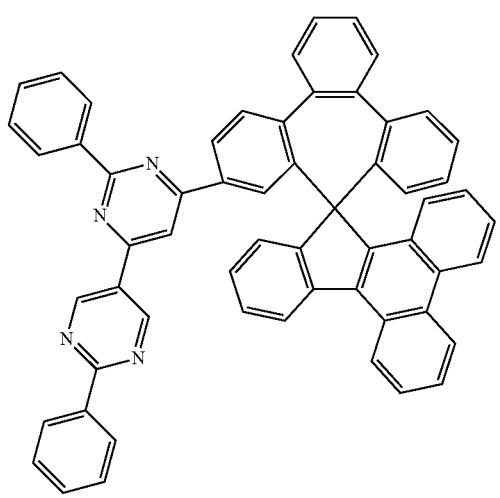
Compound LXXXVI
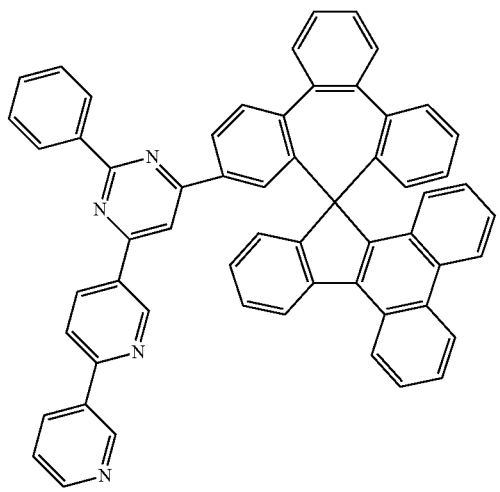
Compound LXXXVII
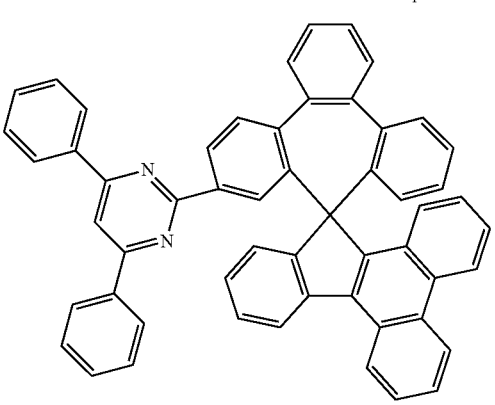
Compound LXXXVIII
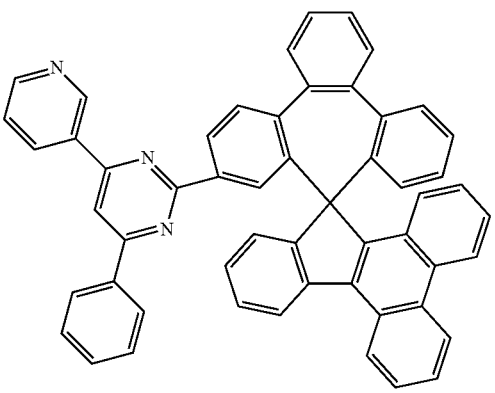
Compound LXXXIX
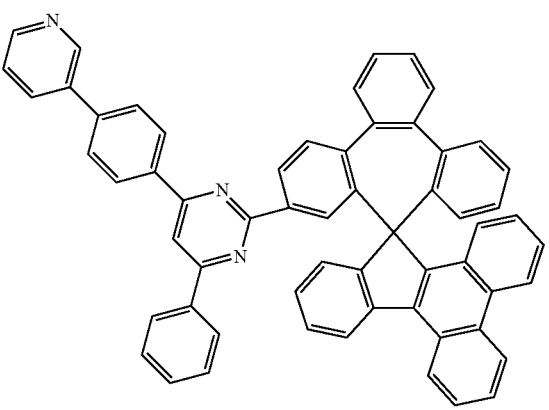

Compound XC
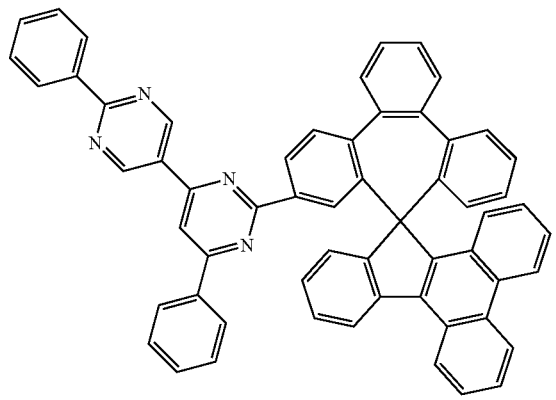
Compound XCI
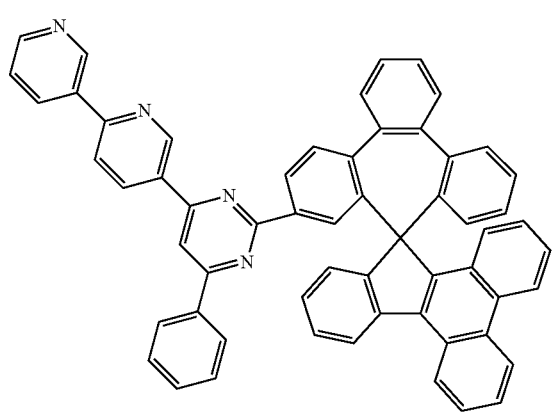
Compound XCII
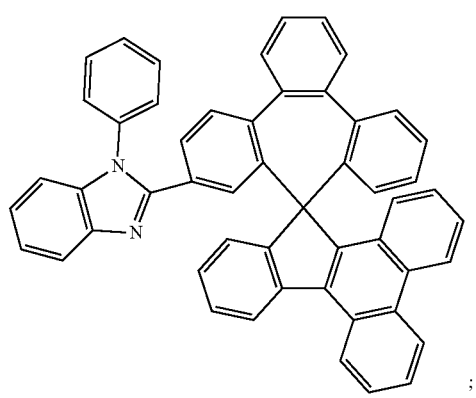
Compound XCIII
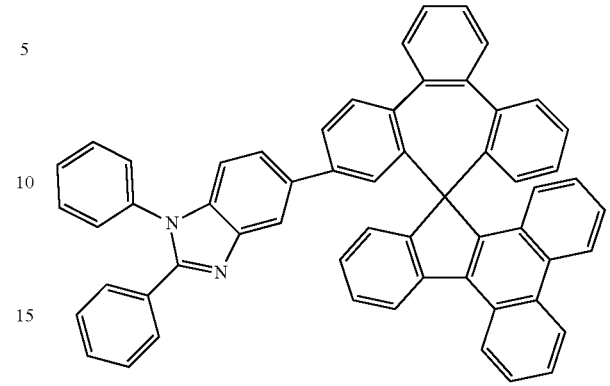
Compound XCIV
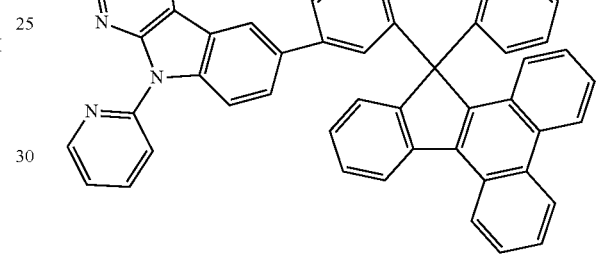
Compound XCV
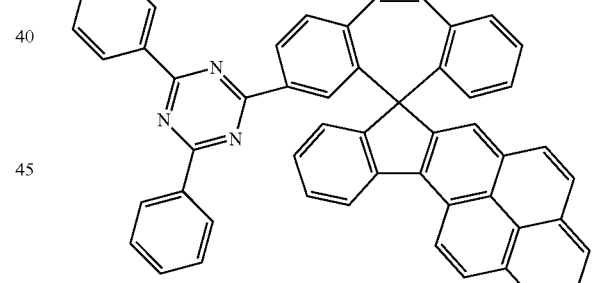
Compound XCVI
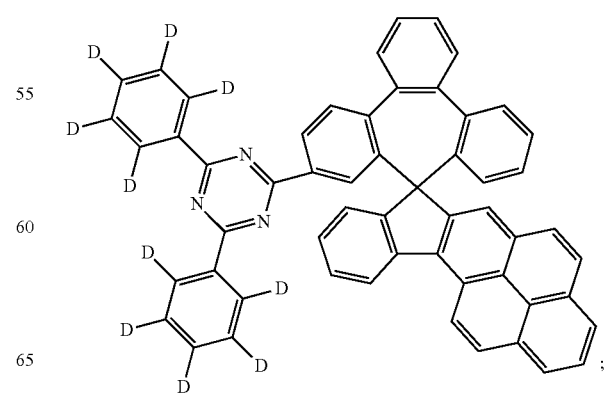

Compound XCVII
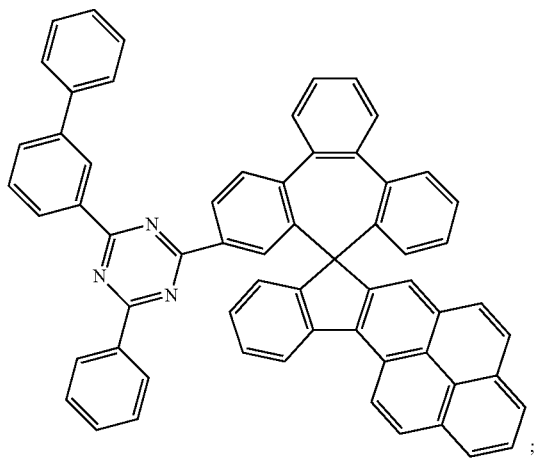
Compound XCVIII
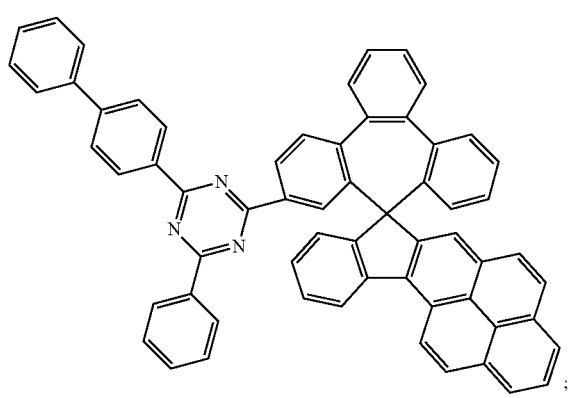
Compound IC
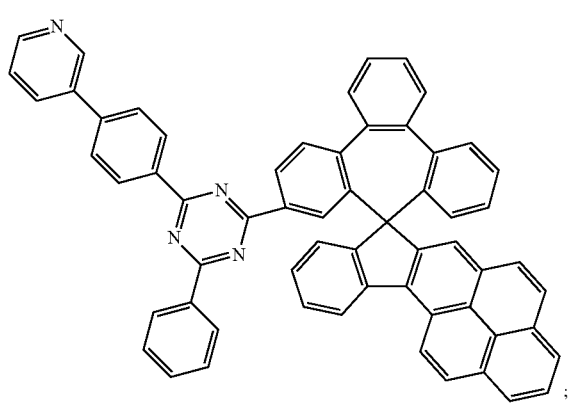
Compound C
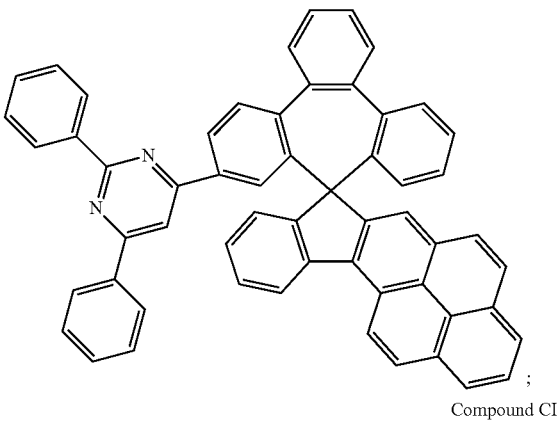
Compound CI
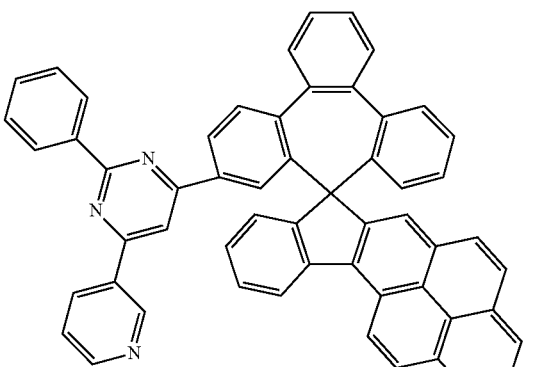
Compound CII
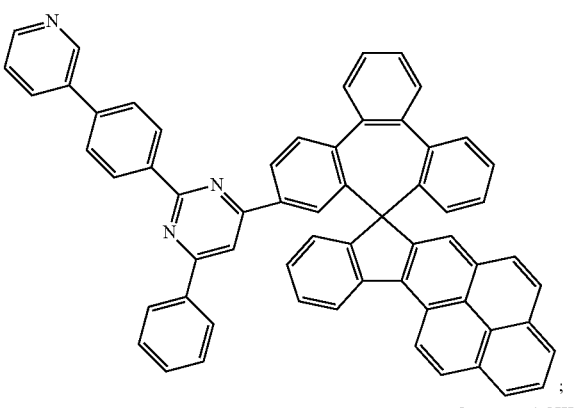
Compound CIII
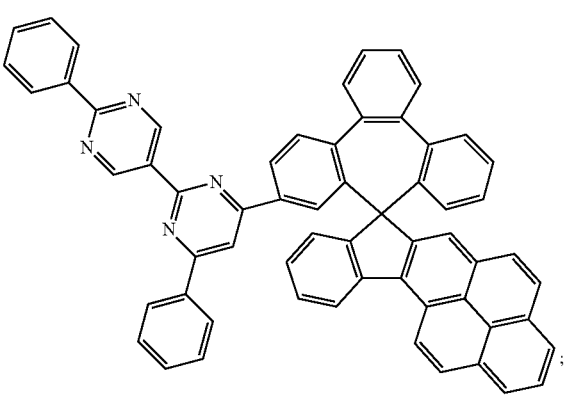

Compound CIV
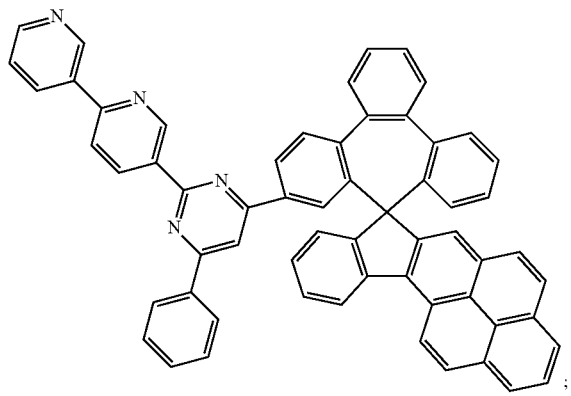
Compound CV
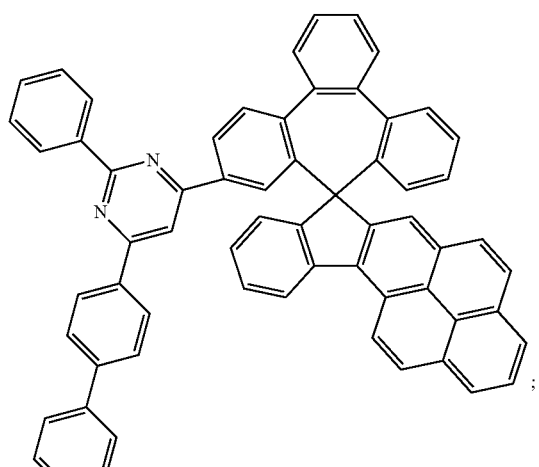
Compound CVI
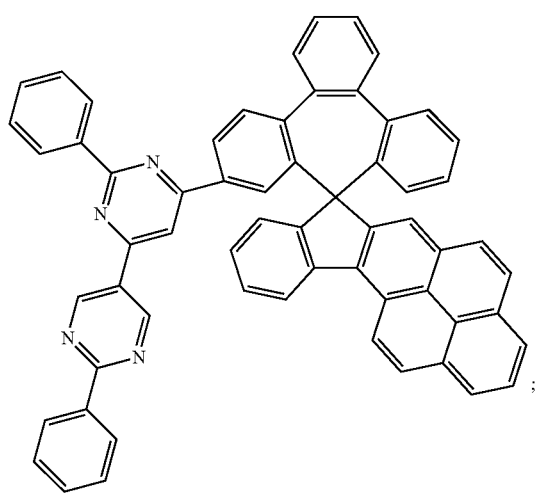
Compound CVII
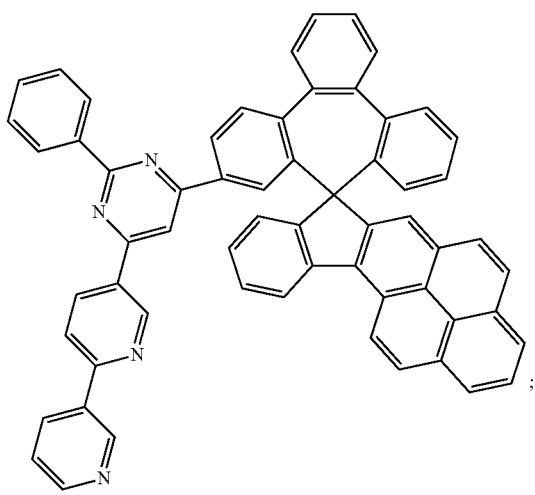
Compound CVIII
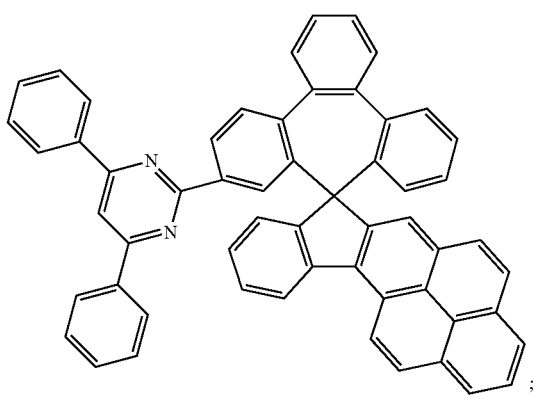
Compound CVIX
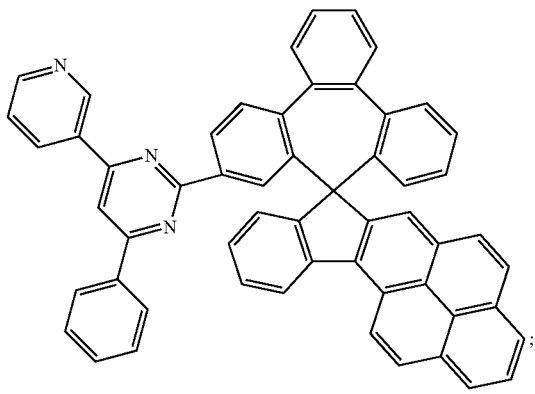

-continued
Compound CX
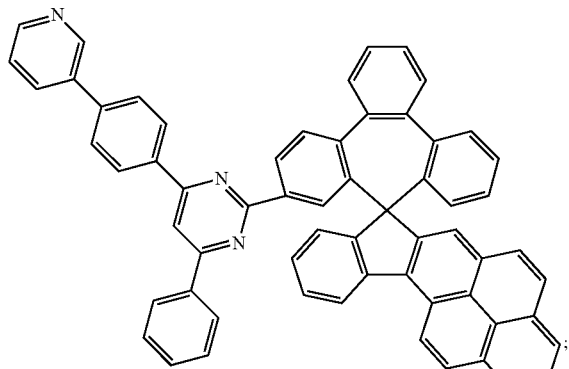
Compound CXI
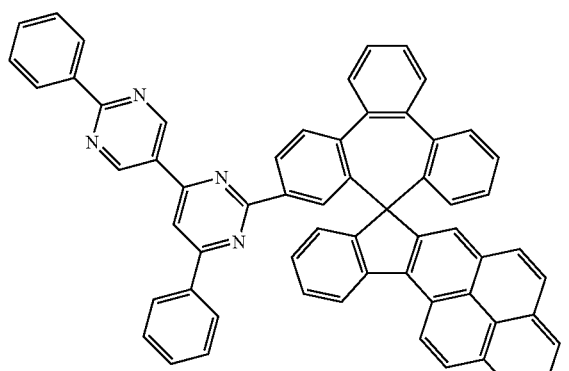
Compound CXII
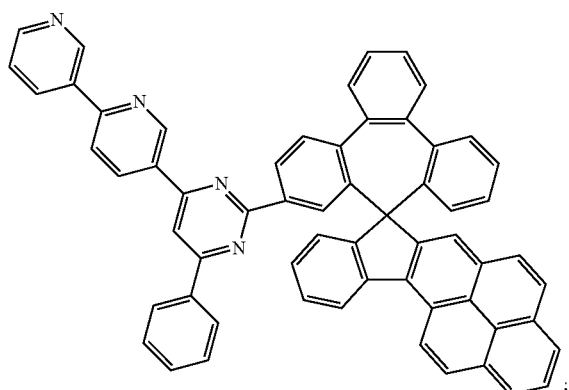
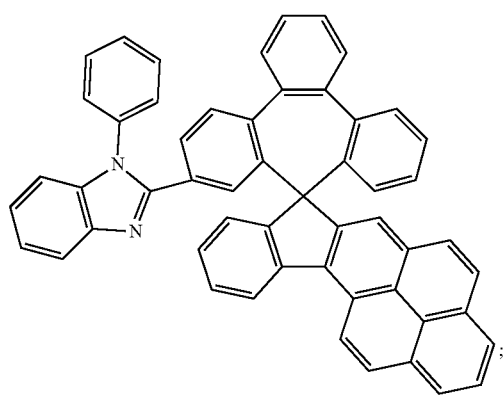
Compound CXIV
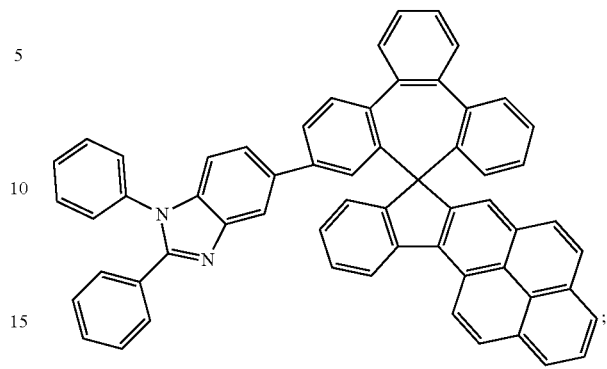
Compound CXV
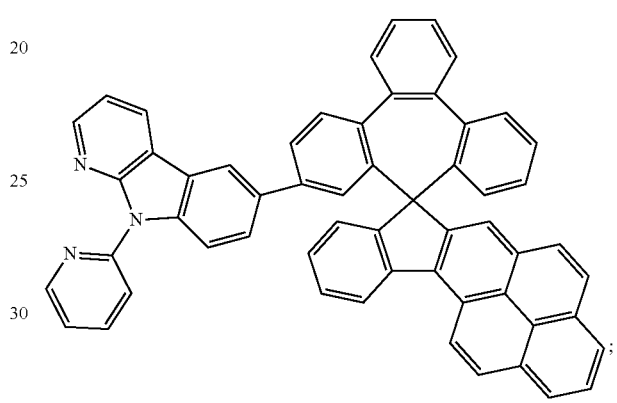
Compound CXVI
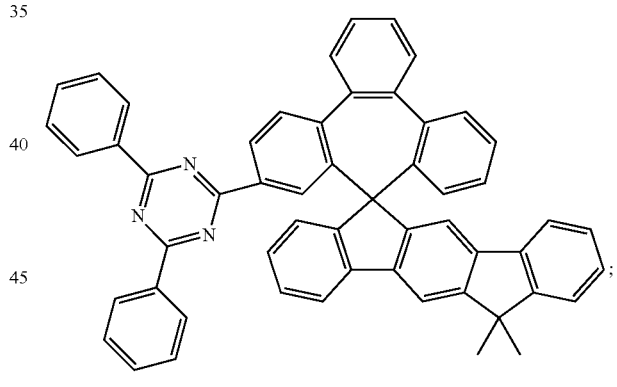
Compound CXVII
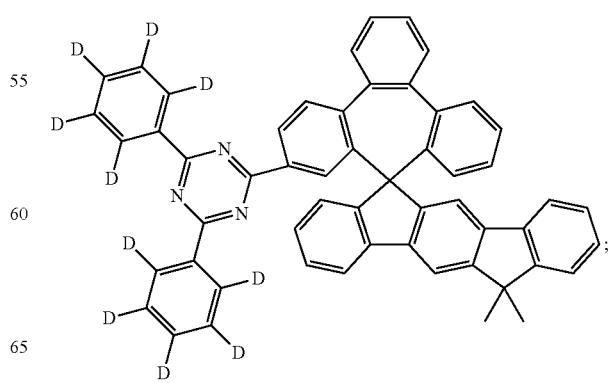

Compound CXVIII
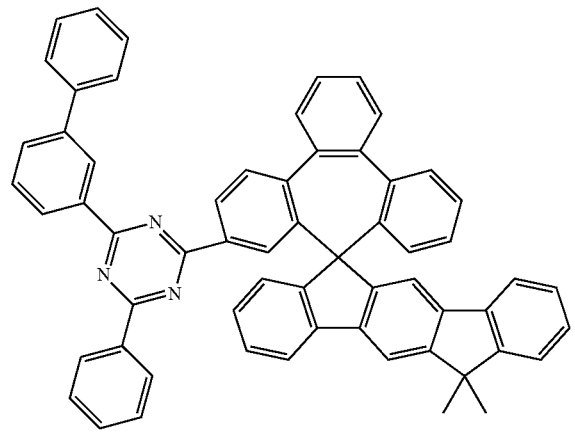
Compound CXIX
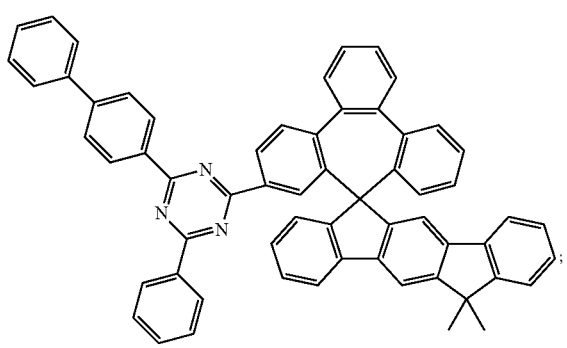
Compound CXX
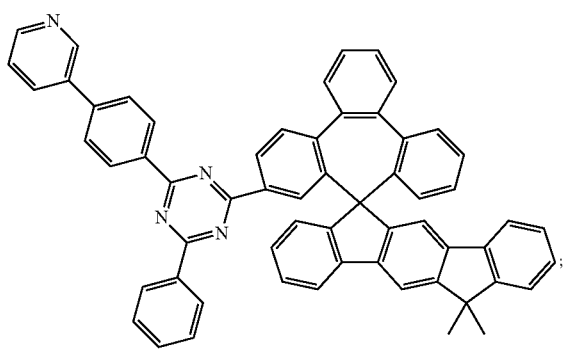
Compound CXXI
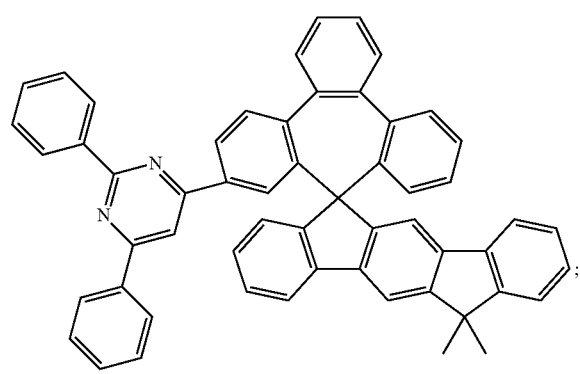
Compound CXXII
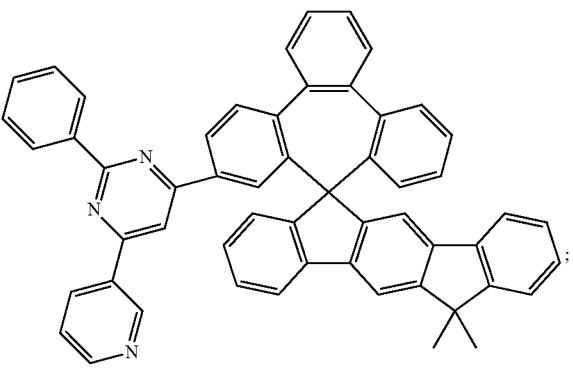
Compound CXXIII
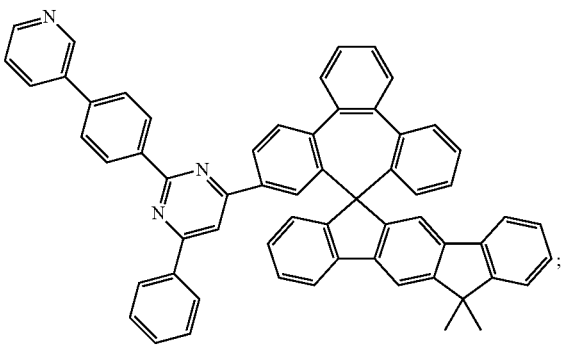
Compound CXXIV
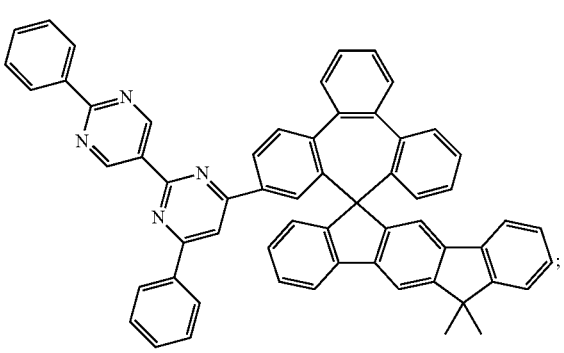
Compound CXXV
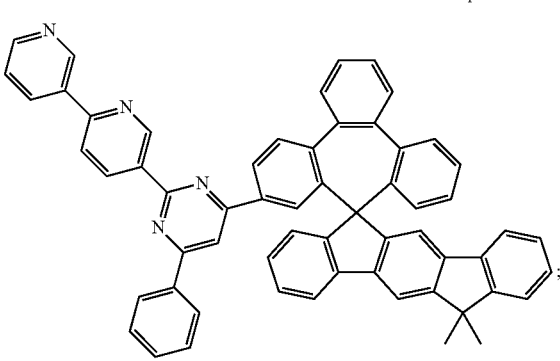

Compound CXXVI
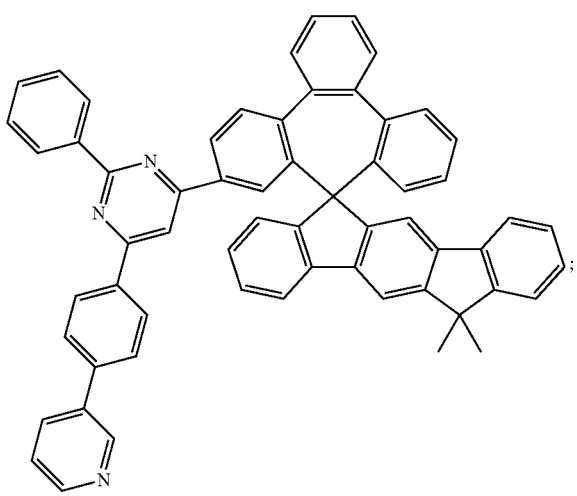
Compound CXXVII
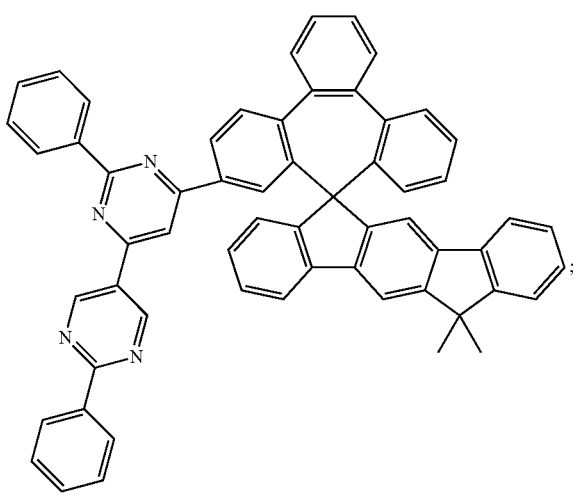
Compound CXXVIII
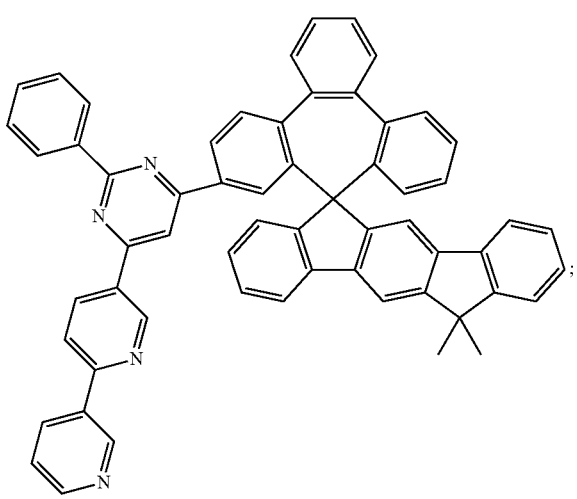
Compound CXXIX
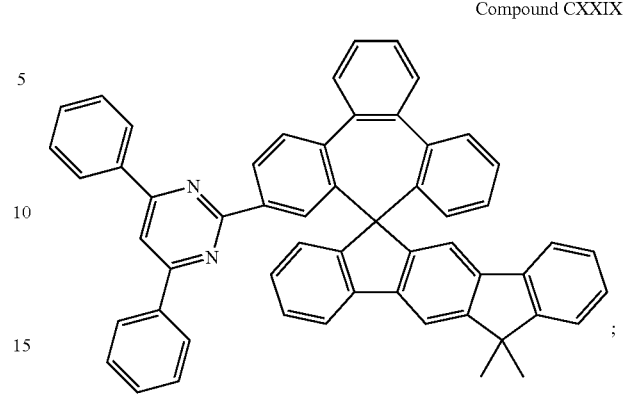
Compound CXXX
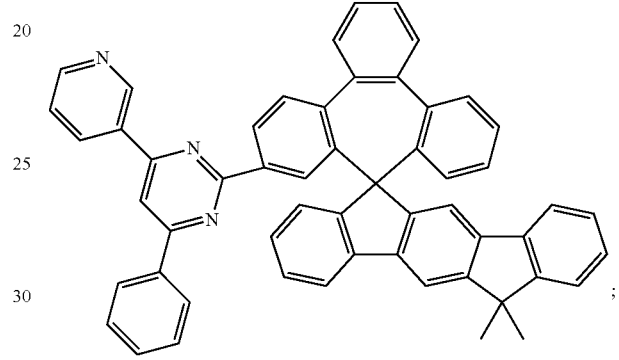
Compound CXXXI
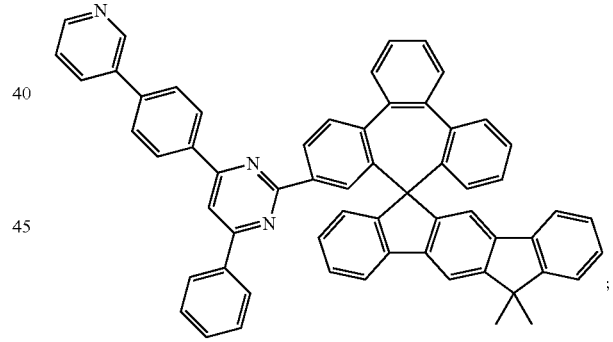
Compound CXXXII
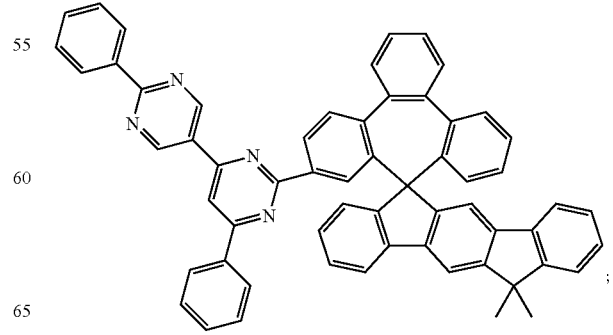

-continued

Compound CXXXIII

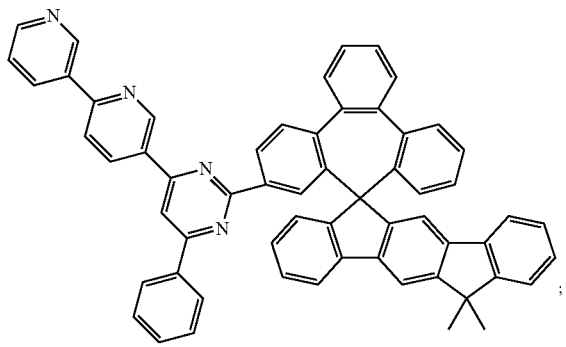

Compound CXXXIV

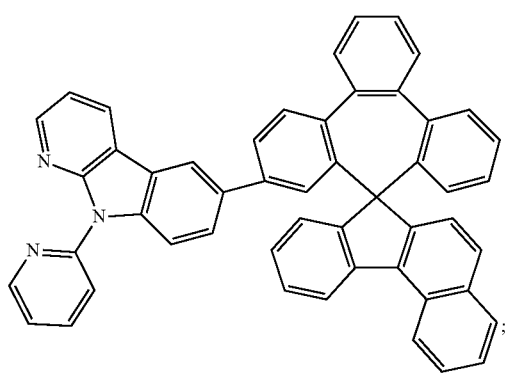

Compound CXXXV

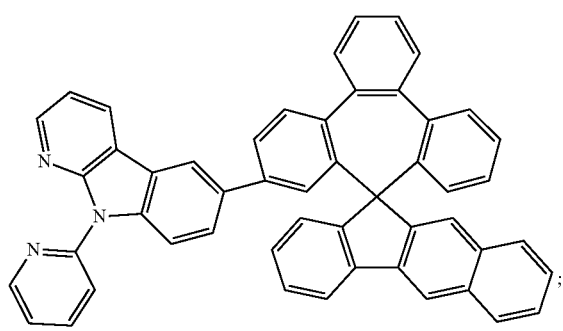

Compound CXXXVI

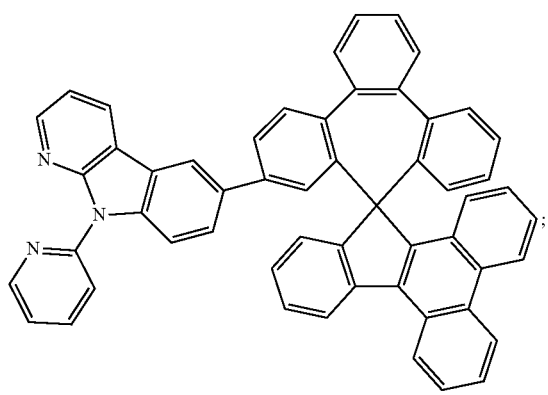

-continued

Compound CXXXVII

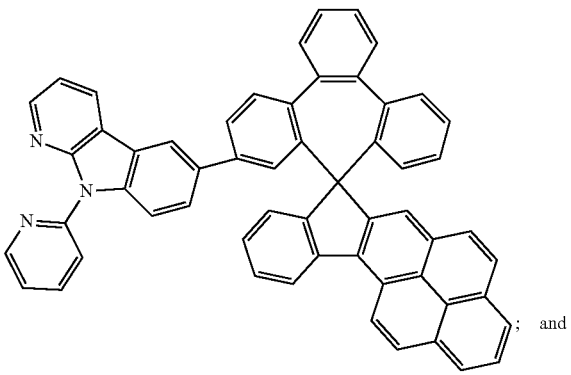

and

Compound CXXXVIII

The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as an electron transport material, an electron injection layer, or a hole blocking layer.

Specifically, the organic light emitting device may comprise:
a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

In one embodiment, the organic layer may be the electron transport layer, i.e., the electron transport layer comprises the novel compound as stated above.

Preferably, the hole injection layer may be a two-layered structure, i.e., the OLED comprises a first hole injection layer and a second hole injection layer disposed between the first electrode and the hole transport layer.

Preferably, the hole transport layer may be a two-layered structure, i.e., the OLED comprises a first hole transport layer and a second hole transport layer disposed between the two-layered hole injection layer and the emission layer.

Preferably, the electron transport layer is made of the novel compound such as Compounds I to CXXXVIII. The OLEDs using the novel compound as the electron transport material can have an improved efficiency compared to commercial OLEDs using known electron transport material, such as 2-(4-(9,10-di(naphthalen-2-yl)anthracen-2-yl)phenyl)-1-phenyl-1H-benzo[d]imidazole; bis(2-methyl-8-quinolinolato)(p-phenylphenolato) aluminum; and 2-(4-biphenylyl)-5-(4-tert-butylphenyl)-1,3,4-oxadiazole (PBD), as the electron transport material.

Preferably, the OLED comprises a hole blocking layer formed between the electron transport layer and the emission layer, to block holes overflow from the emission layer to the electron transport layer. Said hole blocking layer may be made of the foresaid novel compound, 2,9-dimethyl-4,7-diphenyl-1,10-phenanthroline (BCP) or 2,3,5,6-tetramethyl-phenyl-1,4-(bis-phthalimide) (TMPP), but not limited thereto. In another embodiment, the organic layer may be the hole blocking layer, i.e., the hole blocking layer comprises the novel compound as stated above.

Preferably, the OLED comprises electron blocking layer formed between the hole transport layer and the emission layer, to block electrons overflow from the emission layer to the hole transport layer. Said electron blocking layer may be made of 9,9'-[1,1'-biphenyl]-4,4'-diylbis-9H-carbazole (CBP) or 4,4',4''-tri(N-carbazolyl)-triphenylamine (TCTA), but not limited thereto.

In the presence of such a hole blocking layer and/or an electron blocking layer in an OLED, the OLED has a higher luminous efficiency compared to a typical OLED.

Said first and second hole transport layers may be made of, for example, but not limited to: $N^1,N^{1'}$-biphenyl-4,4'-diyl)bis($N^1$-(naphthalen-1-yl)-$N^4,N^{4'}$-diphenylbenzene-1,4diamine); or $N^4,N^{4'}$-di(naphthalen-1-yl)-$N^4,N^{4'}$-diphenylbiphenyl-4,4'-diamine (NPB).

Said first and second hole injection layers may be made of, for example, but not limited to, polyaniline or polyethylenedioxythiophene.

Said emission layer can be made of an emission material including a host and a dopant. The host of the emission material is, for example, but not limited to, 9-(4-(naphthalen-1-yl)phenyl)-10-(naphthalen-2-yl) anthracene.

For red OLEDs, the dopant of the emission material is, for example, but not limited to: organometallic compounds of iridium (II) having perylene ligands, fluoranthene ligands or periflanthene ligands. For green OLEDs, the dopant of the emission material is, for example, but not limited to: diaminofluorenes; diaminoanthracenes; organometallic compounds of iridium (II) having phenylpyridine ligands. For blue OLEDs, the dopant of the emission material is, for example, but not limited to: diaminofluorenes; diaminoanthracenes; diaminopyrenes; or organiemetallic compounds of iridium (II) having phenylpyridine ligands. With various host materials of the emission layer, the OLED can emit lights in red, green or blue.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
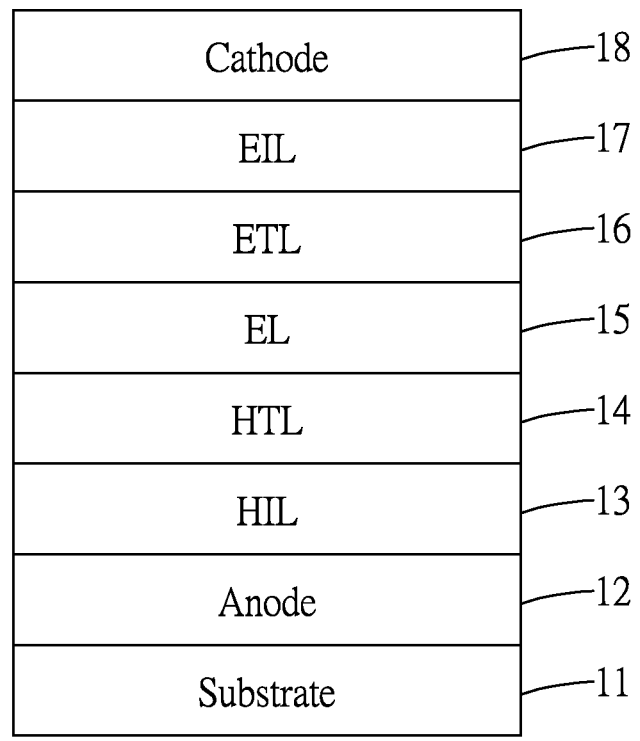
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of Intermediate A1

Intermediate A1 used for preparing a novel compound was synthesized by the following steps. The synthesis pathway of the Intermediate A1 was summarized in Scheme A1.

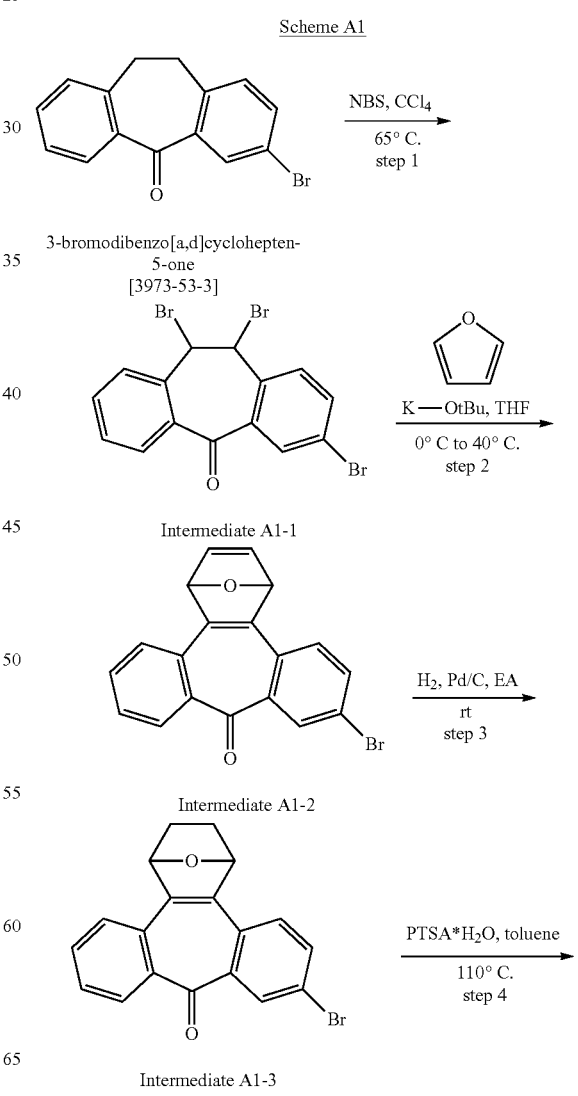

Scheme A1

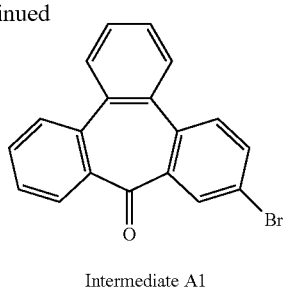

Intermediate A1

Step 1: Synthesis of Intermediate A1-1

A mixture of 3-bromodibenzo[a,d]cyclohepten-5-one (86 g, 1.0 eq). N-bromosuccinimide (NBS) (106 g, 2 eq). benzyl peroxide (0.7 g, 0.01 eq) in carbon tetrachloride ($CCl_4$) (430 ml) was heated to 85° C. The reaction was monitored by high performance liquid chromatography (HPLC). After completion of a reaction, the precipitate was separated by filtration and washed with $CH_3OH$ and then purified by recrystalization. The purified product was concentrated to dryness, whereby a white solid product was obtained in an amount of 123 g and a yield of 92.3%.

The solid product was identified as Intermediate A1-1 by a field desorption mass spectroscopy (FD-MS) analysis. PD-MS analysis: $C_{15}H_9Br_3O$: theoretical value of 444.94 and observed value of 444.94.

Step 2: Synthesis of Intermediate A1-2

The obtained Intermediate A1-1 (116.0 g, 1.0 eq) was dissolved in 960 ml of furan/THF(v/v=2/1), and the reaction was cooled to 0° C. and then treated with potassium tert-butoxide (K-OtBu) (87.8 g, 3.0 eq). The reaction was allowed to stir at 0° C. for hour, and then stirred at room temperature for another 12 hours. Quenched by DI water, the organic layer was recovered by solvent extraction operation and dried over sodium sulfate. The solvent was removed from the organic layer by distillation under reduced pressure, and the resulting residue was purified by silica gel column chromatography. The purified product was concentrated to dryness, whereby a light yellow solid product was obtained in an amount of 46.8 g and a yield of 51.1%.

The solid product was identified as Intermediate A1-2 by FD-MS analysis. FD-MS analysis $C_{19}H_{11}BrO_2$: theoretical value of 351.19 and observed value of 351.19.

Step 3: Synthesis of Intermediate A1-3

A suspension of Intermediate A1-2 (53.5 g, 1.0 eq) and 5% Pd/C (8.1 g, 0.025 eq) in 535 ml of ethyl acetate (EA) was stirred for 3 hours to 6 hours under a hydrogen atmosphere ($H_2$) provided by a balloon of hydrogen. The resulting mixture was filtered through a pad of celite and washed with EA, and the filtrate was concentrated under reduced pressure to obtain 100 g (100%) of yellow solid product.

The solid product was identified as Intermediate A1-3 by FD-MS analysis. FD-MS analysis $C_{19}H_{13}BrO_2$: theoretical value of 353.21 and observed value of 353.21. The intermediate A1-3 can be directly used in the following step without further purification.

Step 4: Synthesis of Intermediate A1-4

Intermediate A1-3 (53 g, 1.0 eq) and p-toluenesulfonic acid (PTSA) (57 g, 2.0 eq) in 530 ml of toluene was heated to reflux for 12 hours. The reaction mixture was cooled to room temperature and then quenched with a saturated aqueous solution of $NaHCO_3$ and extracted with $CH_2Cl_2$. The organic layer was washed with water, brine and dried with anhydrous $Na_2SO_4$ subsequently. Then the resulting solution was concentrated under reduced pressure and purified by column chromatography on silica gel with $CH_2Cl_2$/hexane 1/1 (v/v) as eluent, whereby a light yellow solid product was obtained in an amount of 46.0 g and a yield of 91.5%.

The solid product was identified as Intermediate A1 by FD-MS analysis. FD-MS analysis $C_{19}H_{11}BrO$: theoretical value of 335.19 and observed value of 335.19.

Synthesis of Intermediate A2

Intermediate A2 used for preparing a novel compound was synthesized in a similar manner as Intermediate A1 through steps 1 to 4, except that the starting material 3-bromodibenzo[a,d]cyclohepten-5-one was replaced by 2-bromodibenzo[a,d]cyclohepten-5-one (CAS No. 198707-82-3). The synthesis pathway of Intermediate A2 was summarized in Scheme A2. All intermediates were analyzed according to the methods as described above, and the results were listed in Table 1.

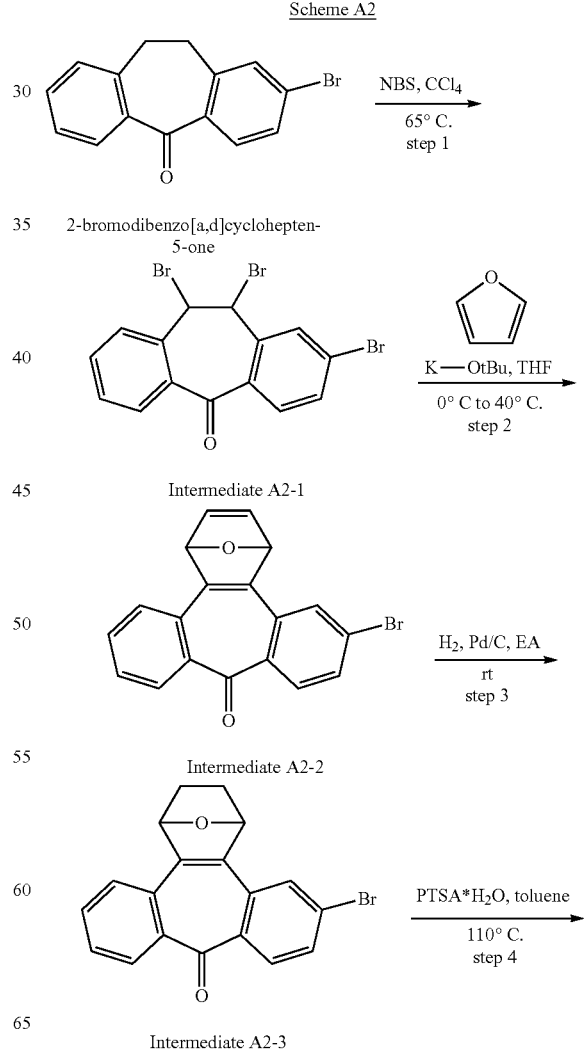

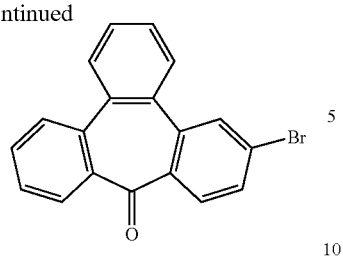

Intermediate A2

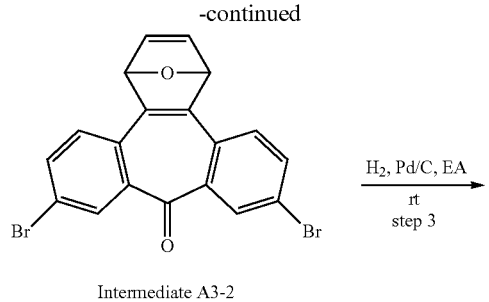

Intermediate A3-2

Synthesis of Intermediate A3

Intermediate A3 used for preparing a novel compound was synthesized in a similar manner as Intermediate A1 through steps 1 to 4 except that the starting material 3-bromodibenzo[a,d]cyclohepten-5-one was replaced by 3,7-dihromodibenzo[a,d]cyclohepten-5-one (CAS No. 226946-20-9). The synthesis pathway of Intermediate A3 was summarized in Scheme A3. All intermediates were analyzed as described above, and the results were listed in Table 1.

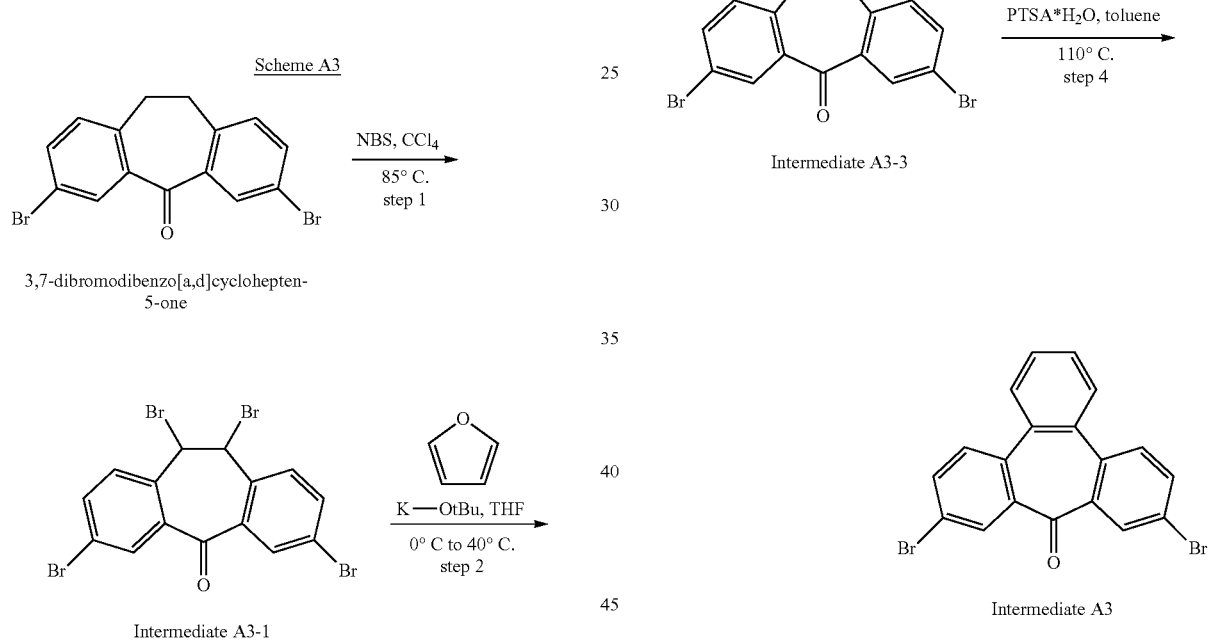

TABLE 1

| chemical structures, yields, formulae, and mass (M⁺) analyzed by FD-MS of intermediates. | | | | |
|---|---|---|---|---|
| Intermediate | A1-1 | A1-2 | A1-3 | A1 |
| Chemical Structure | (structure) | (structure) | (structure) | (structure) |
| Yield | 92.3% | 60.3% | NA | 91.5% |
| Formula | $C_{15}H_9Br_3O$ | $C_{19}H_{11}BrO_2$ | $C_{19}H_{13}BrO_2$ | $C_{19}H_{11}BrO$ |
| Mass(M⁺) | 444.94 | 351.19 | 353.21 | 335.19 |

TABLE 1-continued chemical structures, yields, formulae, and mass (M⁺) analyzed by FD-MS of intermediates.

| Intermediate | A2-1 | A2-2 | A2-3 | A2 |
|---|---|---|---|---|
| Chemical Structure | (structure) | (structure) | (structure) | (structure) |
| Yield | 91.5% | 58.2% | NA | 93.5% |
| Formula | $C_{15}H_9Br_3O$ | $C_{19}H_{11}BrO_2$ | $C_{19}H_{13}BrO_2$ | $C_{19}H_{11}BrO$ |
| Mass(M⁺) | 444.94 | 351.19 | 353.21 | 335.19 |
| Intermediate | A3-1 | A3-2 | A3-3 | A3 |
| Chemical Structure | (structure) | (structure) | (structure) | (structure) |
| Yield | 93.7% | 75.8% | NA | 93.0% |
| Formula | $C_{15}H_8Br_4O$ | $C_{19}H_{10}Br_2O_2$ | $C_{19}H_{12}Br_2O_2$ | $C_{19}H_{10}Br_2O$ |
| Mass(M⁺) | 523.84 | 430.09 | 432.11 | 414.09 |

Modifications of Intermediates A1 to A3

In addition to the Intermediates A1 to 3, one person skilled in the art can adopt other starting materials and successfully synthesize other desired intermediates through a reaction mechanism similar to Scheme A1 to A3. Applicable modifications of Intermediates A1 to A3 may be for example, but not limited to, Intermediates A4 to A15 as follows.

Intermediate A4

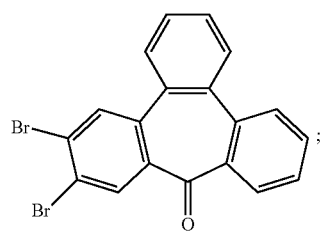

Intermediate A5

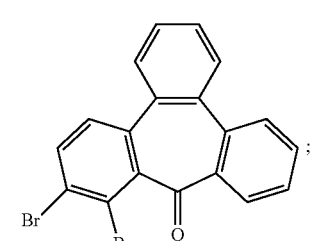

Intermediate A6

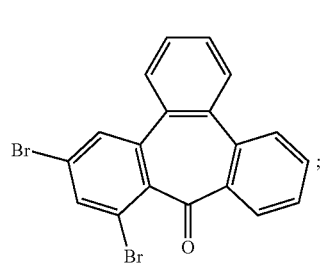

Intermediate A7

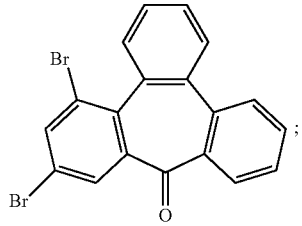

Intermediate A8

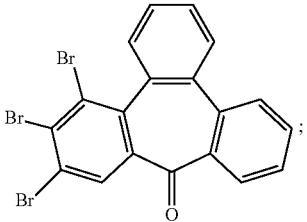

Intermediate A9

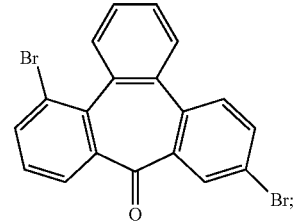

Intermediate A10

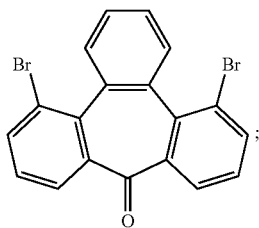

Intermediate A11

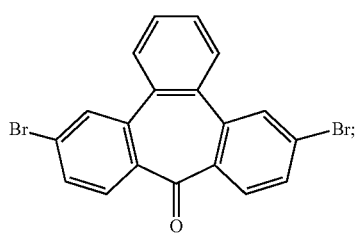

Intermediate A12

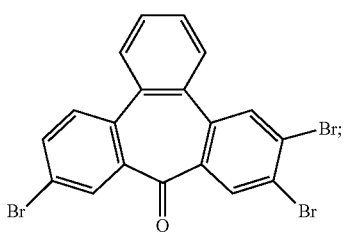

Intermediate A13

Intermediate A14

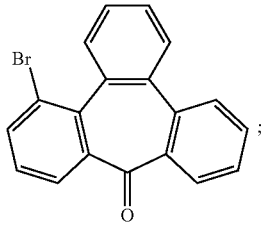

Intermediate A15

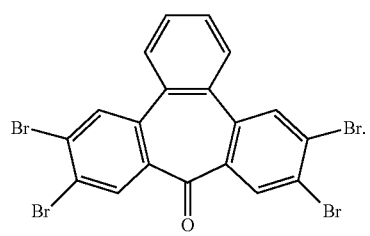

Synthesis of Intermediates b1 to B4 and B6

Intermediates B1 to B4 and B6 were synthesized by reacting 1-bromo-2-iodobenzene and aryl boronic acid (Reagent A). A general synthesis pathway for Intermediate Bn was summarized in Scheme B1. In the following Scheme B1 "Reactant A" may be an one of Reactants A1 to A4 and A6 as listed in Table 2, and "Intermediate Bn" ma be an one of foresaid Intermediates B1 to B4 and B6.

Scheme B1

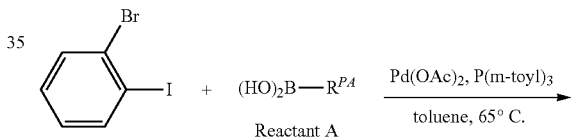

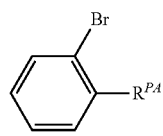

$R^{PA}$: polycyclic aromatic group

Intermediate Bn

According to the Scheme B1, each of the Intermediates B1 to B4 and B6 was synthesized by the steps as follows.

1-bromo-2-iodobenzene (1.0 eq), Reactant A (1.2 eq), potassium carbonate (3.0 eq), 200 ml of toluene, tri(m-tolyl) phosphine (P(m-toyl)₃) (0.06 eq) and Pd(OAc)₂ (0.015 eq) were mixed and stirred at 80° C. for 12 hours. The reaction mixture was then cooled to room temperature, and an organic layer was extracted with saturated aqueous solution of sodium chloride and EA and dried over magnesium sulfate, and then treated with activated charcoal, followed by filtering with silica gel. After a solid prepared by concentrating the filtrate under reduced pressure was suspended in hexane, the suspension was filtered again and washed with hexane to obtain Intermediate Bn. All intermediates were analyzed according to the methods as described above, and the results were listed in Table 2.

TABLE 2

Reactant A used for preparing Intermediates B1 to B4 and B6, and the chemical structures, yields, formulae, and mass analyzed by FD-MS of Intermediates B1 to B4 and B6.

| Reactant A Chemical Structure | Intermediate Bn Chemical Structure | Yield (%) | Formula/ Mass (M+) |
|---|---|---|---|
| 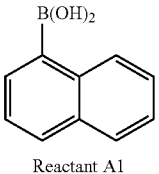 Reactant A1 | 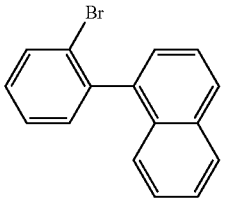 Intermediate B1 | 91.0 | $C_{16}H_{11}Br$/ 283.16 |
| 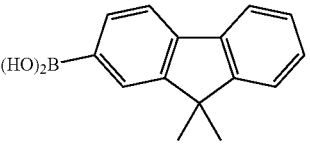 Reactant A2 | 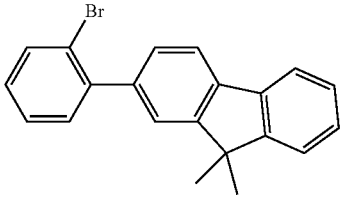 Intermediate B2 | 90.7 | $C_{21}H_{17}Br$/ 349.26 |
| 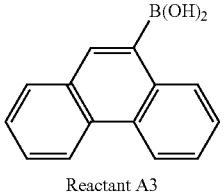 Reactant A3 | 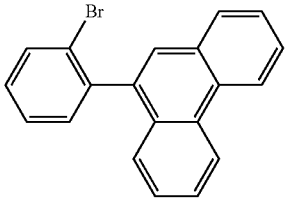 Intermediate B3 | 90.2 | $C_{20}H_{13}Br$/ 333.22 |
| 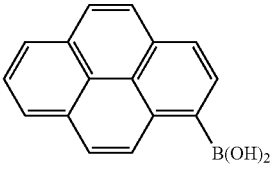 Reactant A4 | 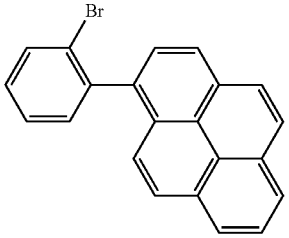 Intermediate B4 | 86.5 | $C_{22}H_{13}Br$/ 357.24 |
| 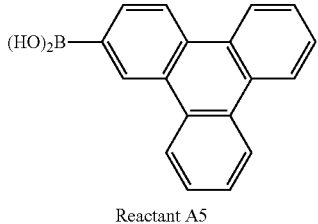 Reactant A5 | 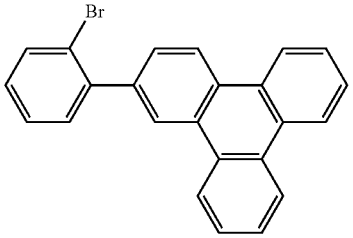 Intermediate B6 | 80 | $C_{24}H_{15}Br$/ 383.28 |

Synthesis of Intermediates B5

In addition to Scheme B1, another synthesis pathway for Intermediate B5 was summarized in Scheme B2.

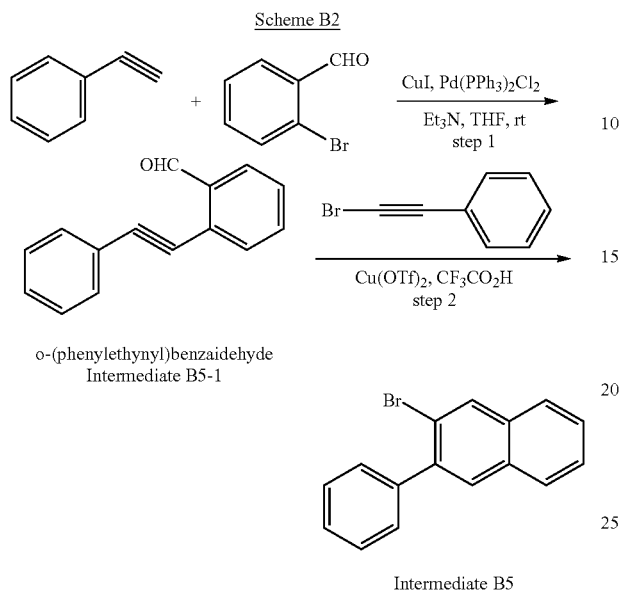

Scheme B2 o-(phenylethynyl)benzaidehyde
Intermediate B5-1

Intermediate B5

Step 1: Synthesis of Intermediate B5-1

A mixture of dichloro bis-(triphenylphosphine) palladium (0.05 eq) and 2-bromobenzaldehyde (1 eq) in THF (0.13 to 0.15 M) was added with triethylamine (3.0 eq). After being stirred for 10 min at room temperature, phenyl acetylene (1.5 eq) and copper iodide (0.05 eq) were added to the mixture. The resulting mixture was stirred at room temperature for 24 h. The reaction mixture was quenched with saturated aqueous of $NH_4Cl$, extracted with EtOAc three times, and washed with brine. The organic layers were dried over $Na_2SO_4$ and concentrated under a reduced pressure after filtration. The crude mixture was purified by silica-gel column chromatography to obtain Intermediate B5-1 in a yield of 92.4%. The product was identified as Intermediate B5-1 by FD-MS analysis. FD-MS analysis: $C_{15}H_{10}O$: theoretical value of 206.64 and observed value of 206.64.

Step 2: Synthesis of Intermediate B5

A mixture of intermediate B5-1 (1.0 eq) and $Cu(OTf)_2$ (0.05 eq) in 1,2-dichloroethane (5 times of Intermediate B5-1) were added with 1-(2-bromoethynyl)benzene(1.2 eq) and $CF_3CO_2H$ (1.0 eq) successively at room temperature under argon atmosphere. The resulting mixture was stirred at 100° C. for 15 min and then cooled to room temperature. A saturated aqueous solution of $NaHCO_3$ was added, and the mixture was extracted with ether three times. The combined extracts were washed with brine, dried over $MgSO_4$, and evaporated to leave the crude product. The crude product was then purified by silica gel column chromatography using hexane as an eluent to give Intermediate B5 (yield 80%). The product was identified as intermediate B5 by FD-MS analysis. FD-MS analysis: $C_{16}H_{11}Br$: theoretical value of 283.16 and observed value of 283.16.

Modifications of Intermediates B1 to B6

In addition to the Intermediates B1 to B6, one person skilled in the art can adopt any dihalobenzenes other than 1-bromo-2-iodobenzene and any aryl boronic acids other than Reactants A1 to A5 to successfully synthesize other desired Intermediates Bn through a reaction mechanism similar to Scheme B1. Moreover, one person skilled in the art also can adopt any halo-aromatic aldehyde other than 2-bromobenzaldehyde and any aromatic alkyne other than ethynylbenzene to successfully synthesize other desired Intermediates Bn through a reaction mechanism similar to Scheme B2. Applicable modifications of Intermediates B1 to B6 may be, for example, but not limited to, Intermediates B7 and B14 as follows.

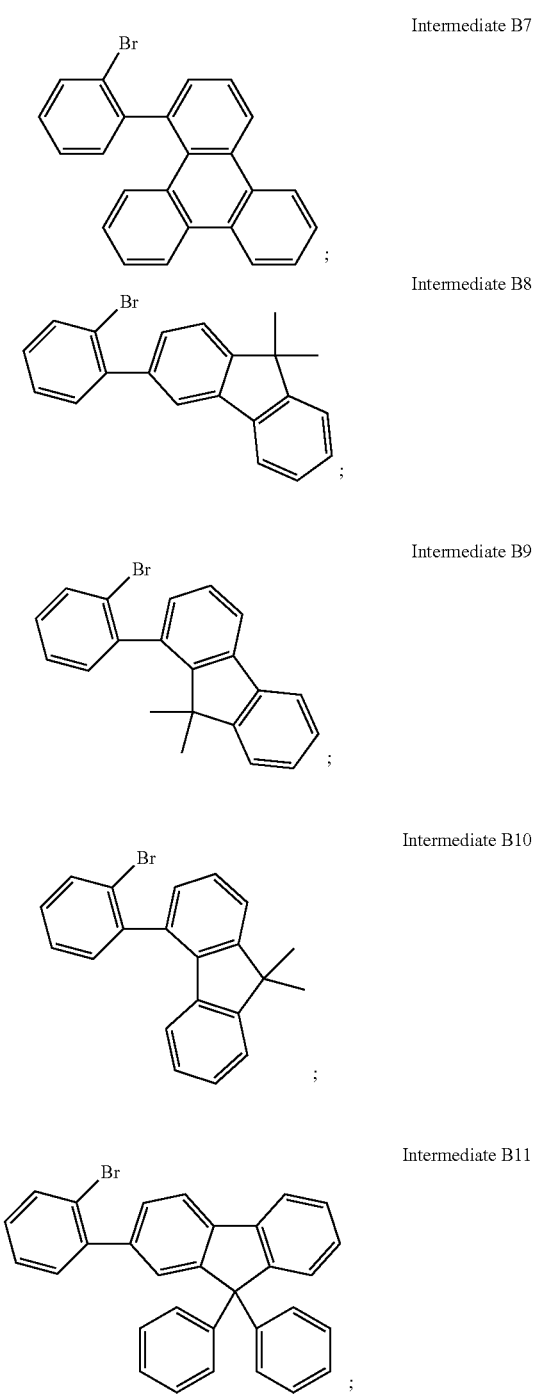

Intermediate B7

Intermediate B8

Intermediate B9

Intermediate B10

Intermediate B11

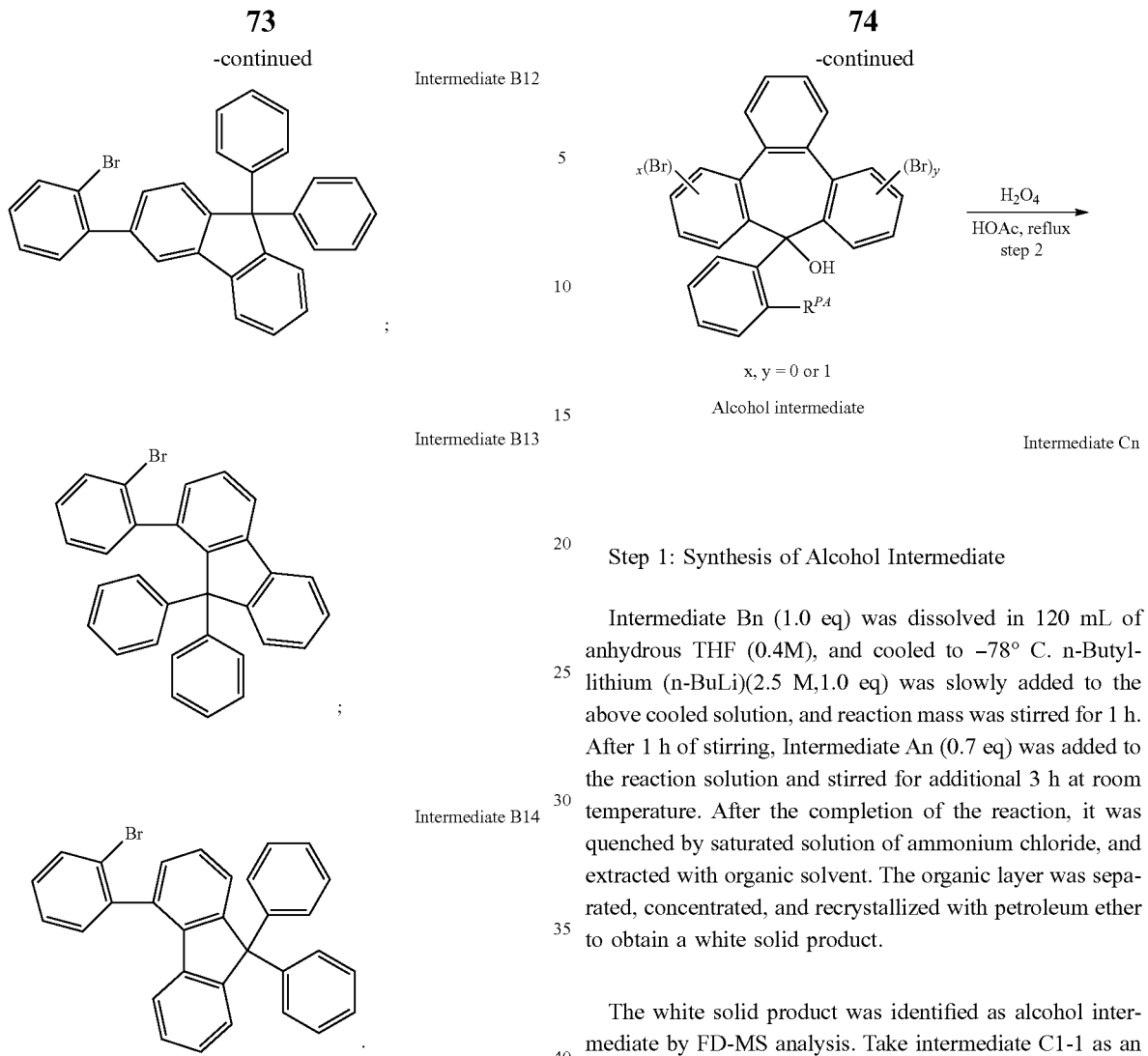

Synthesis of Intermediates Cn

The foresaid Intermediates B1 to B14, especially the foresaid Intermediates B1 to B5 were further adopted to synthesize Intermediate Cn. A general synthesis pathway for Intermediate Cn was summarized in Scheme C. In the following Scheme C1, "Intermediate An" may be any one of foresaid Intermediates A1 to A15 or the like, "Intermediate Bn" may be any one of foresaid Intermediates B1 to B14 or the like, and "Intermediate Cn" may be any one of Intermediates C1 to C11 as listed in Table 3-1 or the like. Intermediates C1 to C11 were each synthesized by the following steps.

Scheme C1

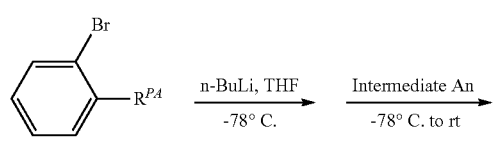

$R^{PA}$: polycyclic aromatic group
Intermediate Bn

Step 1: Synthesis of Alcohol Intermediate

Intermediate Bn (1.0 eq) was dissolved in 120 mL of anhydrous THF (0.4M), and cooled to −78° C. n-Butyllithium (n-BuLi)(2.5 M,1.0 eq) was slowly added to the above cooled solution, and reaction mass was stirred for 1 h. After 1 h of stirring, Intermediate An (0.7 eq) was added to the reaction solution and stirred for additional 3 h at room temperature. After the completion of the reaction, it was quenched by saturated solution of ammonium chloride, and extracted with organic solvent. The organic layer was separated, concentrated, and recrystallized with petroleum ether to obtain a white solid product.

The white solid product was identified as alcohol intermediate by FD-MS analysis. Take intermediate C1-1 as an example, FD-MS analysis: $C_{37}H_{23}BrO_2$: theoretical value of 579.48 and observed value of 579.48.

The alcohol intermediate could be directly used in step 2 without further purification. Each alcohol intermediate synthesized by reacting different Intermediates An with Intermediates Bn was identified by FD-MS. The chemical structure of each alcohol intermediate was listed in Table 3-1.

Step 2: Synthesis of Intermediate Cn

Alcohol intermediate (1.0 eq), acetic acid (w/v=1/3 to the reactant) and $H_2SO_4$(5 drops) were mixed, and the mixture was stirred at 110° C. for 6 hours. The solvent was then removed under reduced pressure, and the residue was purified with column chromatography. The residual mass was recrystallized with toluene to obtain a white solid product.

The solid product was identified by FD-MS analysis. The chemical structures, yields, formulae, and mass analyzed by FD-MS of Intermediates C1 to C11 were listed in Table 3-1.

TABLE 3-1

Intermediates An and Bn used for preparing Intermediates C1 to C11, chemical structures of alcohol
intermediates, and chemical structures, yields, formulae, and mass analyzed by FD-MS of Intermediates C1 to C11.

| Intermediate An | Intermediate Bn | Alcohol intermediate Chemical Structure | Intermediate Cn Chemical Structure | Yield (%) | Formula/ Mass (M+) |
|---|---|---|---|---|---|
| A1 | B1 | 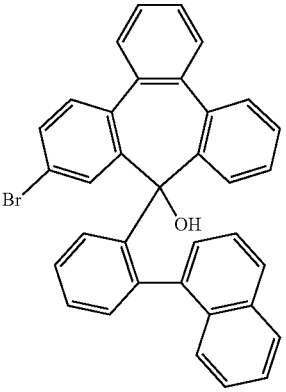<br>Intermediate C1-1 | 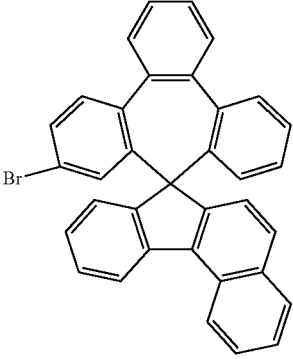<br>Intermediate C1 | 93 | $C_{35}H_{21}Br$/ 521.46 |
| A2 | B1 | 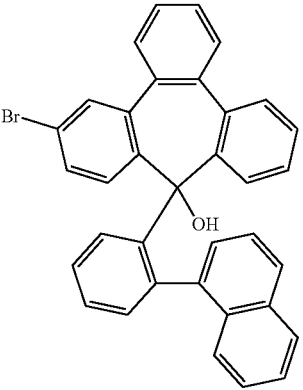<br>Intermediate C2-1 | 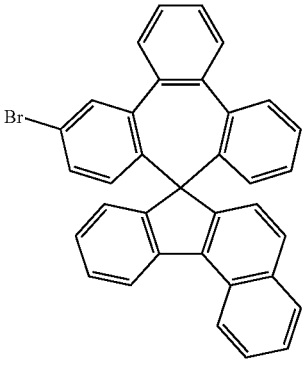<br>Intermediate C2 | 91 | $C_{35}H_{21}Br$/ 521.46 |
| A3 | B1 | 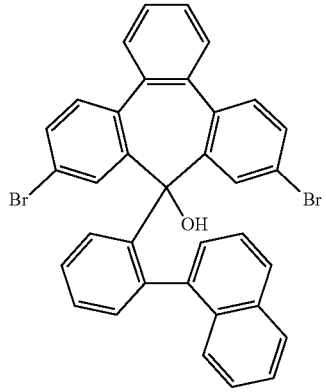<br>Intermediate C3-1 | 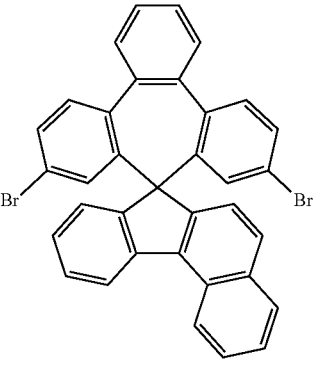<br>Intermediate C3 | 76 | $C_{35}H_{20}Br_2$/ 600.34 |

TABLE 3-1-continued

Intermediates An and Bn used for preparing Intermediates C1 to C11, chemical structures of alcohol
intermediates, and chemical structures, yields, formulae, and mass analyzed by FD-MS of Intermediates C1 to C11.

| Intermediate An | Intermediate Bn | Alcohol intermediate Chemical Structure | Intermediate Cn Chemical Structure | Yield (%) | Formula/ Mass (M+) |
|---|---|---|---|---|---|
| A1 | B5 | Intermediate C4-1 | Intermediate C4 | 81 | $C_{35}H_{21}Br$/ 521.45 |
| A3 | B5 | Intermediate C5-1 | Intermediate C5 | 68 | $C_{35}H_{20}Br_2$/ 600.34 |
| A1 | B2 | Intermediate C6-1 | Intermediate C6 | 87 | $C_{40}H_{27}Br$/ 587.55 |
| A3 | B2 | Intermediate C7-1 | Intermediate C7 | 61 | $C_{40}H_{26}Br_2$/ 666.44 |

TABLE 3-1-continued

Intermediates An and Bn used for preparing Intermediates C1 to C11, chemical structures of alcohol intermediates, and chemical structures, yields, formulae, and mass analyzed by FD-MS of Intermediates C1 to C11.

| Intermediate An | Intermediate Bn | Alcohol intermediate Chemical Structure | Intermediate Cn Chemical Structure | Yield (%) | Formula/ Mass (M+) |
|---|---|---|---|---|---|
| A1 | B3 | Intermediate C8-1 | Intermediate C8 | 83 | $C_{39}H_{23}Br$/ 571.5 |
| A3 | B3 | Intermediate C9-1 | Intermediate C9 | 77 | $C_{39}H_{22}Br_2$/ 650.4 |
| A1 | B4 | Intermediate C10-1 | Intermediate C10 | 95 | $C_{41}H_{23}Br$/ 595.53 |

TABLE 3-1-continued

Intermediates An and Bn used for preparing Intermediates C1 to C11, chemical structures of alcohol intermediates, and chemical structures, yields, formulae, and mass analyzed by FD-MS of Intermediates C1 to C11.

| Intermediate An | Intermediate Bn | Alcohol intermediate Chemical Structure | Intermediate Cn Chemical Structure | Yield (%) | Formula/ Mass (M+) |
|---|---|---|---|---|---|
| A3 | B4 | Intermediate C11-1 | Intermediate C11 | 73 | $C_{41}H_{22}Br_2$/ 674.42 |

Modifications of Intermediates C1 to C11

In addition to the intermediates C1 to C11, one person skilled in the art can adopt any Intermediate An other than Intermediates A1 to A4 anchor any Intermediate Bn other than Intermediates B1 to B5 to successfully synthesize other desired intermediates Cn through a reaction mechanism similar to Scheme C1. Applicable modifications of Intermediates C1 to C11 may be, for example, but not limited to, Intermediates C12 to C23 as follows.

Intermediate C12

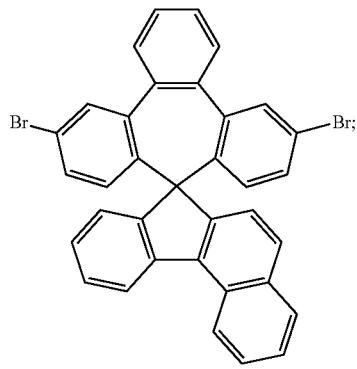

Intermediate C13

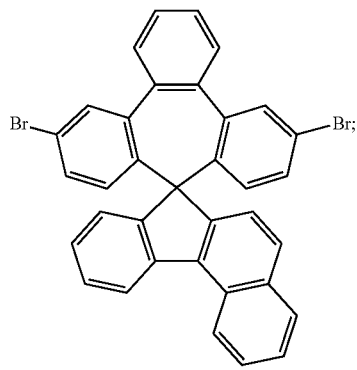

-continued

Intermediate C14

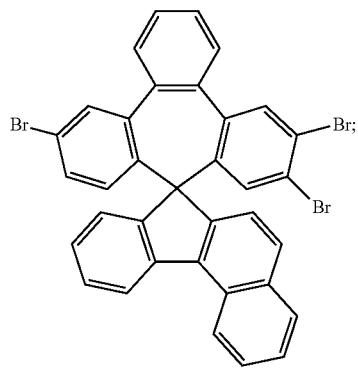

Intermediate C15

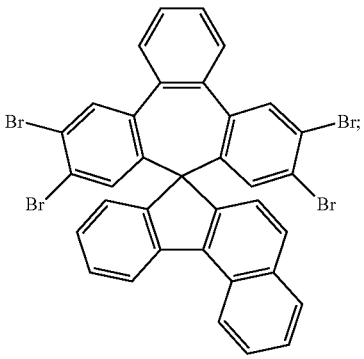

Intermediate C16
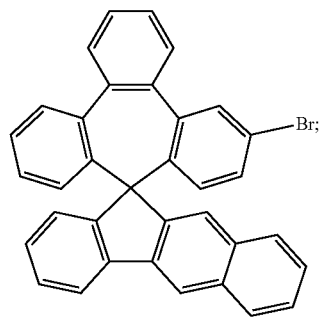
Intermediate C17
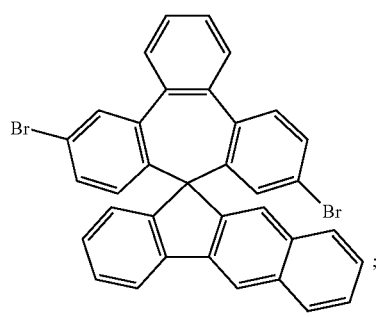
Intermediate C18
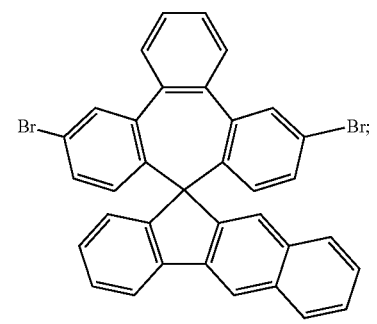
Intermediate C19
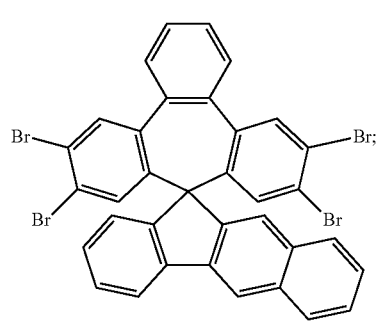
Intermediate C20
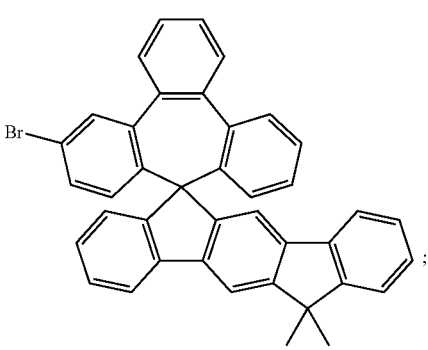
Intermediate C21
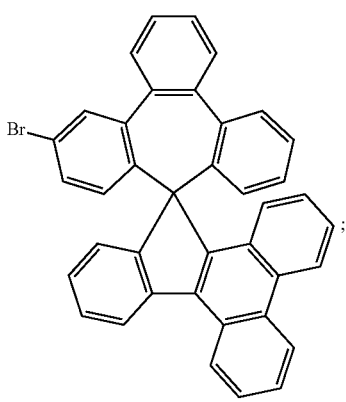
Intermediate C22
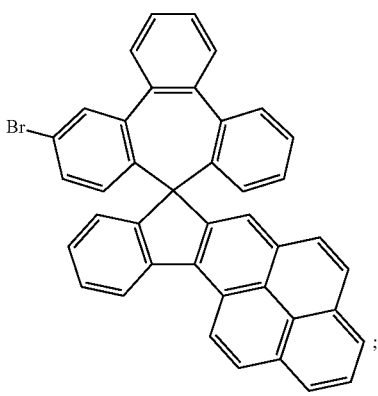
Intermediate C23
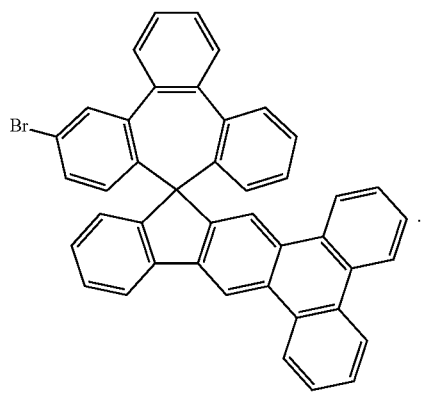

Synthesis of Intermediate Cn-B

The foresaid Intermediate Cn could be further modified into an Intermediate Cn-B through Miyaura borylation reaction. "Intermediate Cn-B" was directed to a compound derived from Intermediate Cn whose bromo group was replaced by (pinacolato)boron group. A synthesis pathway of Intermediate Cn-B was summarized in Scheme C1-B. Intermediate Cn-B was synthesized by the following steps.

Scheme C1-B

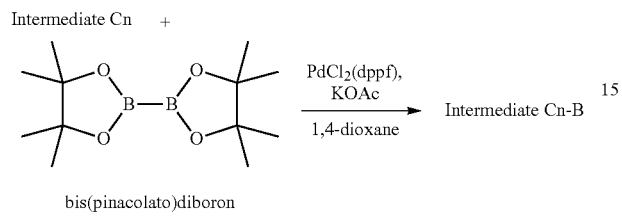

A mixture of bis(pinacolato)diboron (1.2 eq), Intermediate C1 (1.0 eq), 1,1-bis(diphenylphosphino)-ferrocene dichloropalladium II)((PdCl$_2$(dppf)) (0.015 eq) and potassium acetate (KOAc) (3.0 eq) in anhydrous 1,4-dioxane (0.3 M) was stirred at 110° C. for 8 hours under nitrogen atmosphere. After cooling to room temperature, the solvent was then removed under reduced pressure, and the residue was purified via column chromatography to obtain a pale yellow solid product.

The pale yellow solid product was identified by FD-MS analysis. The chemical structures, yields, formulae, and mass analyzed by FD-MS of Intermediates Cn-B were listed in Table 3-2.

TABLE 3-2

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/Mass(M$^+$) |
| Intermediate C1 | 93 | Intermediate C1-B | 94 | C$_{41}$H$_{33}$BO$_2$/ 568.51 |
| Intermediate C2 | 91 | Intermediate C2-B | 98 | C$_{41}$H$_{33}$BO$_2$/ 568.51 |

TABLE 3-2-continued

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass(M+) |
| 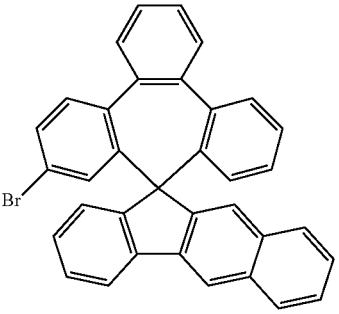 Intermediate C4 | 81 | 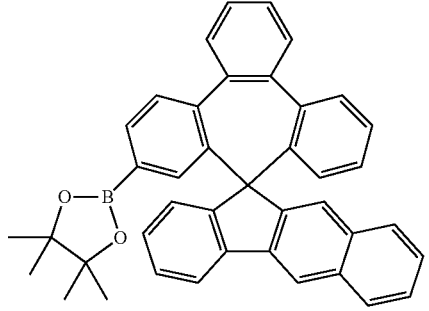 Intermediate C4-B | 95 | $C_{41}H_{33}BO_2$/ 568.51 |
| 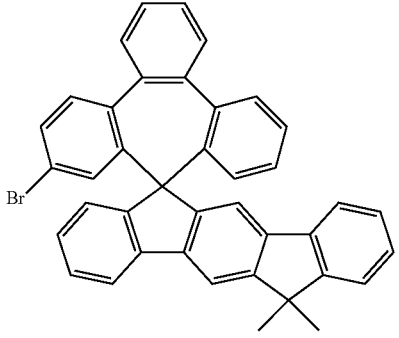 Intermediate C6 | 87 | 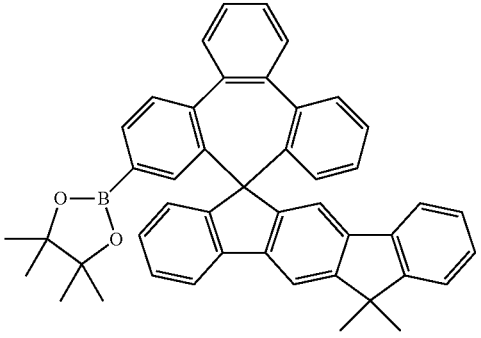 Intermediate C6-B | 93 | $C_{46}H_{39}BO_2$/ 634.63 |
| 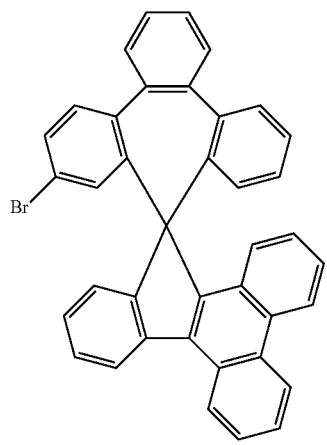 Intermediate C8 | 83 | 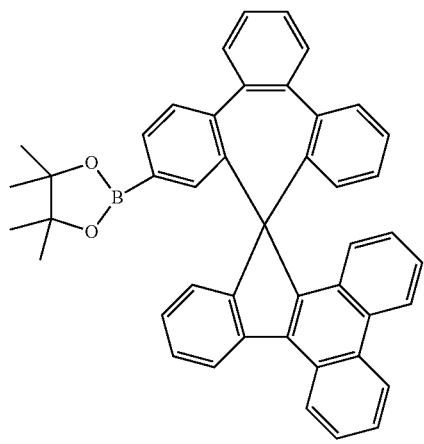 Intermediate C8-B | 95 | $C_{45}H_{35}BO_2$/ 618.59 |

TABLE 3-2-continued

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass($M^+$) |
| 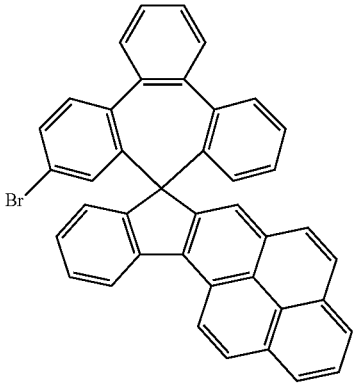 Intermediate C10 | 95 | 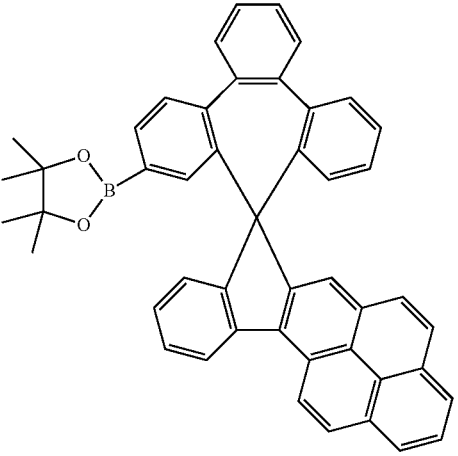 Intermediate C10-B | 97 | $C_{47}H_{35}BO_2$/ 642.59 |

Modifications Intermediate Cn-B

In addition to the Intermediates C1-B, C2-B, C4-B, C6-B, C8-B, and C10-B, one person skilled in the art can adopt any one of Intermediates Cn other than Intermediates C1, C2, C4, C6, C8, and C10 to undergo a Miyaura borylation reaction to successfully synthesize other desired intermediates as follows.

Intermediate C3-B

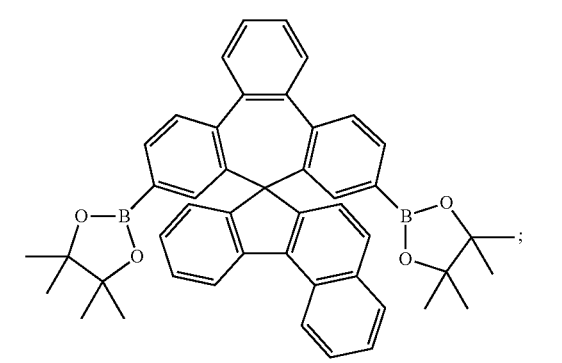

Intermediate C5-B

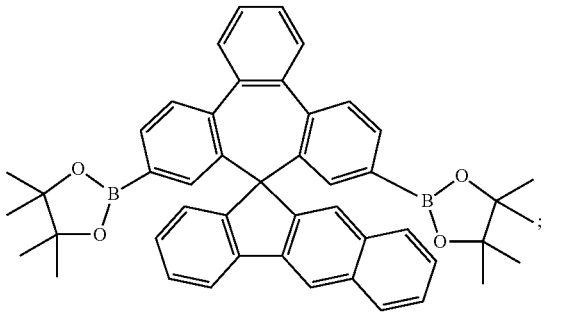

Intermediate C7-B

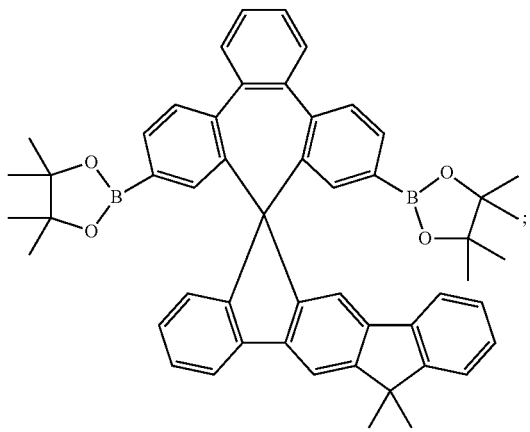

Intermediate C9-B

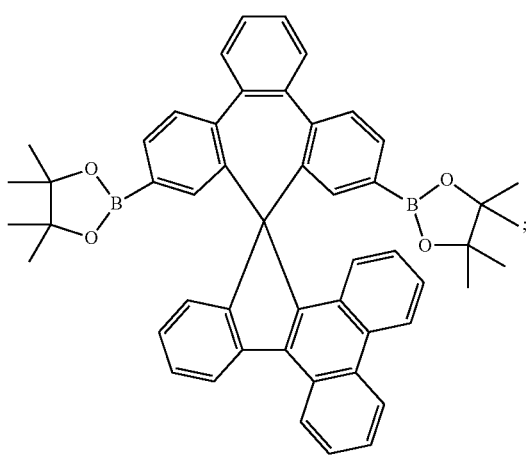

Intermediate C11-B

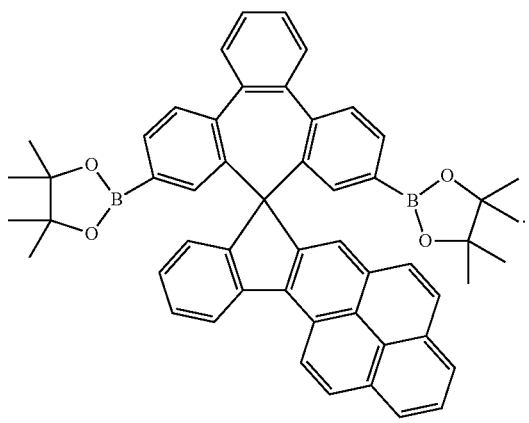

Synthesis of Novel Compounds

Each of Intermediates C1 to C11 and C1-B to C11-B could be reacted with various reactants to synthesize various claimed novel compounds. The general synthesis pathway of the claimed novel compound was summarized in Scheme I. In the following Scheme I, "Reactant B" may be any one of Reactants B1 to B34 as listed in Table 4, and "Intermediate C" may be any one of foresaid Intermediates Cn and Cn-B. The compounds were each synthesized by the following steps.

Scheme I

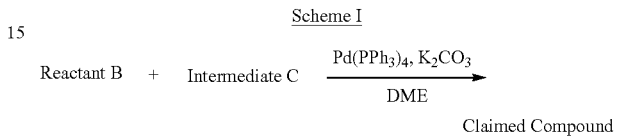

Claimed Compound

TABLE 4 chemical structure and CAS No. of Reactants B1 to B34.

| Reactant No. | Reactant B1 | Reactant B2 | Reactant B3 |
|---|---|---|---|
| Chemical Structure | (HO)₂B—⟨⟩—CN | pyridine-pyridine-Br | pinacol boronate-pyrimidine-phenyl |
| CAS No. | [126747-14-6] | [774-53-8] | [1319255-85-0] |

| Reactant No. | Reactant B4 | Reactant B5 | Reactant B6 |
|---|---|---|---|
| Chemical Structure | Cl-diphenylpyrimidine | Br-pyridine-phenyl-CN | Cl-phenanthroline |
| CAS No. | [29509-91-9] | [916653-46-8] | [7089-68-1] |

| Reactant No. | Reactant B7 | Reactant B8 | Reactant B9 |
|---|---|---|---|
| Chemical Structure | Cl-phenylquinazoline | phenyl-benzimidazole-phenyl-B(OH)₂ | diphenyl-triazine-Cl |
| CAS No. | [29874-83-7] | [867044-33-5] | [3842-55-5] |

TABLE 4-continued chemical structure and CAS No. of Reactants B1 to B34.

| Reactant No. | Reactant B10 | Reactant B11 | Reactant B12 |
|---|---|---|---|
| Chemical Structure | | | |
| CAS No. | [181219-01-2] | [6484-25-9] | [1009033-87-7] |

| Reactant No. | Reactant B13 | Reactant B14 | Reactant B15 |
|---|---|---|---|
| Chemical Structure | | | |
| CAS No. | — | [329214-79-1] | [1260106-29-3] |

| Reactant No. | Reactant B16 | Reactant B17 | Reactant B18 |
|---|---|---|---|
| Chemical Structure | | | |
| CAS No. | [867044-33-5] | [150255-96-2] | [406482-73-3] |

| Reactant No. | Reactant B19 | Reactant B20 | Reactant B21 |
|---|---|---|---|
| Chemical Structure | | | |
| CAS No. | [952514-79-3] | [1588407-97-9] | [1300115-09-6] |

TABLE 4-continued
chemical structure and CAS No. of Reactants B1 to B34.
| Reactant No. | Reactant B22 | Reactant B23 | Reactant B24 |
|---|---|---|---|
| Chemical Structure | 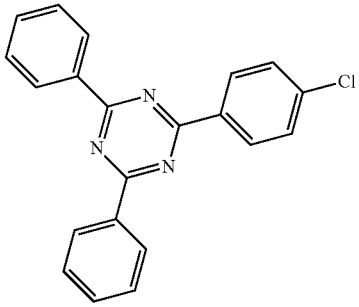 [SMILES: Clc1ccc(-c2nc(-c3ccccc3)nc(-c3ccccc3)n2)cc1] | 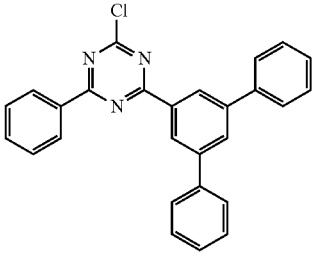 [SMILES: Clc1nc(-c2ccccc2)nc(-c2cc(-c3ccccc3)cc(-c3ccccc3)c2)n1] | 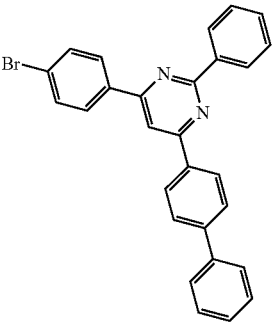 [SMILES: Brc1ccc(-c2cc(-c3ccc(-c4ccccc4)cc3)nc(-c3ccccc3)n2)cc1] |
| CAS No. | [3114-52-1] | [1616231-57-2] | [1421599-34-9] |
| Reactant No. | Reactant B25 | Reactant B26 | Reactant B27 |
|---|---|---|---|
| Chemical Structure | 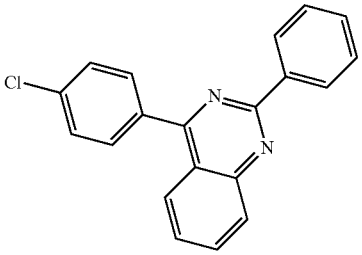 [SMILES: Clc1ccc(-c2nc(-c3ccccc3)nc3ccccc23)cc1] | 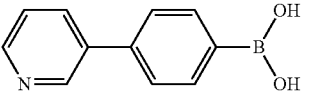 [SMILES: OB(O)c1ccc(-c2cccnc2)cc1] | 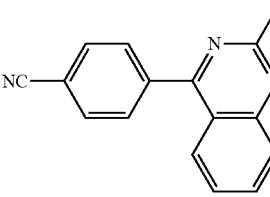 |
| CAS No. | [99682-89-0] | [170230-28-1] | — |
| Reactant No. | Reactant B28 | Reactant B29 | Reactant B30 |
|---|---|---|---|
| Chemical Structure | 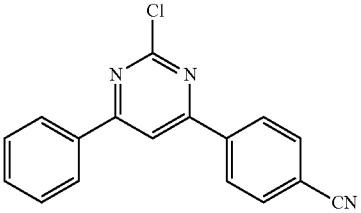 [SMILES: N#Cc1ccc(-c2cc(-c3ccccc3)nc(Cl)n2)cc1] | 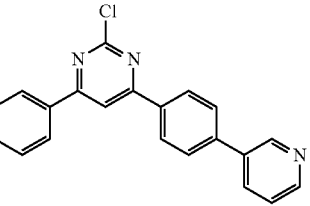 | 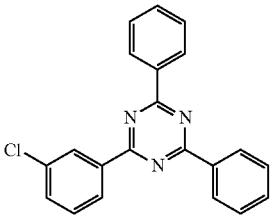 [SMILES: Clc1cccc(-c2nc(-c3ccccc3)nc(-c3ccccc3)n2)c1] |
| Reactant No. | Reactant B31 | Reactant B32 |
|---|---|---|
| Chemical Structure | 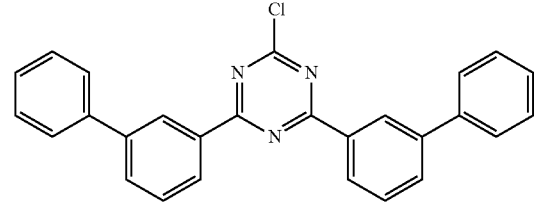 [SMILES: Clc1nc(-c2cccc(-c3ccccc3)c2)nc(-c2cccc(-c3ccccc3)c2)n1] | 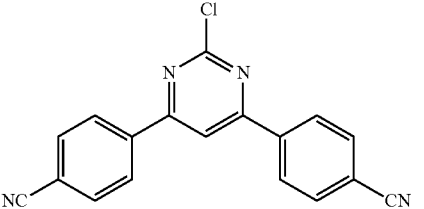 [SMILES: N#Cc1ccc(-c2cc(-c3ccc(C#N)cc3)nc(Cl)n2)cc1] |

TABLE 4-continued chemical structure and CAS No. of Reactants B1 to B34.

| Reactant No. | Reactant B33 | Reactant B34 |
|---|---|---|
| Chemical Structure | 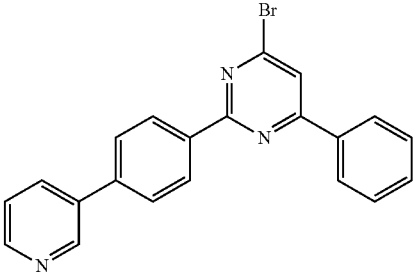 [SMILES: Brc1cc(-c2ccccc2)nc(-c2ccc(-c3cccnc3)cc2)n1] | 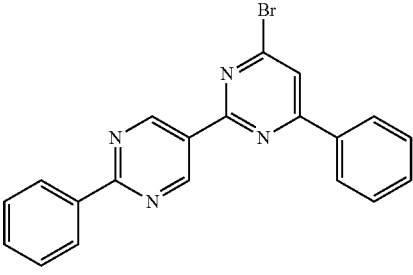 [SMILES: Brc1cc(-c2ccccc2)nc(-c2cnc(-c3ccccc3)nc2)n1] |

A mixture of Intermediate Cn (1.0 eq), Pd(OAc)$_2$(0.01 eq), Pt(Cy)$_2$(2-biphenyl) 0.04 eq), toluene/ethanol (0.5M, v/v=10/1), 3.0 M potassium carbonate solution, and Reactant Bn (1.2 eq) was stirred at 100° C. for 12 h under nitrogen atmosphere. After the completion of the reaction, water and toluene were added to the reaction mass. Subsequently, the organic layer was recovered by solvent extraction operation and dried over sodium sulfate. The solvent was then removed from the organic layer under reduced pressure, and the resulting residue was purified by silica gel column chromatography. The obtained residue was recrystallized with toluene to obtain white solid as the claimed novel compound.

Figure 2:
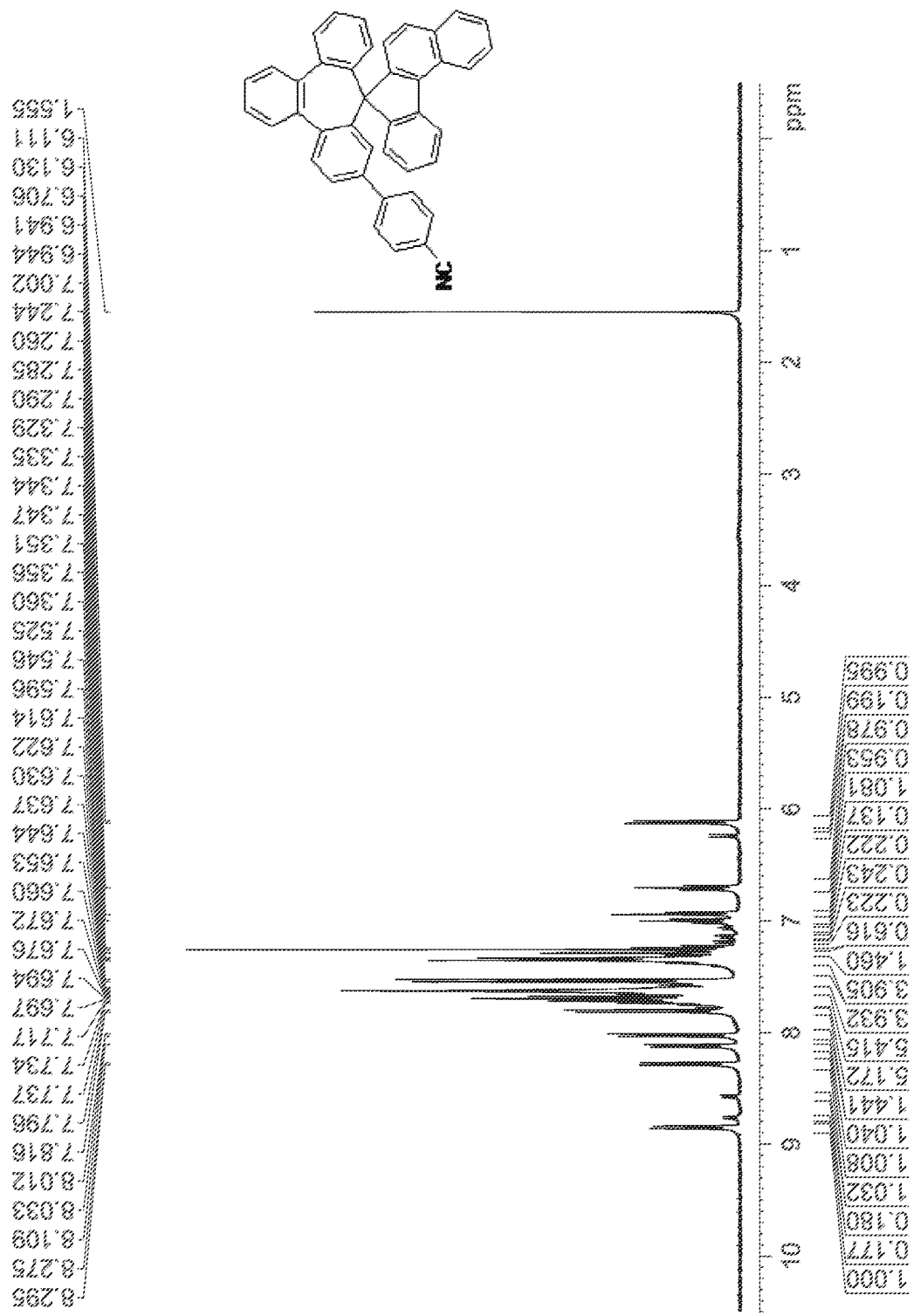
FIGS. 2 to 13 are respectively $^1$H nuclear magnetic resonance (NMR) spectra of Compounds I to XII.
Figure 3:
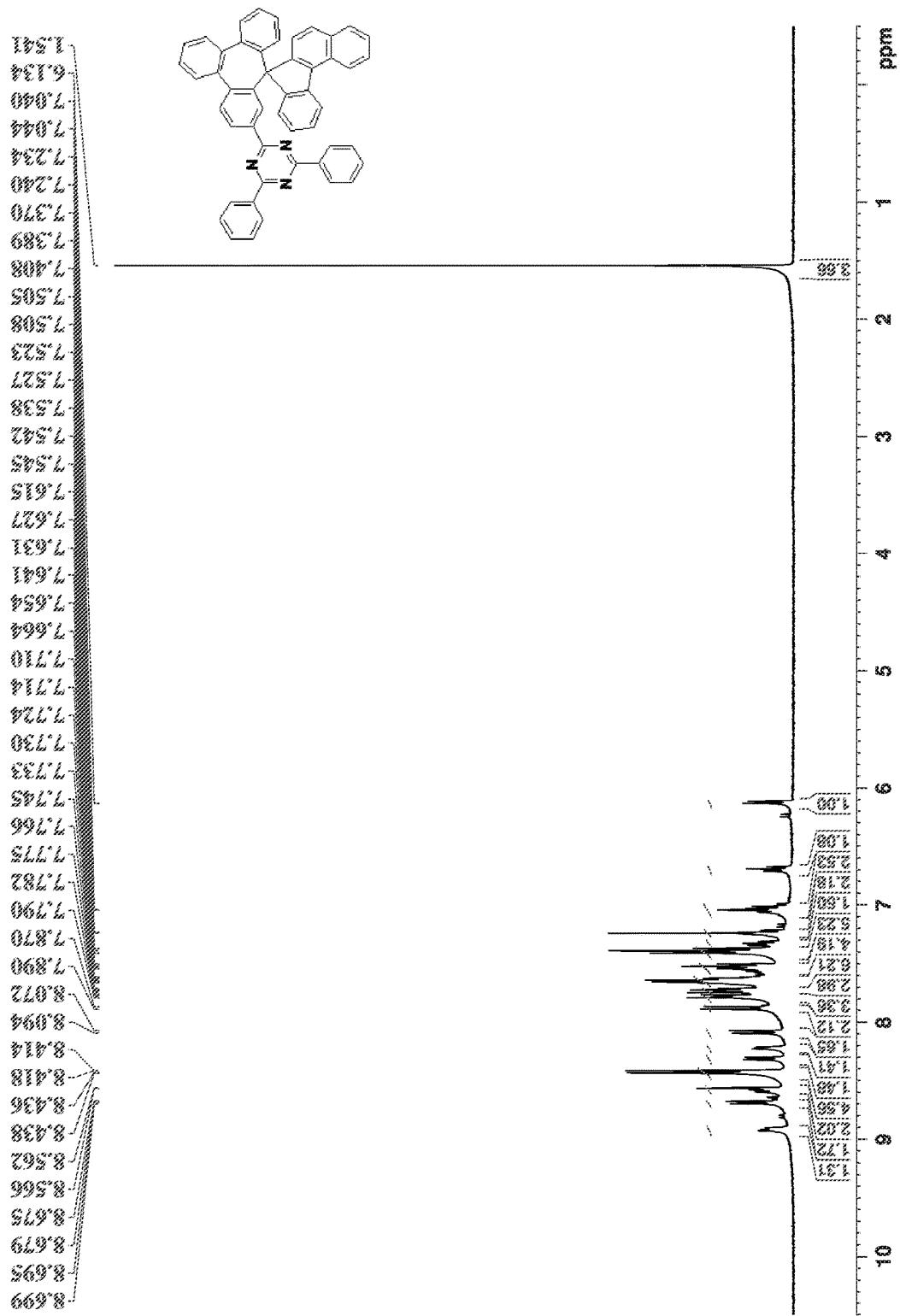
Figure 4:
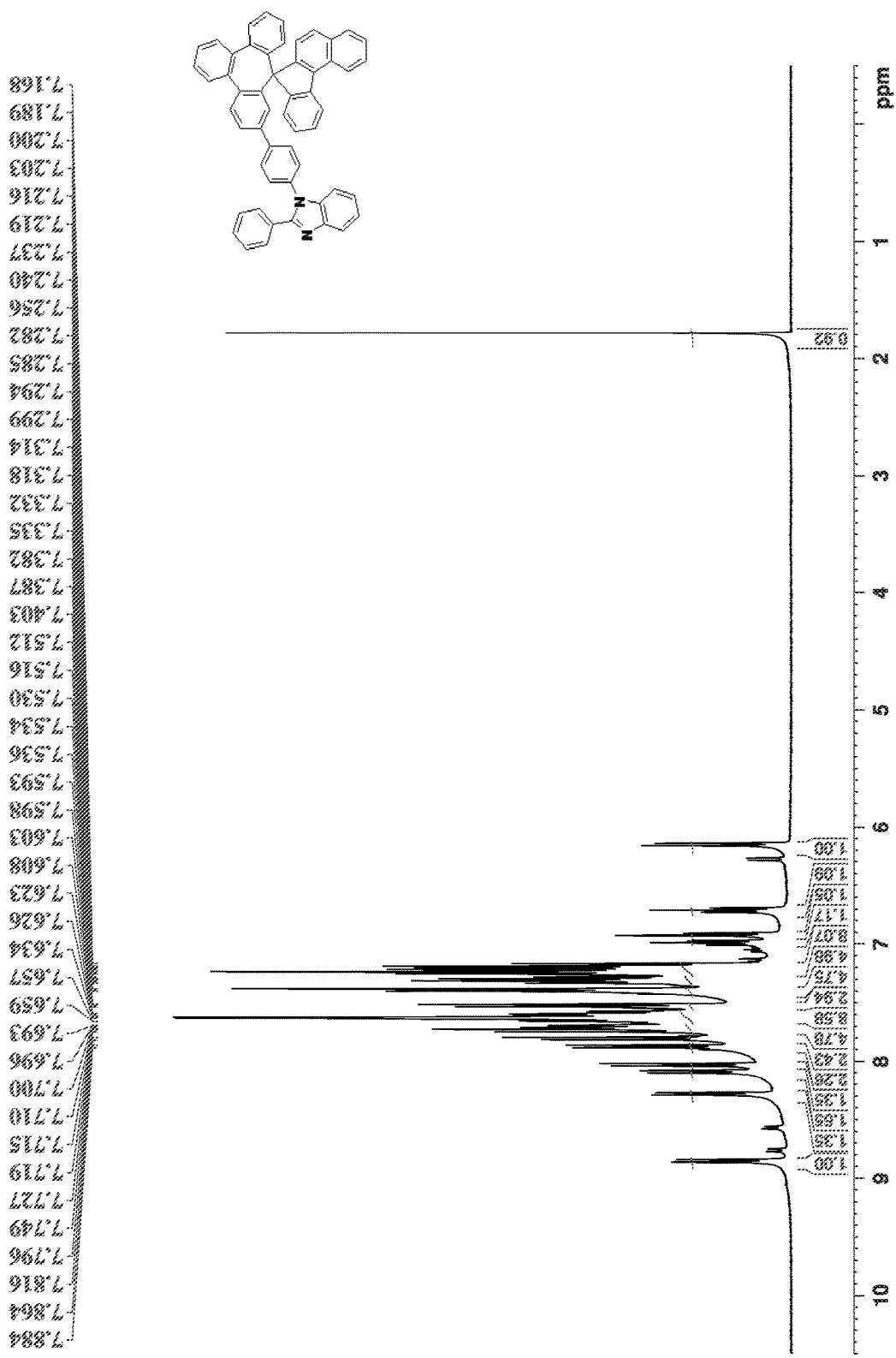
Figure 5:
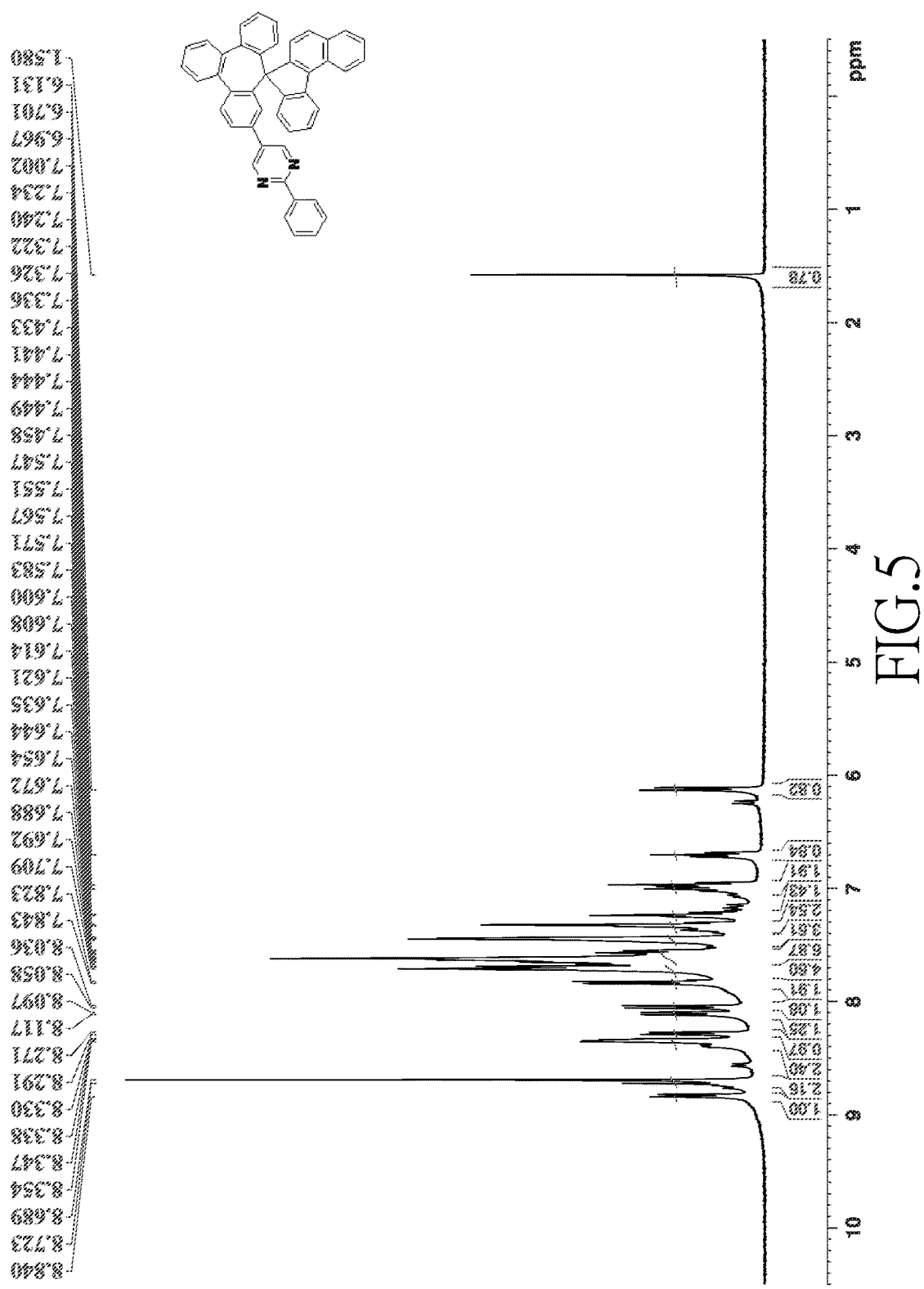
Figure 6:
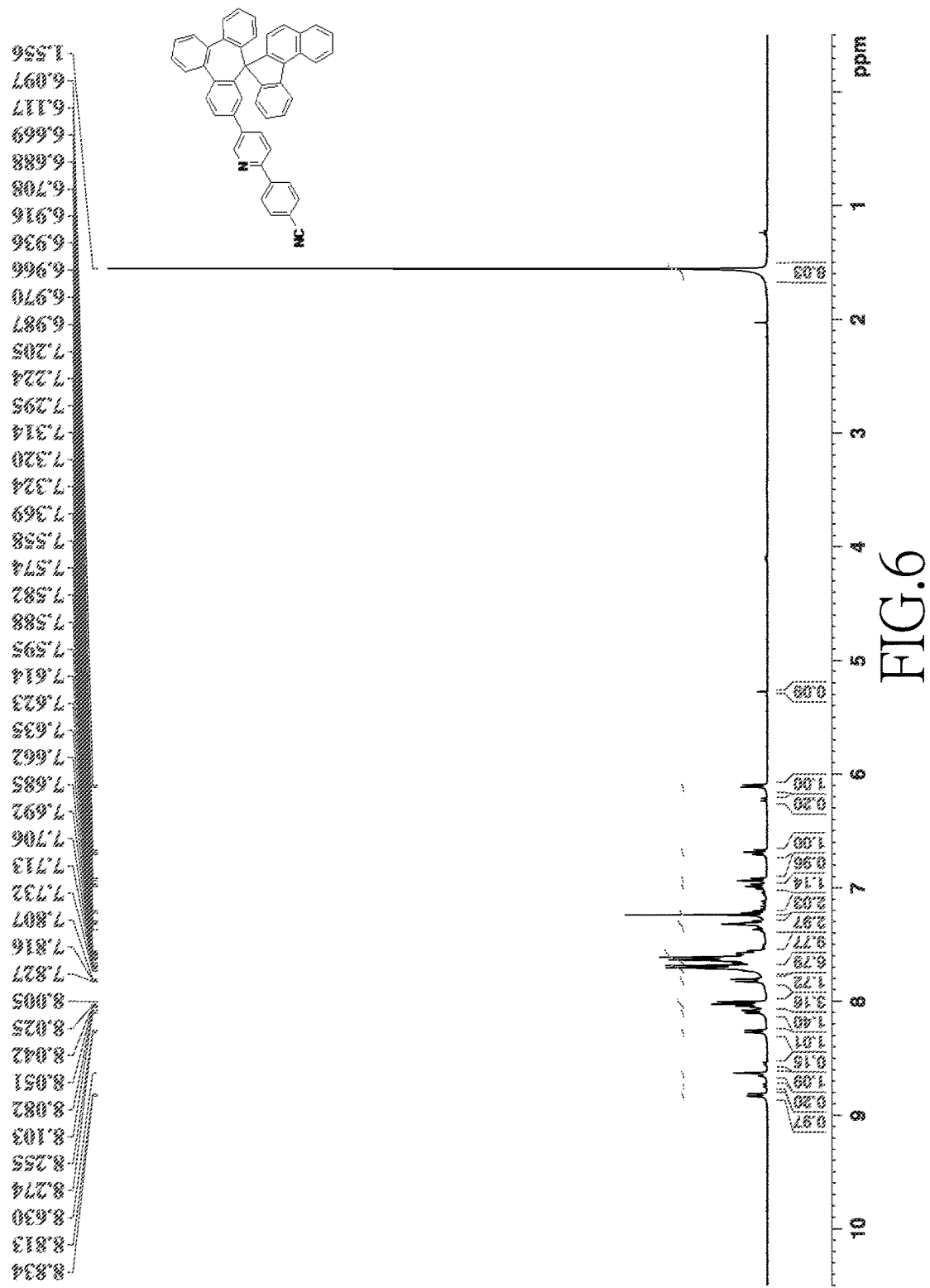
Figure 7:
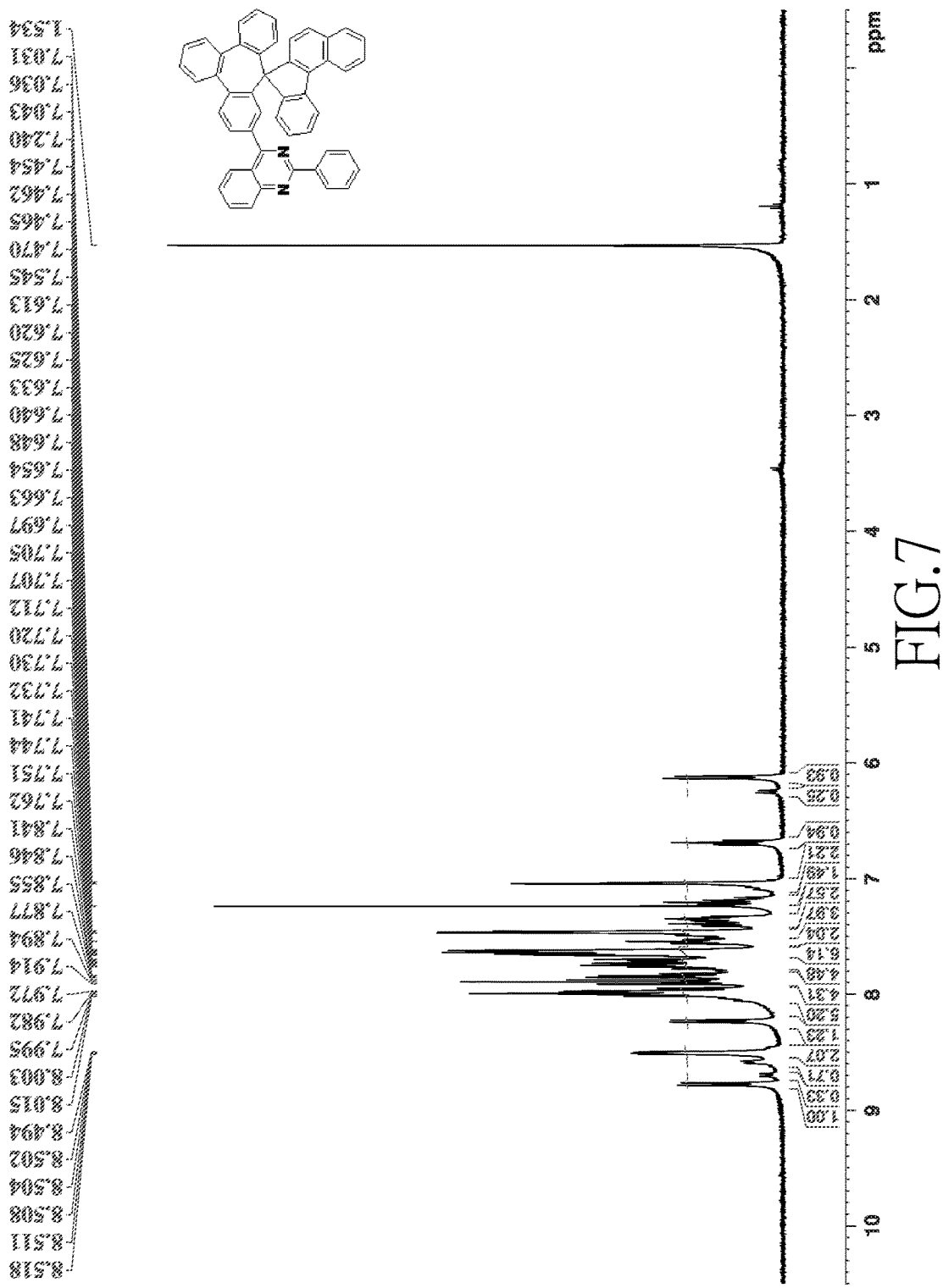
Figure 8:
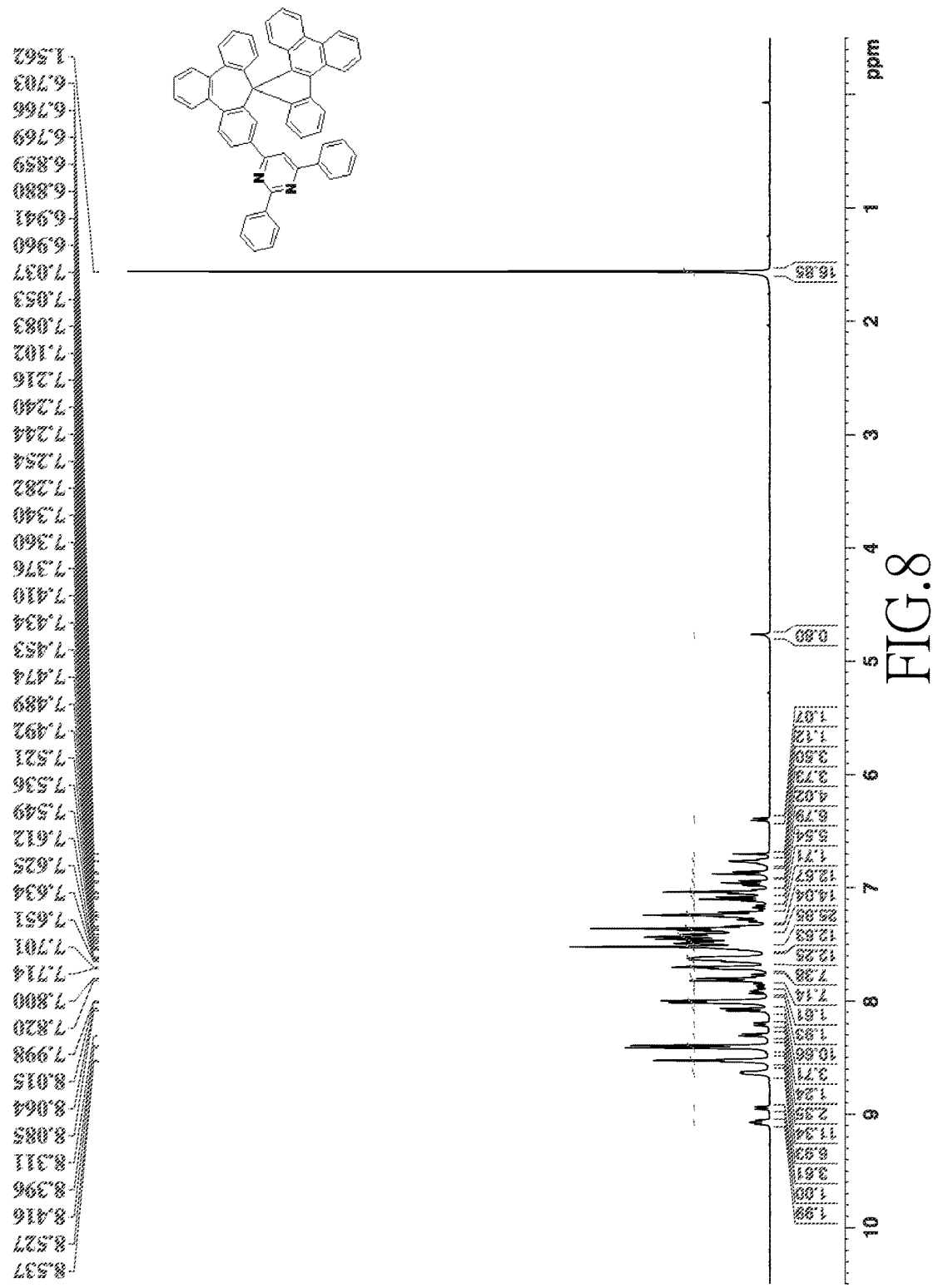
Figure 9:
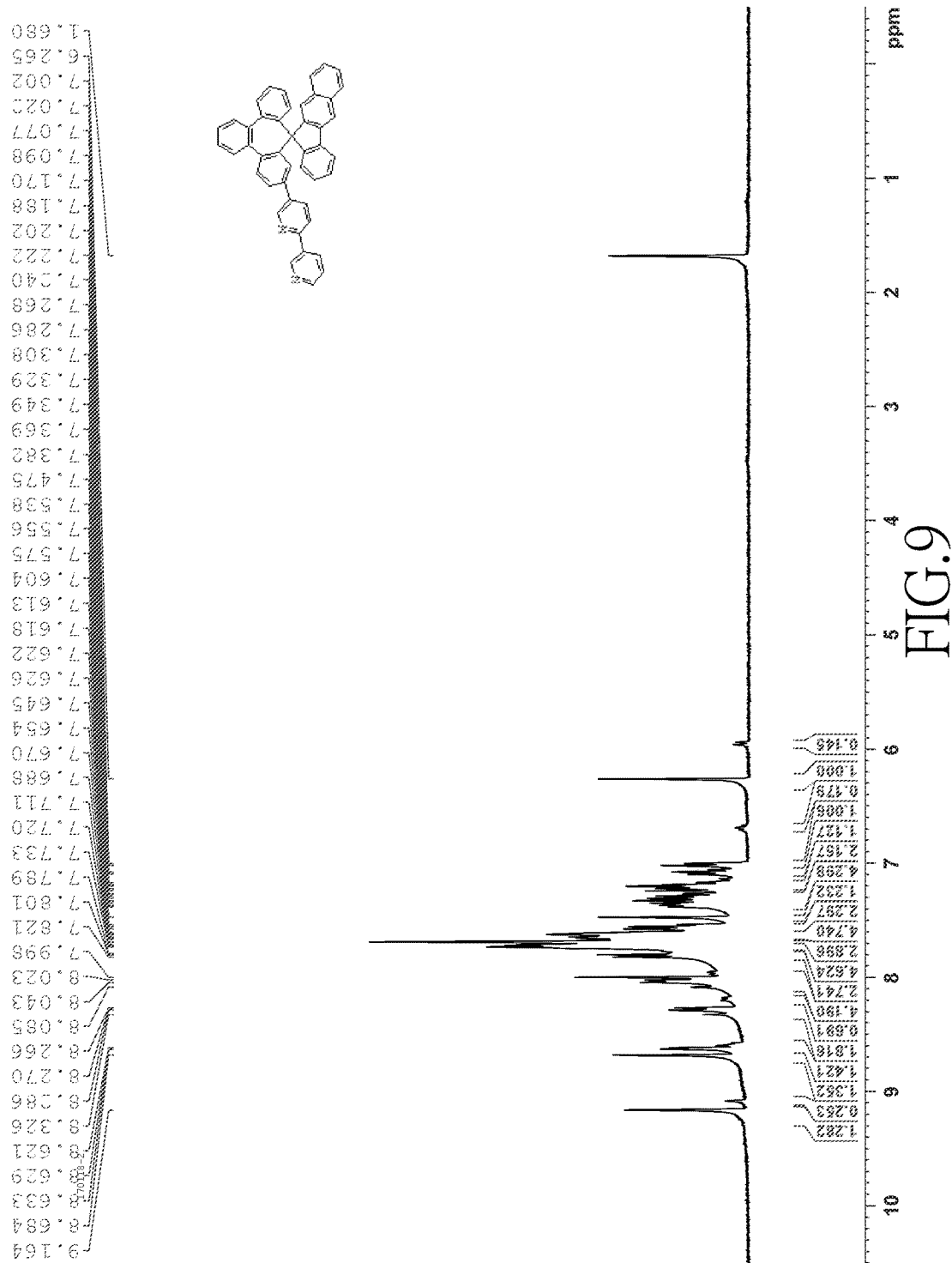
Figure 10:
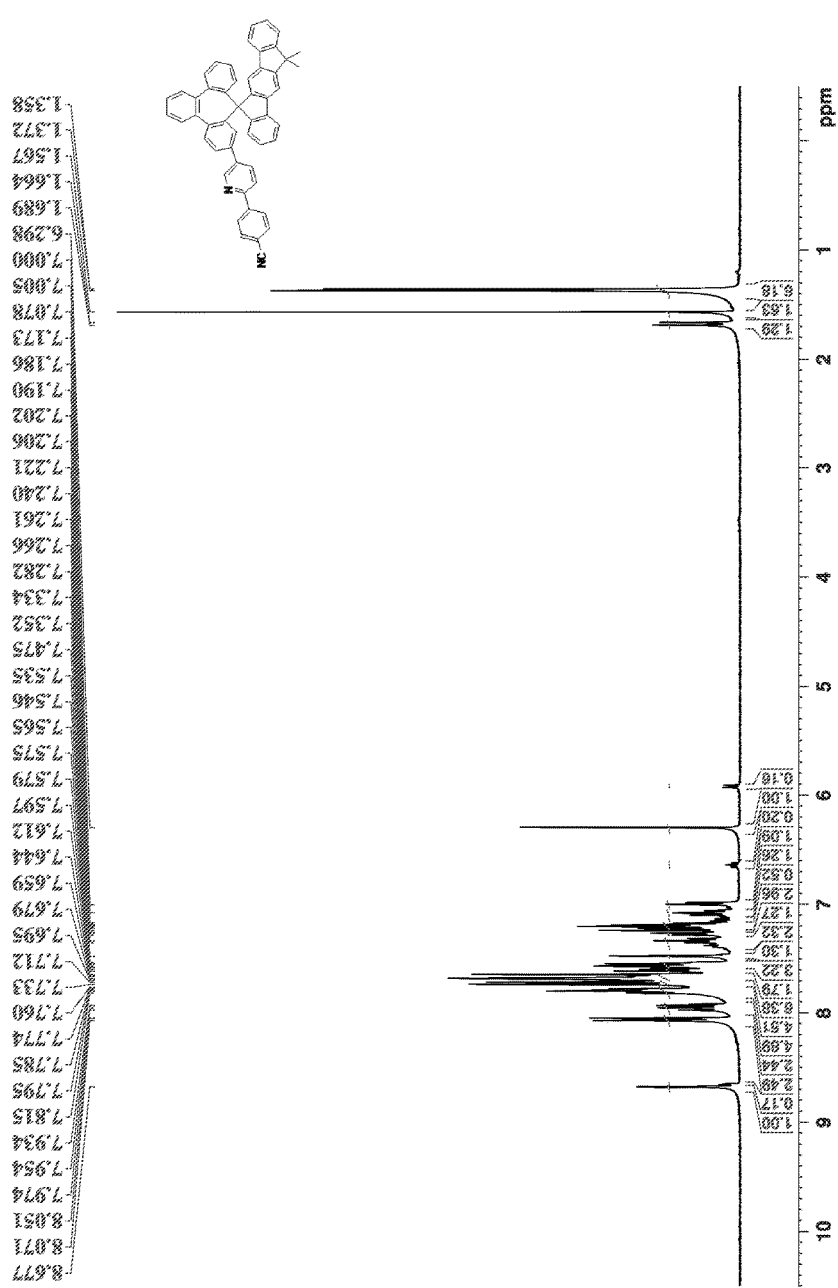
Figure 11:
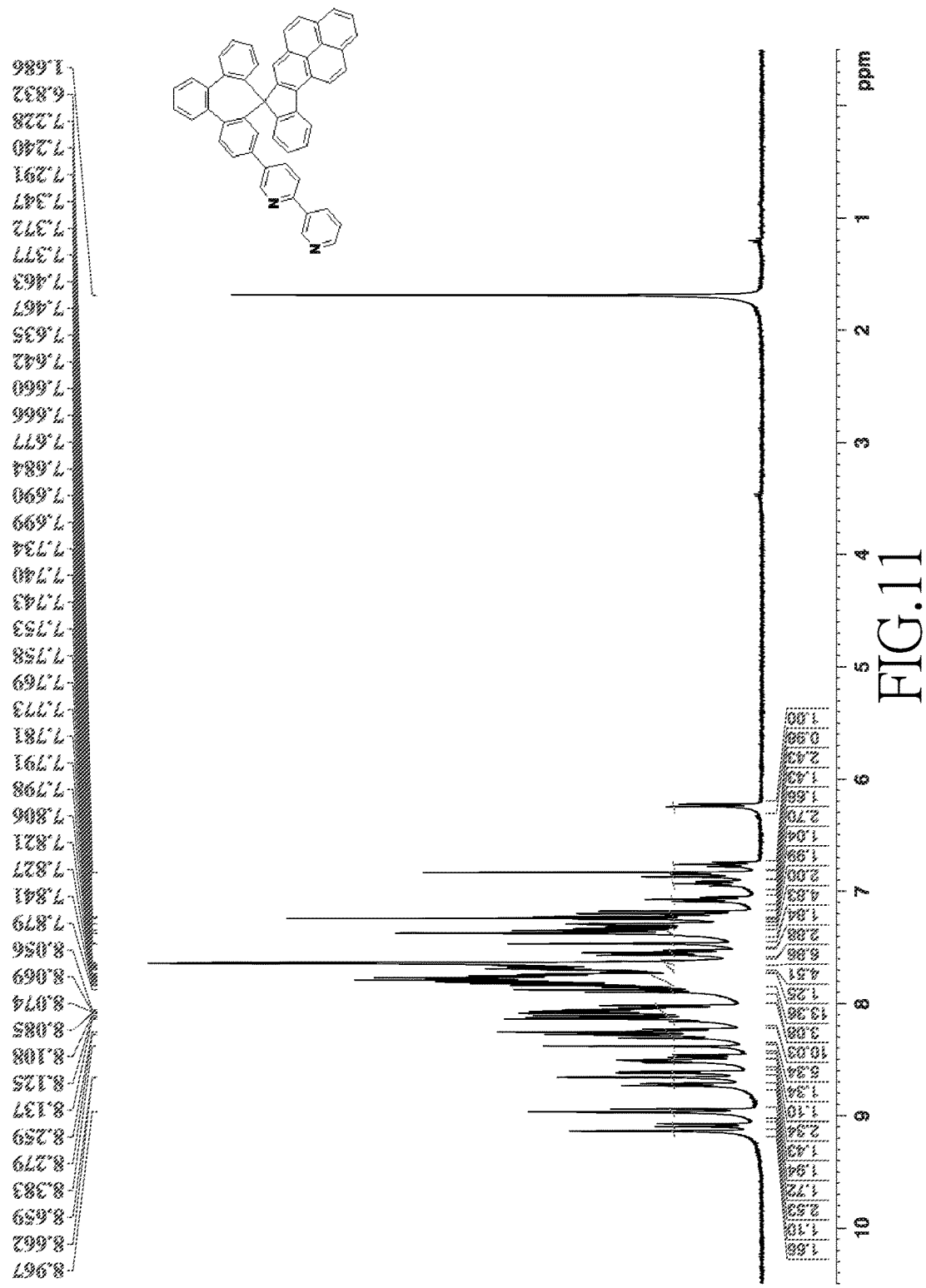
Figure 12:
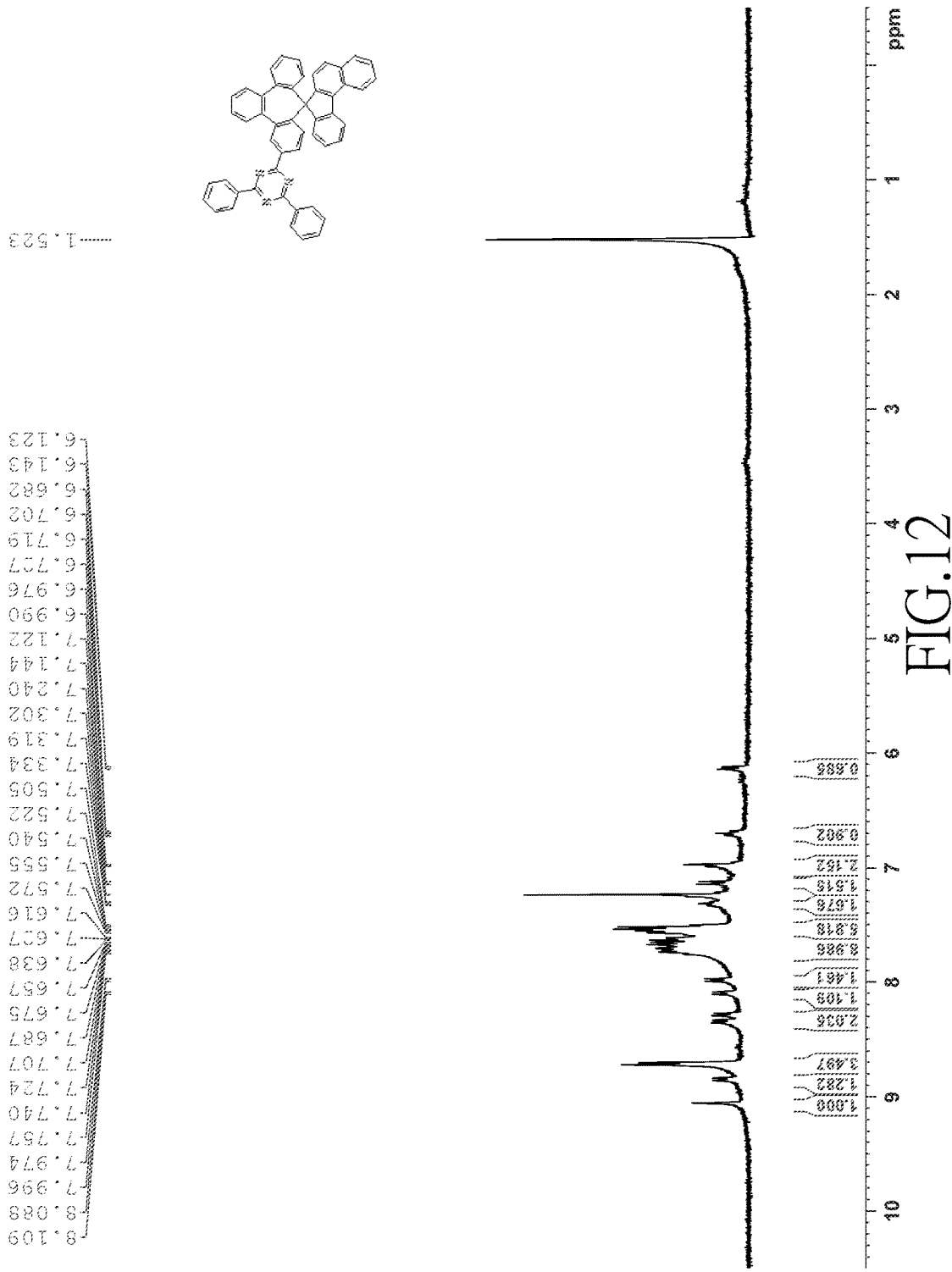
Figure 13:
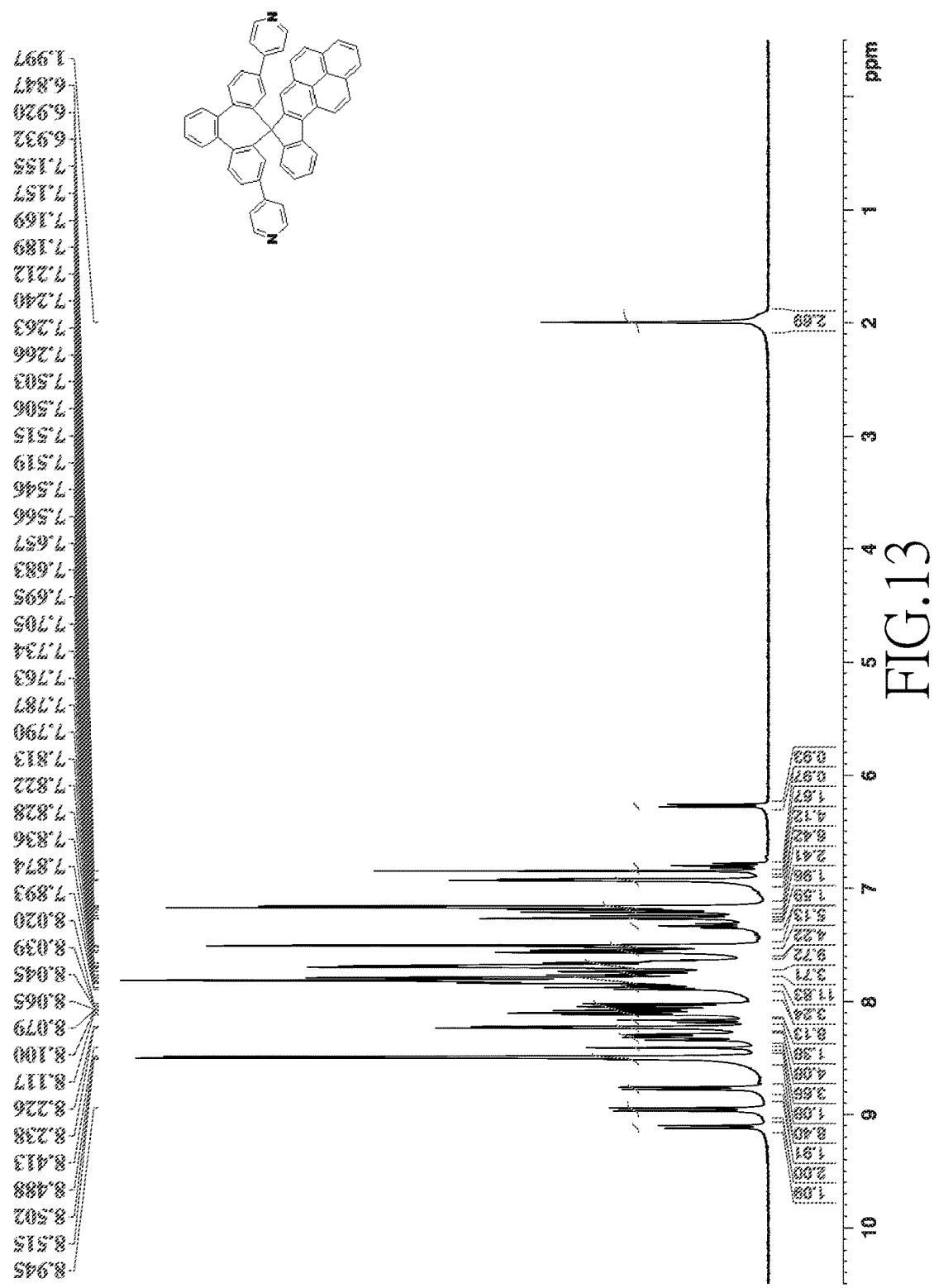

Reactant B and Intermediate C adopted to synthesize Compounds I to XII were listed in Table 5. Compounds I to XII were identified by H$^1$-NMR and FD-MS, and the chemical structure, yield, formula and mass of each of Compounds I to XII were also listed in Table 5. According to FIGS. 2 to 13 and the results of FD-MS, the chemical structure of Compounds I to XII were identified as follows.

TABLE 5 reactants and intermediates adopted to prepare Compounds I to XII and their yields, formulae, and FD-MS data.

| | | Claimed Compound | | |
|---|---|---|---|---|
| Reactant No. | Intermediate No. | Chemical Structure | Yield | Formula/ Mass (M$^+$) |
| B1 | C1 | 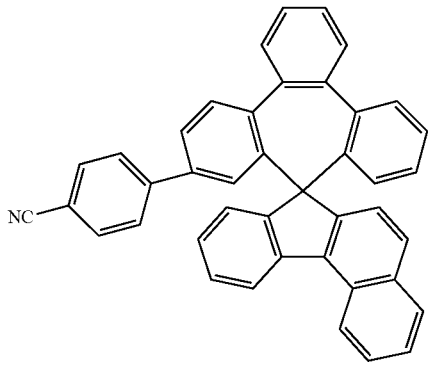 | 86 | C$_{42}$H$_{25}$N/ 543.65 |

Compound I

TABLE 5-continued
reactants and intermediates adopted to prepare Compounds I to XII and their yields, formulae, and FD-MS data.
| Reactant No. | Intermediate No. | Claimed Compound Chemical Structure | Yield | Formula/ Mass (M+) |
|---|---|---|---|---|
| B9 | C1-B | Compound II 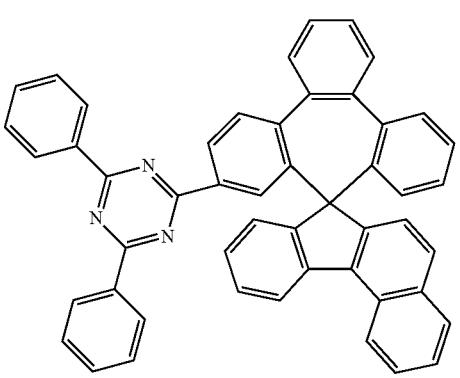 | 81 | $C_{50}H_{31}N_3$/ 673.8 |
| B8 | C1 | Compound III 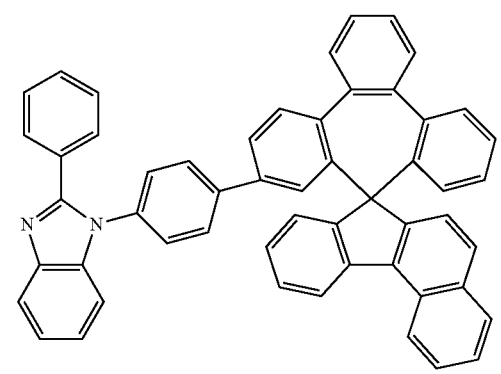 | 89 | $C_{54}H_{34}N_2$/ 710.86 |
| B3 | C1 | Compound IV 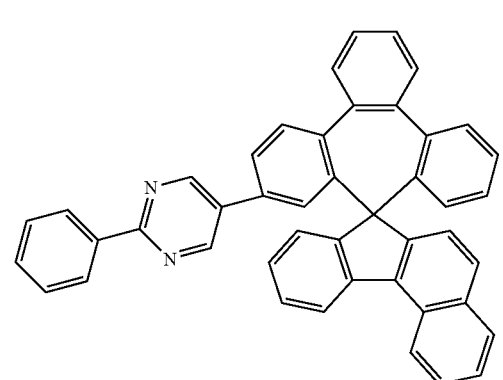 | 91 | $C_{45}H_{28}N_2$/ 596.72 |

TABLE 5-continued reactants and intermediates adopted to prepare Compounds I to XII and their yields, formulae, and FD-MS data.

| Reactant No. | Intermediate No. | Claimed Compound Chemical Structure | Yield | Formula/ Mass (M+) |
|---|---|---|---|---|
| B5 | C1-B | Compound V | 85 | $C_{47}H_{28}N_2$ 620.76 |
| B11 | C1-B | Compound VI | 84 | $C_{49}H_{30}N_2$ 646.79 |
| B4 | C8-B | Compound VII | 82 | $C_{55}H_{34}N_2$ 722.89 |

TABLE 5-continued reactants and intermediates adopted to prepare Compounds I to XII and their yields, formulae, and FD-MS data.

| Reactant No. | Intermediate No. | Claimed Compound Chemical Structure | Yield | Formula/ Mass (M+) |
|---|---|---|---|---|
| B2 | C4-B | Compound VIII | 71 | $C_{45}H_{28}N_2$/ 596.73 |
| B5 | C6-B | Compound IX | 76 | $C_{52}H_{34}N_2$ 686.86 |
| B2 | C10-B | Compound X | 66 | $C_{51}H_{30}N_2$ 670.81 |

TABLE 5-continued reactants and intermediates adopted to prepare Compounds I to XII and their yields, formulae, and FD-MS data.

Claimed Compound

| Reactant No. | Intermediate No. | Chemical Structure | Yield | Formula/ Mass (M+) |
|---|---|---|---|---|
| B9 | C2-B | Compound XI | 93 | $C_{50}H_{31}N_3$ 673.82 |
| B10 | C11 | Compound XII | 72 | $C_{51}H_{30}N_2$ 670.81 |

Modifications of Compounds I to XII

In addition to the Compounds I to XII, one person skilled in the art can react any Intermediate C, i.e., the foresaid Intermediate Cn or Cn-B, with any Reactant B through a reaction mechanism similar to Scheme I to synthesize other desired claimed novel compounds.

Preparation of OLED devices

A glass substrate coated with an ITO layer (abbreviated in ITO substrate) in a thickness of 1500 Å was placed in distilled water containing a detergent dissolved therein, and was ultrasonically washed. The detergent was a product manufactured by Fischer Co., and the distilled water was distilled water filtered, twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples 1 to 29. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a first hole transporting layer (HTL-1), a second hole transporting layer (HTL-2), a blue/green/red emission layer (BEL/GEL/REL), an electron transporting layer (ETL), an electron injection layer (EIL), and a cathode (Cthd).

Herein, HAT was a material for forming HIL-1 and was a dopant for forming HIL-2; HI-2 was a material for forming HIL-2; HT-1 and HT-2 were respectively materials for forming HTL-1 and HTL-2; conventional ET and novel compounds of the present invention were materials for forming ETL; Liq was a dopant for forming ETL and was a material for forming EIL. RH/GH/BH were host materials for forming REL/GEL/BEL, and RD/GD/BD were dopants for forming REL/GEL/BEL. The main difference of the OLEDs between Examples and Comparative Examples was that the ETL of OLED in the following comparative examples was made of BCP but the ETLs of OLEDs in the following examples were made of the novel compounds of the present invention as listed in Table 5. The detailed chemical structures of foresaid commercial materials were listed in Table 6.

TABLE 6
chemical structures of commercial materials for OLED devices.
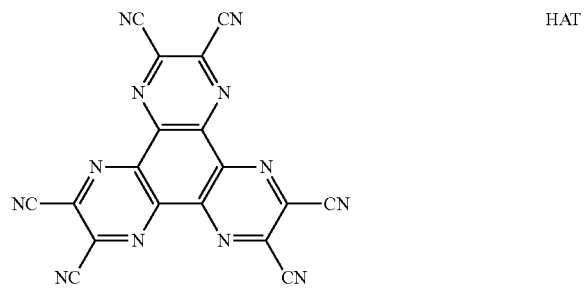
HAT
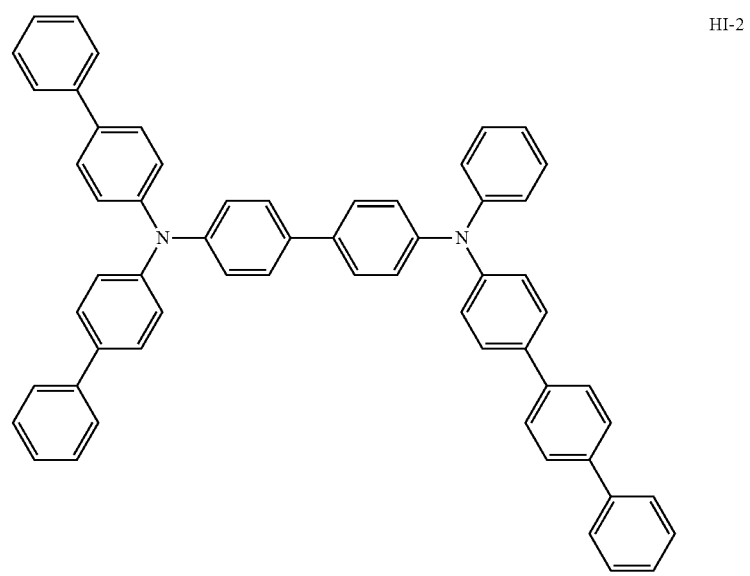
HI-2
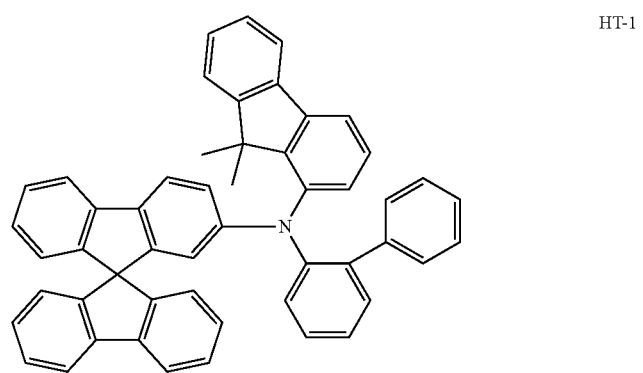
HT-1

TABLE 6-continued
chemical structures of commercial materials for OLED devices.
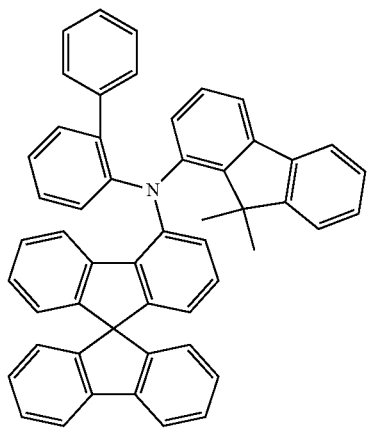 [SMILES: CC1(C)c2ccccc2-c2cccc(N(c3ccccc3-c3ccccc3)c3cccc4c3-c3ccccc3C43c4ccccc4-c4ccccc43)c21]
HT-2
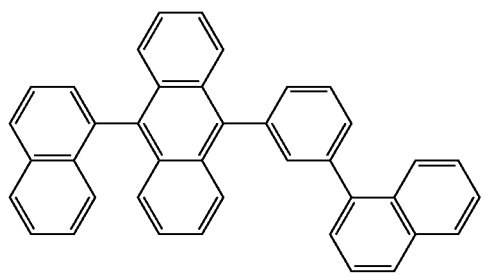 [SMILES: c1cc(-c2cccc3ccccc23)cc(-c2c3ccccc3c(-c3cccc4ccccc34)c3ccccc23)c1]
BH
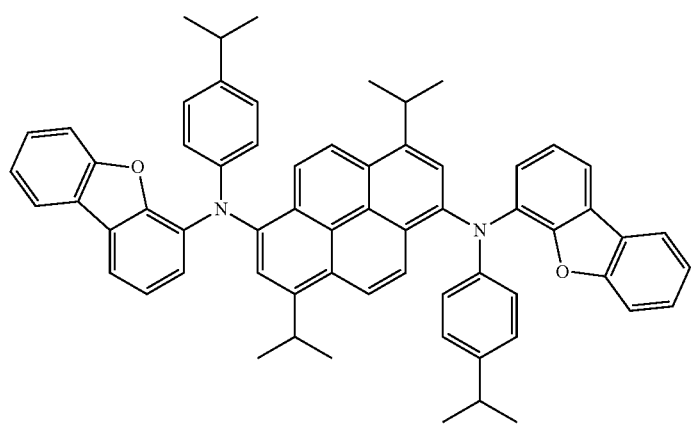 [SMILES: CC(C)c1ccc(N(c2cc(C(C)C)c3ccc4c(N(c5ccc(C(C)C)cc5)c5cccc6c5oc5ccccc56)cc(C(C)C)c5ccc2c3c54)c2cccc3c2oc2ccccc23)cc1]
BD
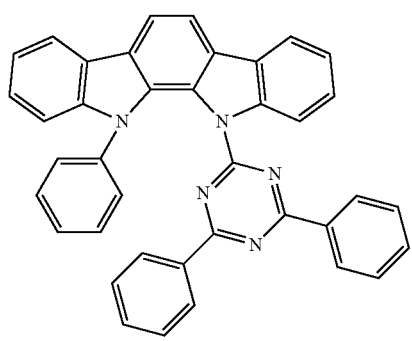 [SMILES: c1ccc(-c2nc(-c3ccccc3)nc(-n3c4ccccc4c4ccc5c6ccccc6n(-c6ccccc6)c5c43)n2)cc1]
GH TABLE 6-continued
chemical structures of commercial materials for OLED devices.
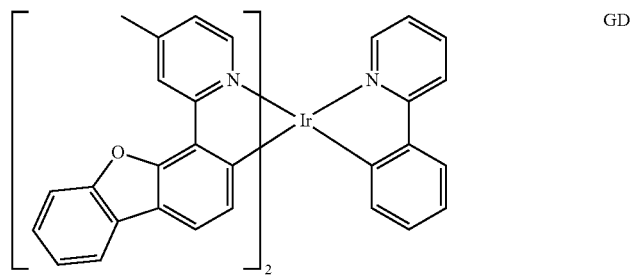
GD
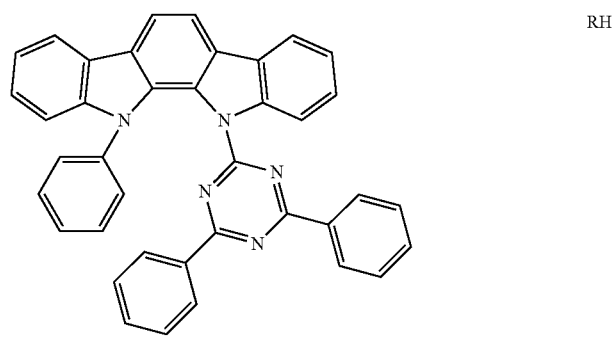
RH
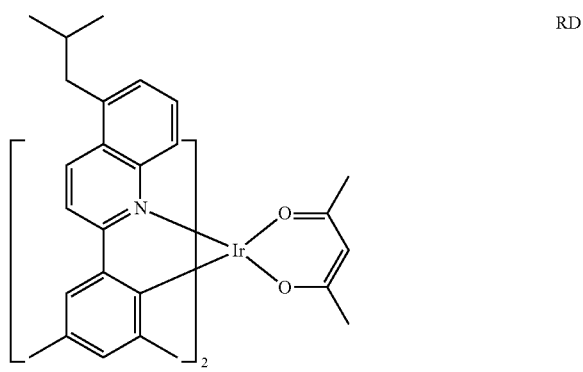
RD
Liq
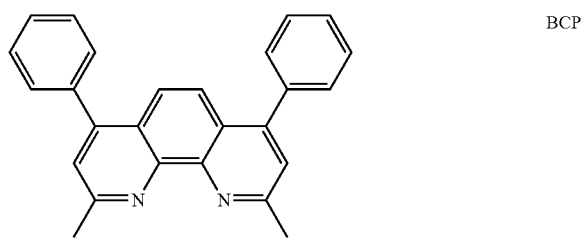
BCP Preparation of Red OLED Devices To prepare the red OLED device, multiple organic layers were respectively deposited on the ITO substrate according to the sequence as listed in Table 7, and the materials and the thicknesses of the organic layers in red OLED devices were also listed in Table 7.

TABLE 7 coating sequence, materials and thickness of the organic layers in red OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 2100 Å |
| 3 | HTL-1 | HT-1 | 100 Å |
| 4 | HTL-2 | HT-2 | 100 Å |
| 5 | REL | RH doped with 3.5 wt % of RD | 300 Å |
| 6 | ETL | Commercial ET/novel compounds doped with 35.0 wt % of Liq | 350 Å |
| 7 | EIL | Liq | 15 Å |
| 8 | Cthd | Al | 1500 Å |

Preparation Green OLED Devices

To prepare the green OLED device, multiple organic layers were respectively deposited on the ITO substrate according to the sequence as listed in Table 8. and the materials and the thicknesses of the organic layers in green OLED devices were also listed in Table 8.

TABLE 8 coating sequence, materials and thickness of the layers in green OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 2100 Å |
| 3 | HTL-1 | HT-1 | 100 Å |
| 4 | HTL-2 | HT-2 | 100 Å |
| 5 | GEL | GH doped with 10.0 wt % of GD | 300 Å |
| 6 | ETL | Commercial ET/novel compounds doped with 35.0 wt % of Liq | 350 Å |
| 7 | EIL | Liq | 15 Å |
| 8 | Cthd | Al | 1500 Å |

Preparation of Blue OLED Devices

To prepare the blue OLED device, multiple organic layers were respectively deposited on the ITO substrate according to the sequence as listed in Table 9, and the materials and the thicknesses of the organic layers in blue OLED devices were also listed in Table 9.

TABLE 9 coating sequence, materials and thickness of the layers in blue OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 2100 Å |
| 3 | HTL-1 | HT-1 | 100 Å |
| 4 | HTL-2 | HT-2 | 100 Å |
| 5 | BEL | BH doped with 3.5 wt % of BD | 300 Å |
| 6 | ETL | Commercial ET/novel compounds doped with 35.0 wt % of Liq | 350 Å |
| 7 | EIL | Liq | 15 Å |
| 8 | Cthd | Al | 1500 Å |

Performance of OLED Device

To evaluate the performance of OLED devices, red, green, and blue OLED devices were measured by PR650 as photometer and Keithley 2400 as power supply. Color coordinates (x,y) were determined according to the CIE chromaticity scale (Commission Internationale de L'Eclairage, 1931). The results were shown in Table 10. For the blue and red OLED devices, the data were collected at 1000 nits. For the green OLED devices, the data were collected at 3000 nits.

The materials of ETL, color and data of CIE, driving voltage, current efficiency, and external quantum efficiency (EQE) of Examples 1 to 29 and Comparative Examples 1 to 3 were listed in Table 10.

TABLE 10 materials of ETL, characteristics and performance of OLED devices of Examples 1 to 29 and Comparative Examples 1 to 3.

| OLED device No. | Material of ETL | Color, CIE (x, y) | Voltage (V) | Current Efficiency (cd/A) | EQE (%) |
|---|---|---|---|---|---|
| Example 1 | Compound I | B (0.130, 0.151) | 5.09 | 10.5 | 7.67 |
| Example 2 | Compound II | B (0.129, 0.152) | 4.04 | 11.4 | 7.78 |
| Example 3 | Compound III | B (0.130, 0.163) | 6.02 | 8.10 | 6.31 |
| Example 4 | Compound IV | B (0.129, 0.155) | 6.00 | 9.12 | 6.56 |
| Example 5 | Compound V | B (0.129, 0.153) | 4.85 | 9.85 | 7.25 |
| Example 6 | Compound VI | B (0.129, 0.155) | 4.98 | 10.8 | 7.56 |
| Example 7 | Compound VII | B (0.130, 0.147) | 4.97 | 10.2 | 6.86 |
| Example 8 | Compound VIII | B (0.129, 0.156) | 4.83 | 10.7 | 7.15 |
| Example 9 | Compound IX | B (0.129, 0.150) | 5.05 | 8.79 | 6.41 |
| Example 10 | Compound X | B (0.129, 0.151) | 4.13 | 10.5 | 6.86 |
| Example 11 | Compound XI | B (0.129, 0.150) | 4.76 | 10.5 | 6.44 |
| Example 12 | Compound XII | B (0.129, 0.159) | 4.47 | 10.0 | 6.71 |
| Comparative Example 1 | BCP | B (0.130, 0.142) | 6.71 | 6.98 | 4.88 |
| Example 13 | Compound I | G (0.314, 0.638) | 4.60 | 76.9 | 17.42 |
| Example 14 | Compound II | G (0.311, 0.639) | 2.98 | 77.9 | 17.95 |
| Example 15 | Compound IV | G (0.313, 0.639) | 4.59 | 71.0 | 17.0 |
| Example 16 | Compound V | G (0.320, 0.635) | 3.08 | 74.9 | 20.01 |
| Example 17 | Compound VI | G (0.313, 0.639) | 3.45 | 72.0 | 17.87 |
| Example 18 | Compound VIII | G (0.317, 0.637) | 3.32 | 75.6 | 18.95 |
| Example 19 | Compound IX | G (0.315, 0.638) | 3.33 | 74.4 | 18.75 |
| Example 20 | Compound X | G (0.310, 0.641) | 3.80 | 75.1 | 17.05 |
| Example 21 | Compound XI | G (0.319, 0.637) | 3.89 | 82.2 | 17.74 |
| Comparative Example 2 | BCP | G (0.313, 0.638) | 4.67 | 70.3 | 16.95 |
| Example 22 | Compound II | R (0.659, 0.339) | 4.05 | 24.3 | 16.37 |
| Example 23 | Compound IV | R (0.658, 0.340) | 4.10 | 25.0 | 17.16 |
| Example 24 | Compound V | R (0.658, 0.340) | 3.64 | 24.6 | 17.37 |
| Example 25 | Compound VI | R (0.659, 0.339) | 4.06 | 24.2 | 16.38 |

TABLE 10-continued materials of ETL, characteristics and performance of OLED devices of Examples 1 to 29 and Comparative Examples 1 to 3.

| OLED device No. | Material of ETL | Color, CIE (x, y) | Voltage (V) | Current Efficiency (cd/A) | EQE (%) |
|---|---|---|---|---|---|
| Example 26 | Compound VIII | R (0.660, 0.338) | 3.78 | 24.2 | 16.58 |
| Example 27 | Compound IX | R (0.662, 0.337) | 3.82 | 24.5 | 16.99 |
| Example 28 | Compound X | R (0.659, 0.339) | 4.12 | 28.1 | 20.88 |
| Example 29 | Compound XI | R (0.660, 0.338) | 3.90 | 24.6 | 16.12 |
| Comparative Example 3 | BCP | R (0.659, 0.340) | 4.16 | 24.1 | 16.05 |

Based on the results, in comparison with the commercial electron transport material, adopting Compounds I to XII as the electron transport material can reduce the driving voltage and improve the current efficiency and the external quantum efficiency of the red, green, or blue OLEDs. It demonstrated that the novel compound or the present invention is suitable as an electron transport material for any color OLEDs, and allows the OLEDs using the same to have low driving voltage and improved current efficiency as well as improved external quantum efficiency.

Even though numerous characteristics and advantages of the present invention have been set forth in the foregoing description, it together with details of the structure and features of the invention, the disclosure is illustrative only. Changes may be made in the details, especially in matters of quantity, position, and arrangement of substitution groups within the principles of the invention to the full extent indicated by the broad general meaning of the terms in which the appended claims are expressed.

What is claimed is:

1. A compound represented by the following Formula (I):

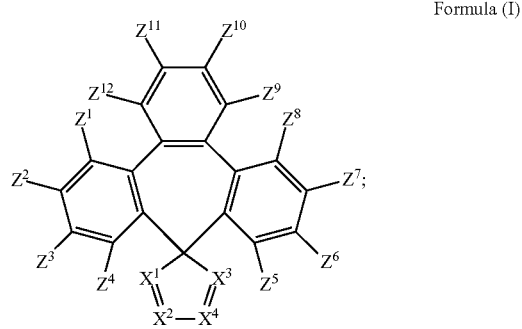

Formula (I)

wherein $X^1$ and $X^2$ are each independently $C(R^a)$, the two $(R^a)$s are the same or different, and the two $(R^a)$s are joined together to form a first aryl ring;
wherein $X^3$ and $X^4$ are each independently $C(R^b)$, the two $(R^b)$s are the same or different, and the two $(R^b)$s are joined to form a second aryl ring, and the second aryl ring is a polycyclic aromatic ring;
wherein $Z^1$ to $Z^{12}$ are each independently selected from the group consisting of: a hydrogen atom, a deuterium atom, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocyeloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms.

2. The compound as claimed in claim 1, wherein the polycyclic aromatic ring is selected from the group consisting of: naphthalene ring, anthracene ring, phenanthrene ring, pyrene ring, 9,9-dimethylfluorene ring, benzophenanthrene ring, benzopyrene ring, fluoranthene ring, triphenylene ring and benzofluoranthene ring.

3. The compound as claimed in claim 1, wherein the compound is represented by any one of the following Formulae (I-I) to (I-XII):

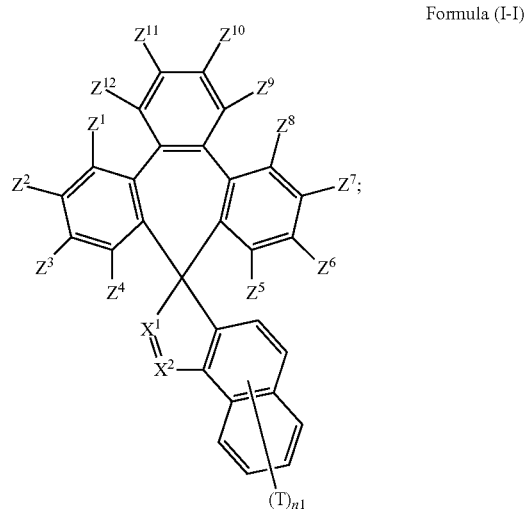

Formula (I-I)

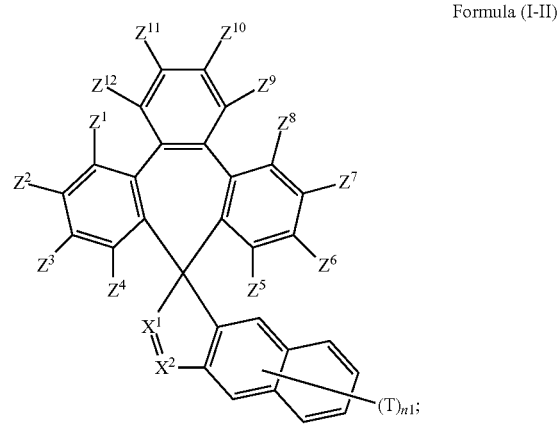

Formula (I-II)

Formula (I-III)
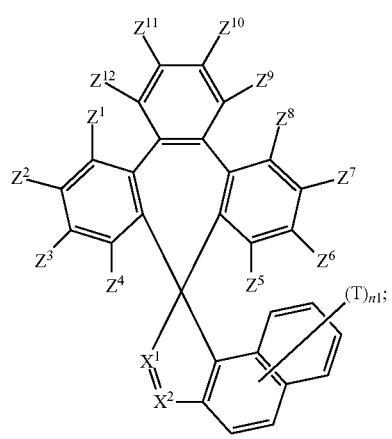
Formula (I-VI)
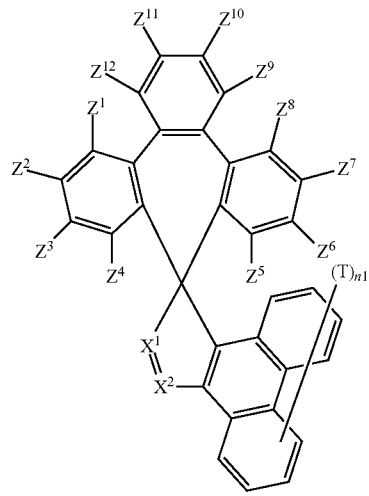
Formula (I-IV)
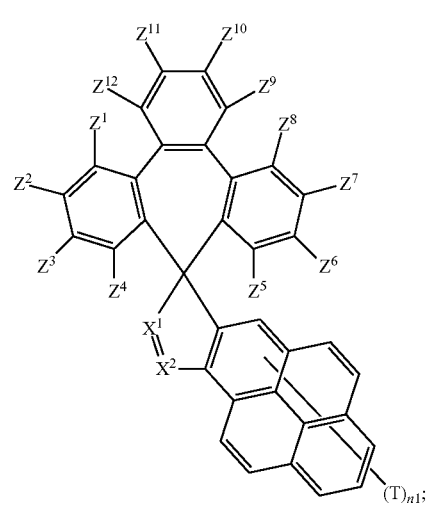
Formula (I-VII)
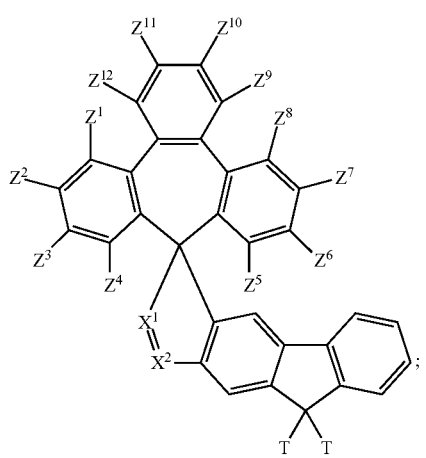
Formula (I-V)
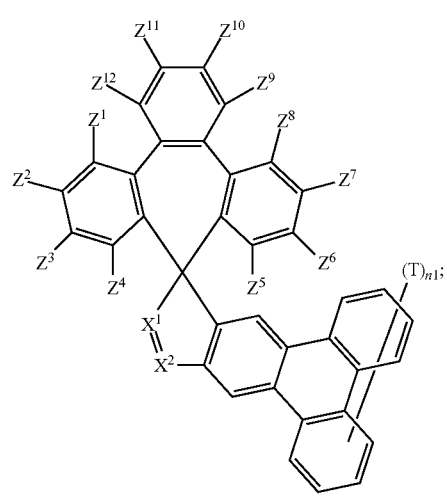
Formula (I-VIII)
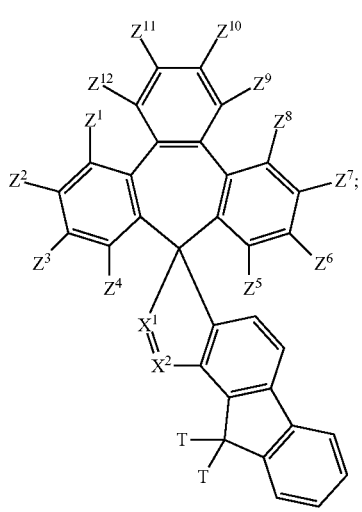

-continued

Formula (I-IX)

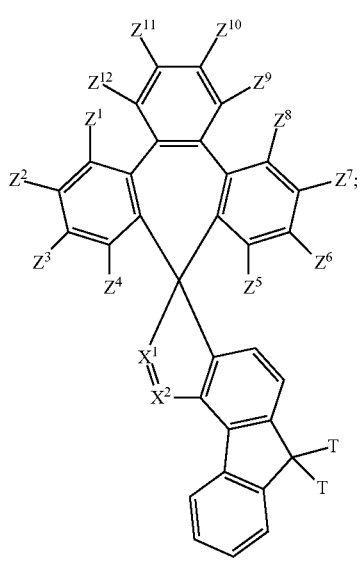

Formula (I-X)

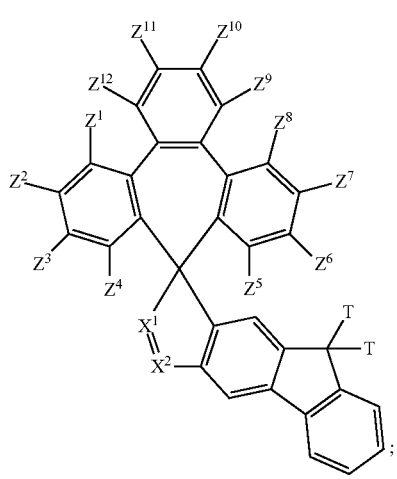

Formula (I-XI)

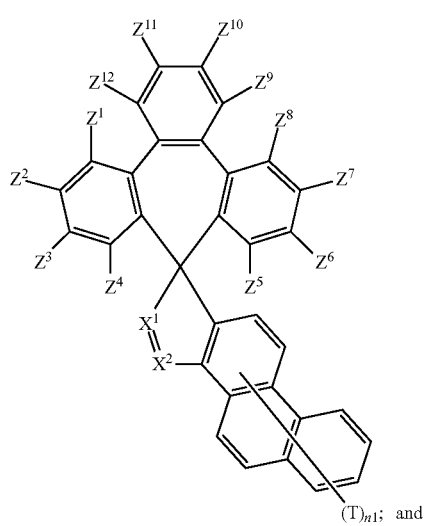

-continued

Formula (I-XII)

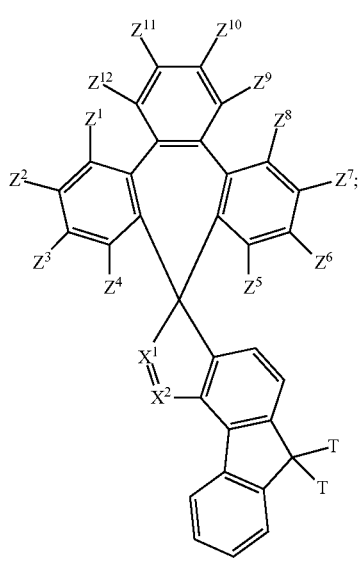

wherein n1 is a positive integral from 0 to 4, and T is selected from the group consisting of: a hydrogen atom, a deuterium atom, a methyl group, an ethyl group, a propyl group, a butyl group, a pentyl group, a hexyl group, and a phenyl group.

4. The compound as claimed in claim 1, wherein the first aryl ring extended from $X^1$ and $X^2$ is a substituted or unsubstituted 6 to 60-membered carbon ring.

5. The compound as claimed in claim 4, wherein the substituted or unsubstituted 6 to 60-membered carbon ring is selected from the group consisting of: a substituted or unsubstituted benzene ring, a substituted or unsubstituted naphthalene ring, a substituted of unsubstituted anthracene ring, a substituted or unsubstituted phenanthrene ring, a substituted or unsubstituted pyrene ring, a substituted or unsubstituted benzopyrene ring, a substituted or unsubstituted fluoranthene ring, a substituted or unsubstituted benzofluoranthene ring, and a substituted or unsubstituted fluorene ring.

6. The compound as claimed in claim 5, wherein the substituted or unsubstituted 6 to 60-membered carbon ring is a substituted or unsubstituted benzene structure.

7. The compound as claimed in claim 1, wherein at least one of $Z^1$ to $Z^8$ in formula (I) is selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms, a phosphine group having 1 to 40 carbon atoms and substituted with at least one functional group, and a phosphine oxide group having 1 to 40 carbon atoms and substituted with at least one functional group, wherein said functional group is selected from the group consisting of: a cyano group, a nitro group, a trifluoromethyl group, a fluor group, and a chloro group.

8. The compound as claimed in claim 1, wherein at least one of $Z^1$ to $Z^8$ in Formula (I) is selected from the group consisting of:

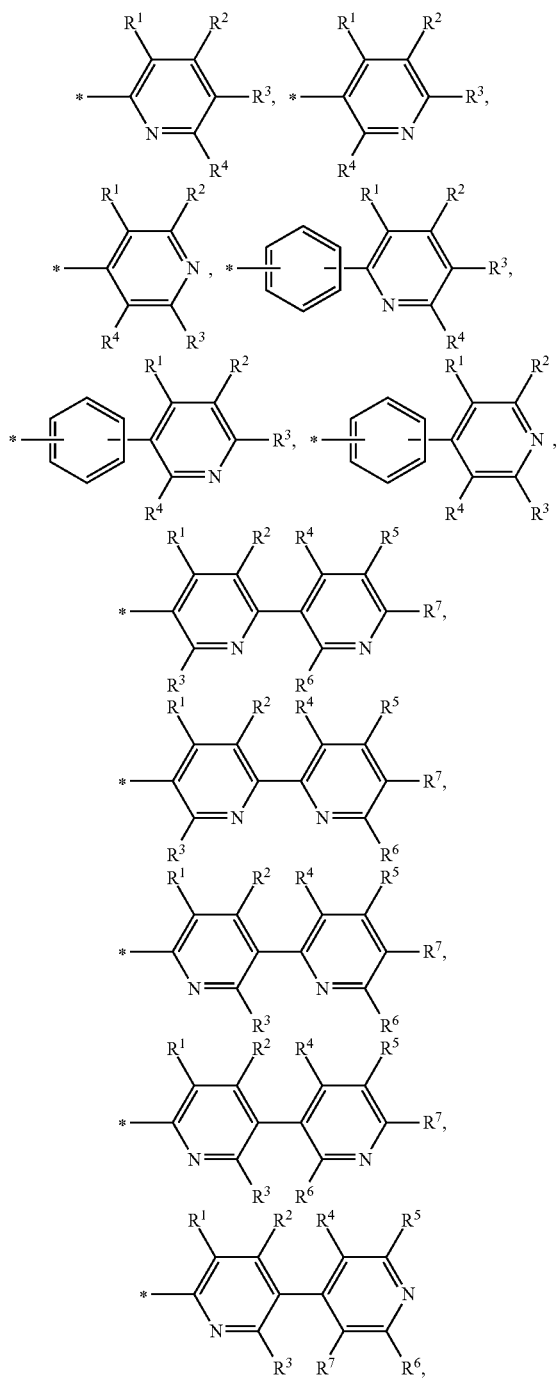

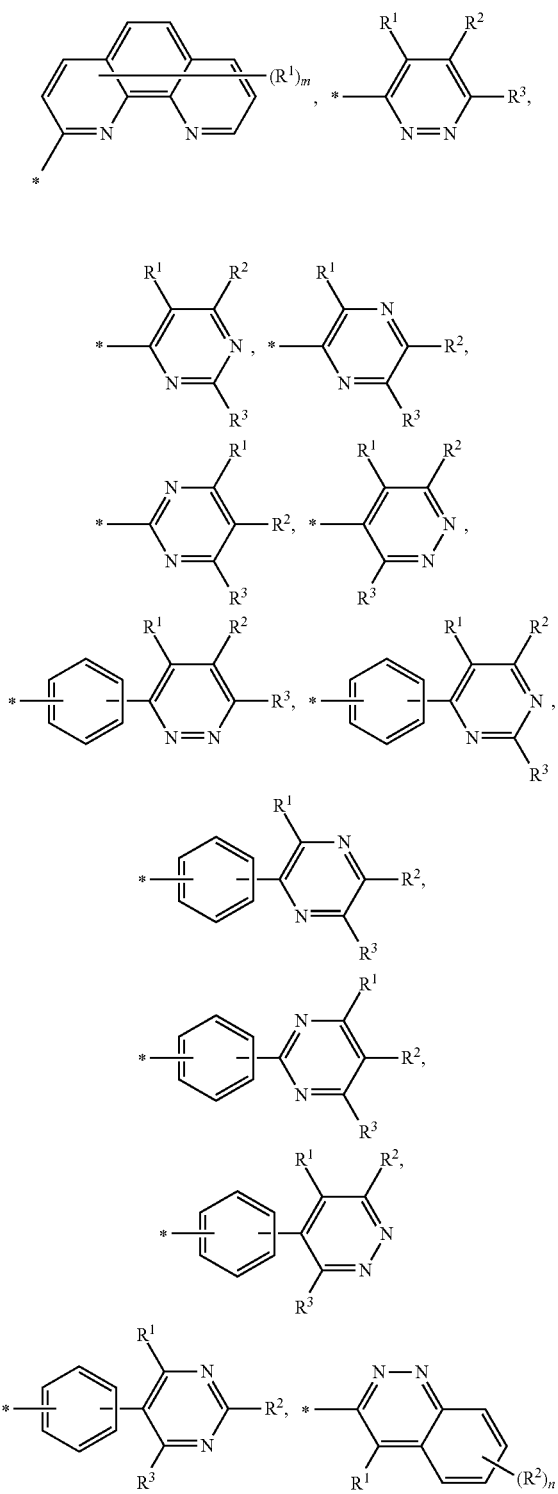

-continued
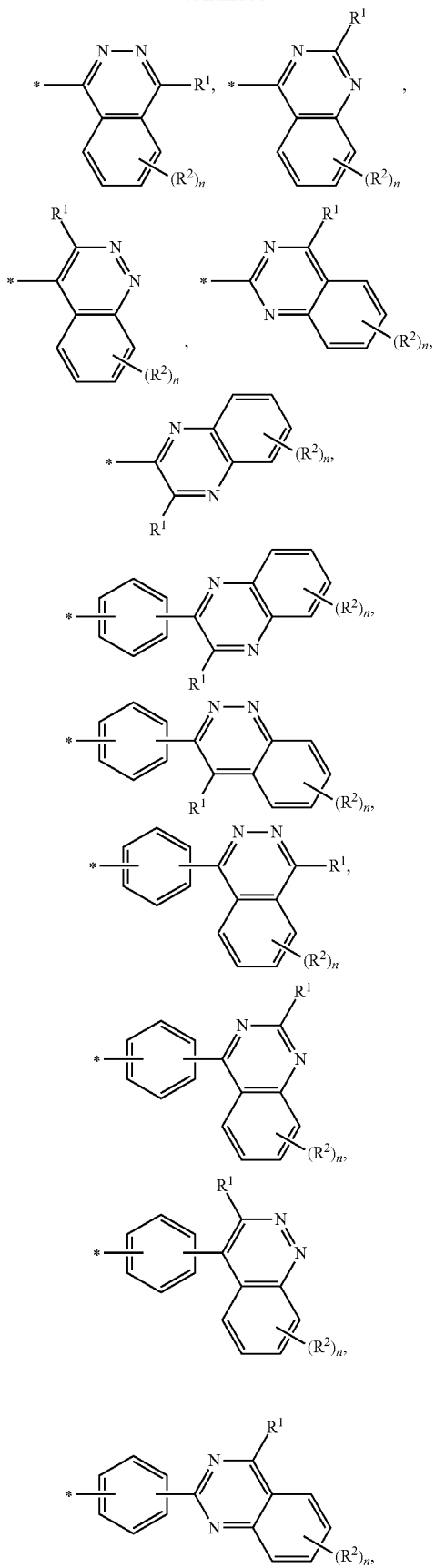
-continued
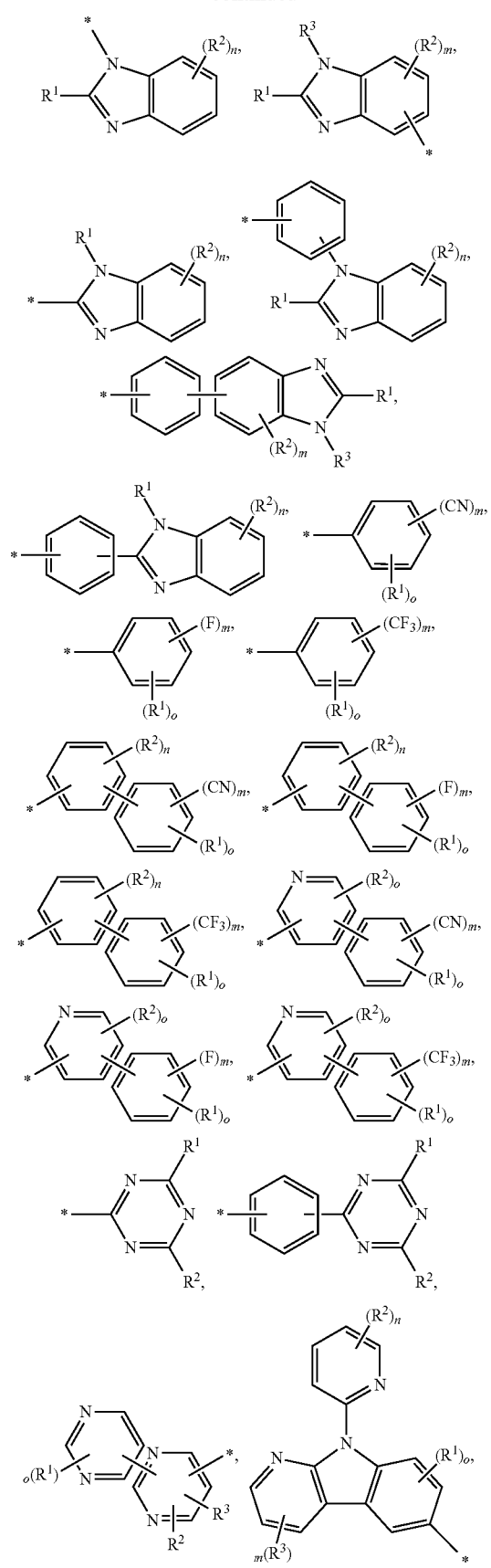

-continued

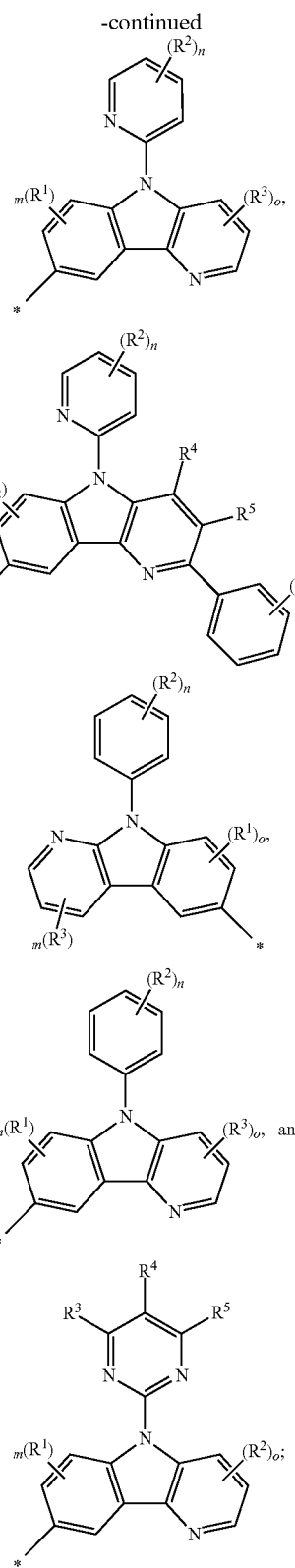

wherein R[1] to R[7] are each independently selected from the group consisting of: a hydrogen atom, a deuterium atom, a halogen group a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

wherein n is a positive integral from 0 to 4, m is a positive integral from 0 to 3, o is a positive integral from 0 to 3, and the total of m and o is not more than 5.

9. The compound as claimed in claim 1, wherein at least one of $Z^1$, $Z^2$, $Z^3$, $Z^6$, $Z^7$, and $Z^8$ in Formula (I) is selected from the group consisting of:

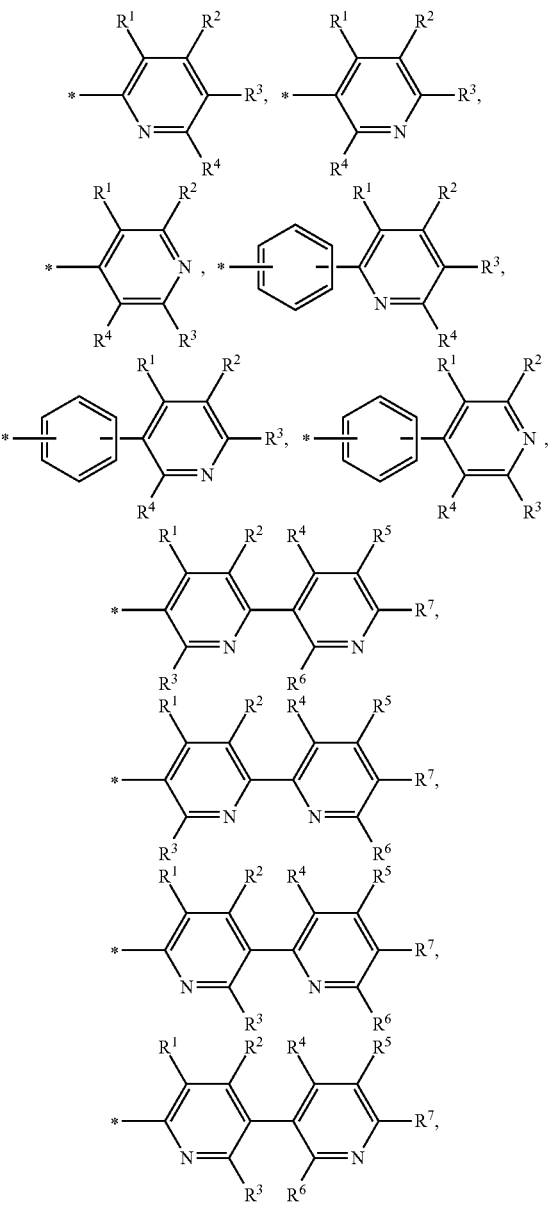

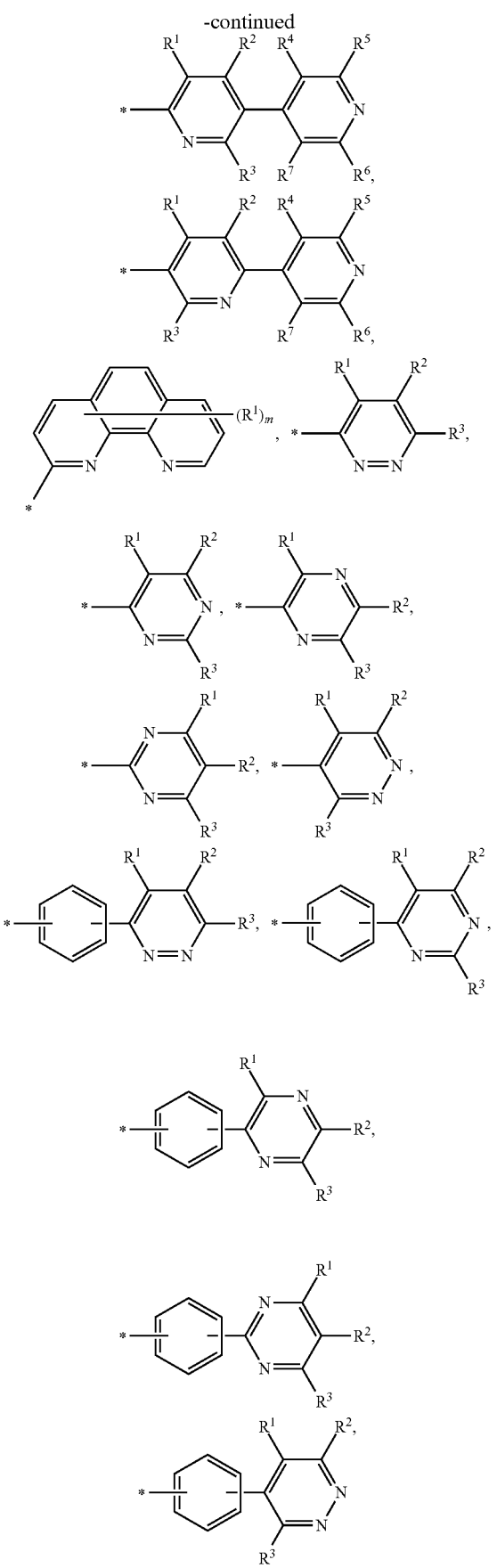
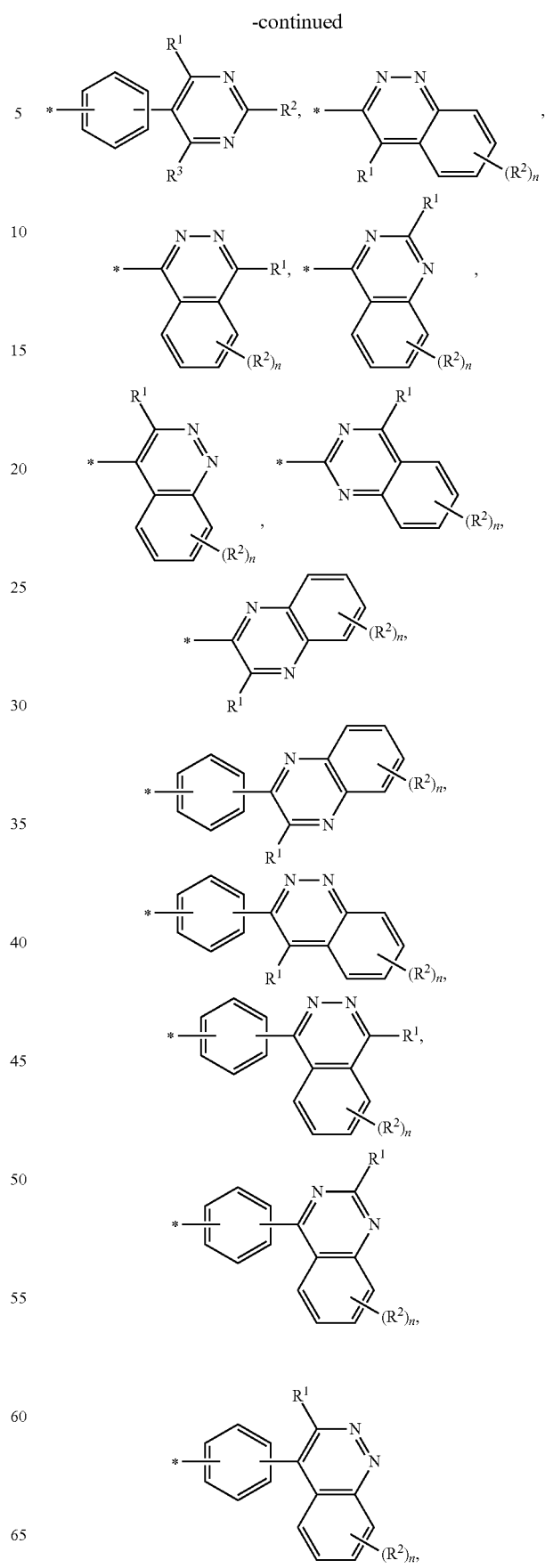

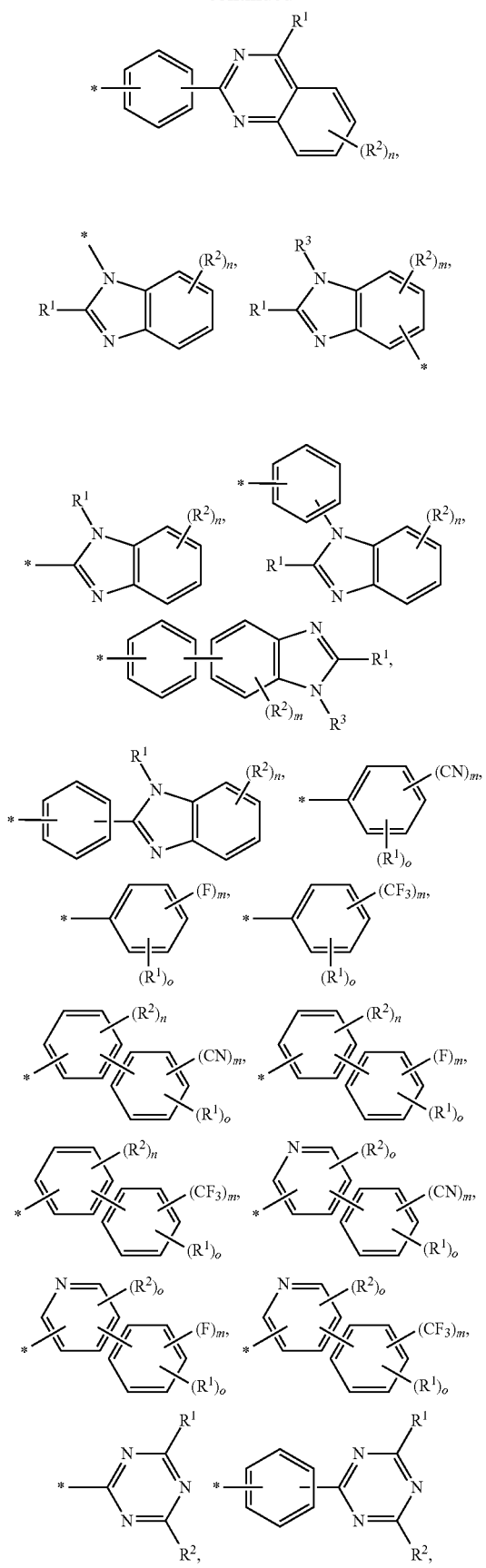
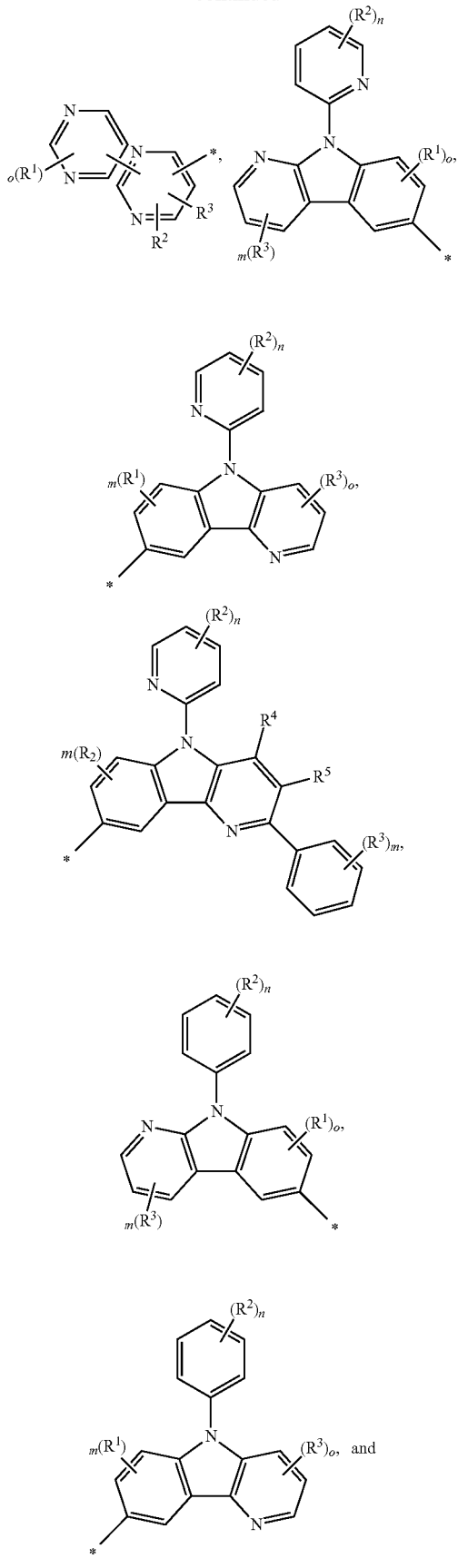

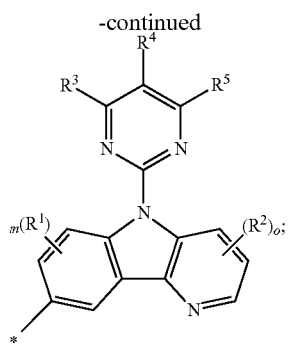

wherein $R^1$ to $R^7$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

wherein n is a positive integral from 0 to 4, m is a positive integral from 0 to 3, o is a positive integral from 0 to 3, and the total of m and o is not more than 5;

wherein $Z^4$ and $Z^5$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

10. The compound as claimed in claim 1, wherein at least one of $Z^2$, $Z^3$, $Z^6$, and $Z^7$ in Formula (I) is selected from the group consisting of:

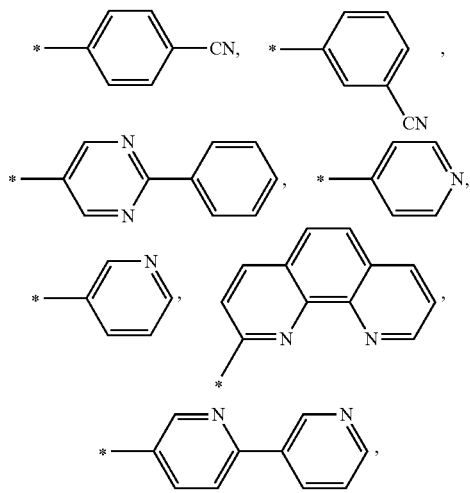

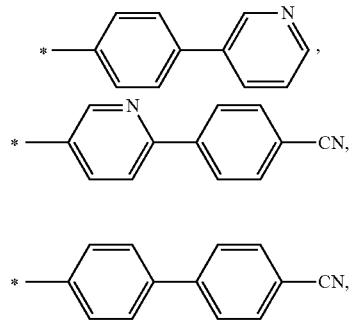

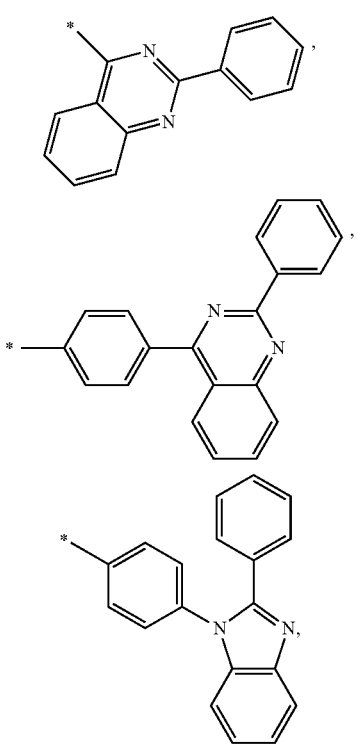

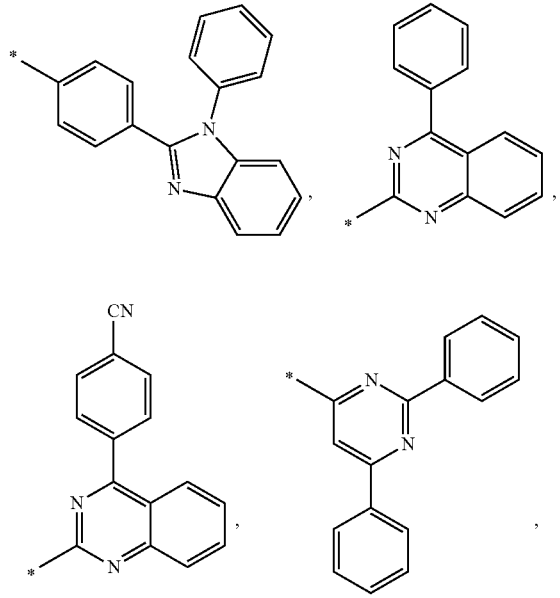

133
-continued
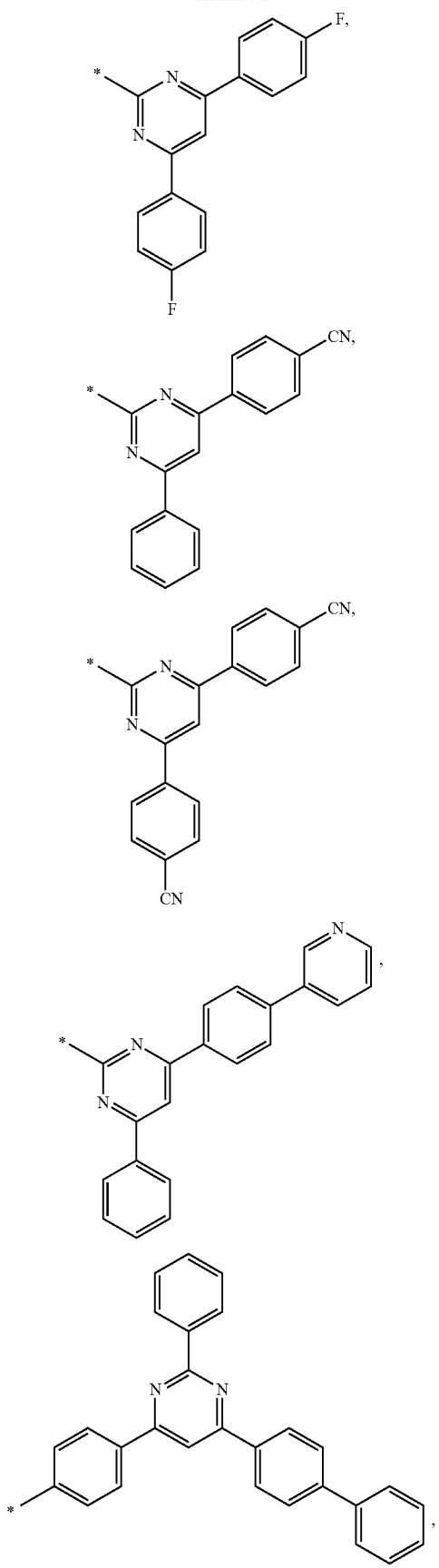
134
-continued
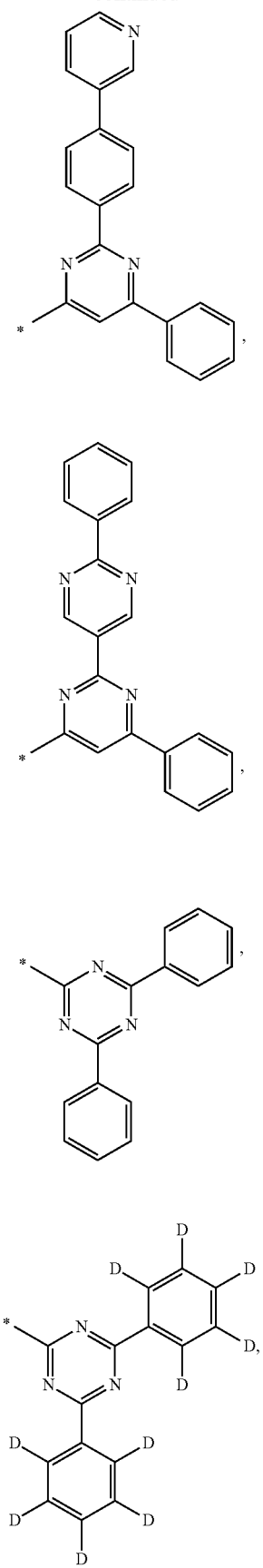

-continued

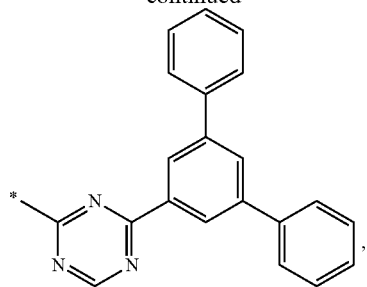

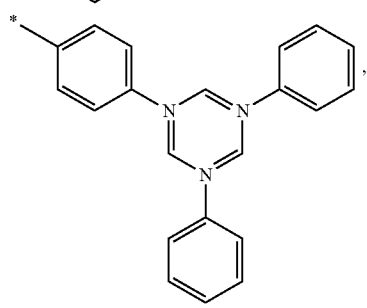

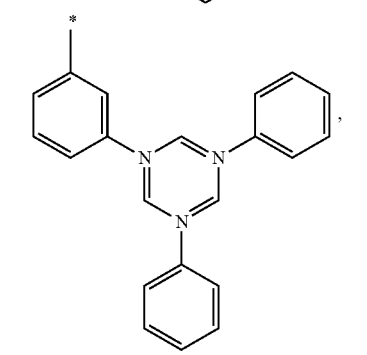

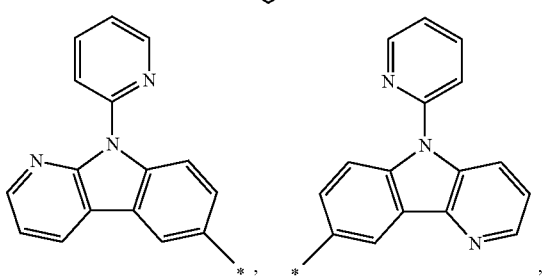

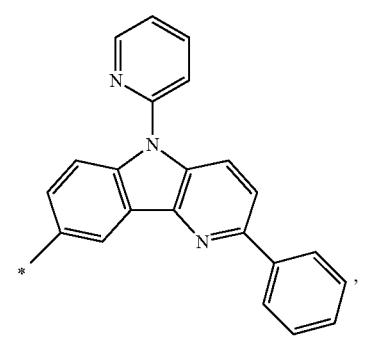

-continued

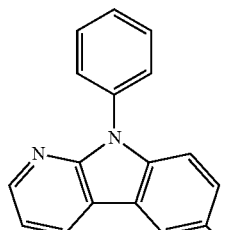

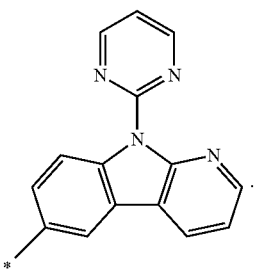

11. The compound as claimed in claim 1, wherein at least one of $Z^1$, $Z^2$, $Z^3$, $Z^6$, $Z^7$, and $Z^8$ in Formula (I) is a substituted triazine group with two phenyl groups, two pyridine groups, two pyrimidine groups, two pyrazine groups, two pyridazine groups, two phenylpyridine groups, two phenylpyrimidine groups, two phenylpyrazine groups, or two phenylpyridazine groups.

12. The compound as claimed in claim 1, wherein $Z^9$ to $Z^{12}$ in Formula (I) are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

13. The compound as claimed in claim 1, wherein the compound is selected from the group consisting of:

Compound I

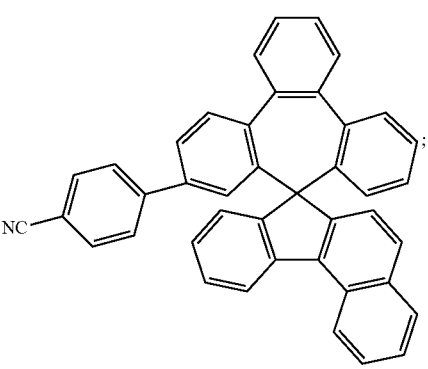

Compound II
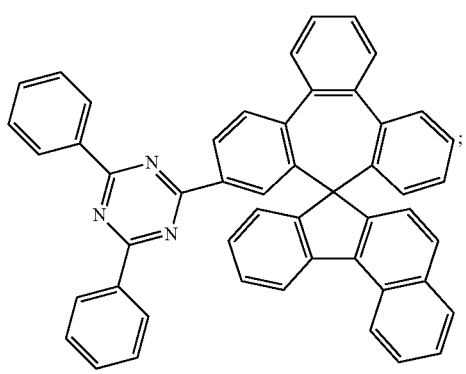
Compound III
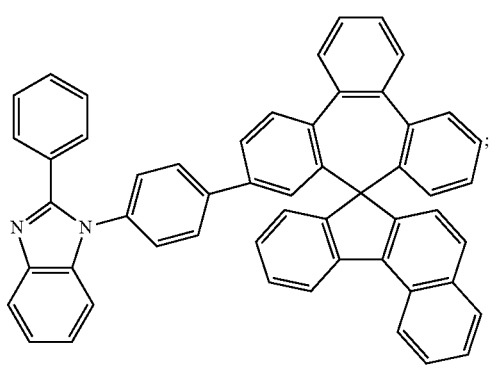
Compound IV
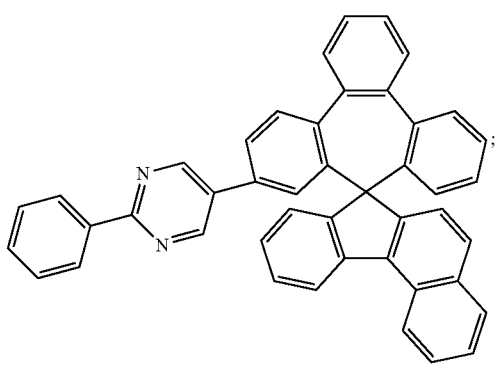
Compound V
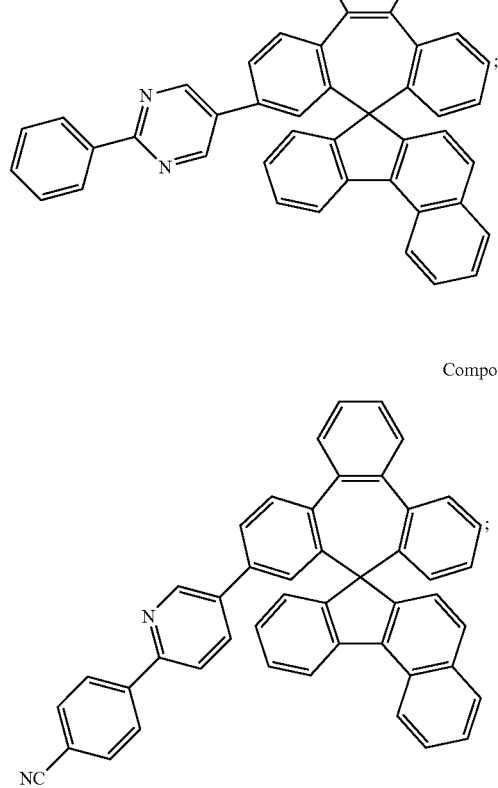
Compound VI
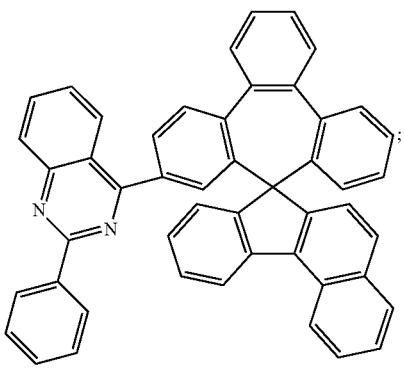
Compound VII
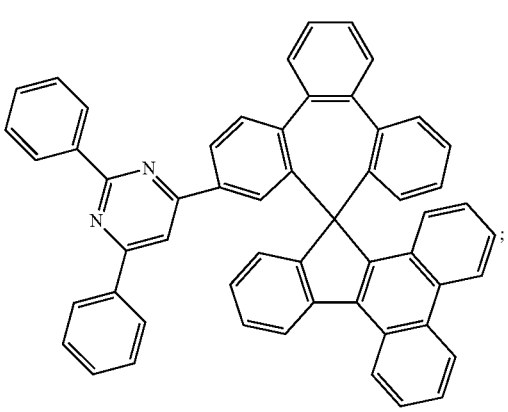
Compound VIII
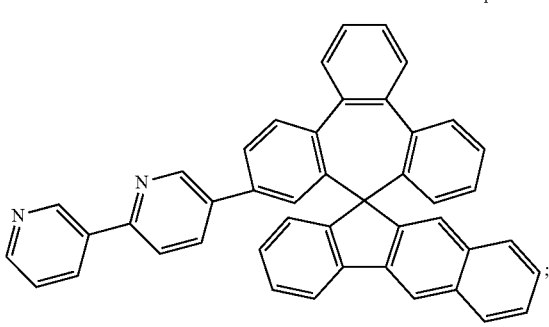
Compound IX
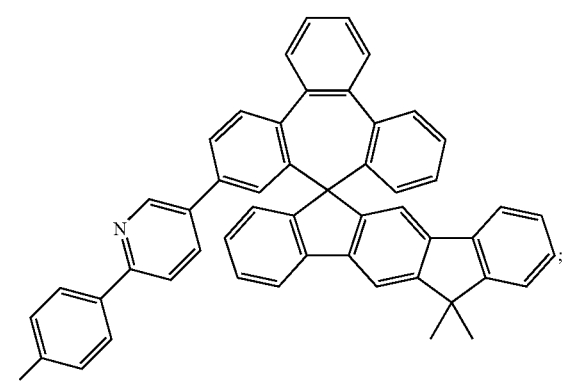

-continued

Compound X

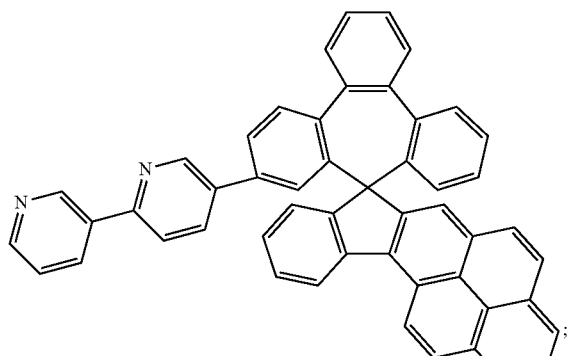

Compound XI

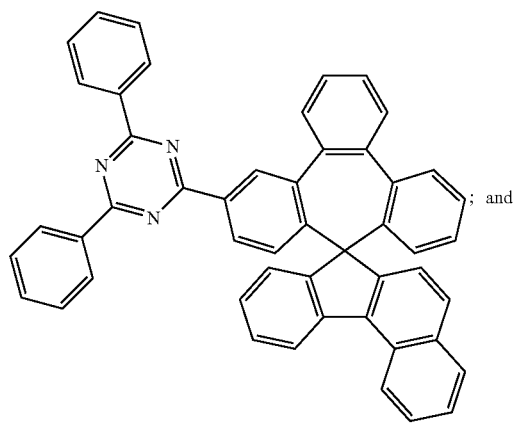

Compound XII

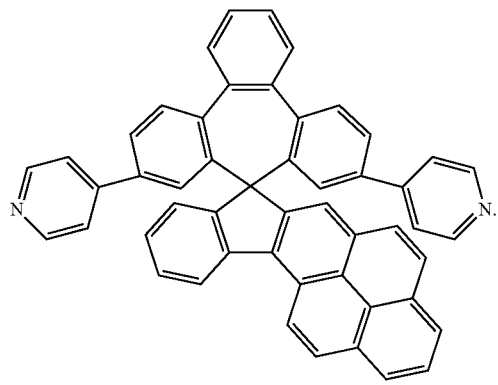

14. An organic electronic device, comprising a first electrode, a second electrode, and an organic layer disposed between the first electrode and the second electrode, wherein the organic layer comprises the compound as claimed in claim 1.

15. The organic electronic device as claimed in claim 14, wherein the organic electronic device is an organic light emitting device.

16. The organic electronic device as claimed in claim 15, wherein the organic light emitting device comprises:
 a hole injection layer formed on the first electrode;
 a hole transport layer formed on the hole injection layer;
 an emission layer formed on the hole transport layer;
 an electron transport layer formed on the emission layer, wherein the organic layer is the electron transport layer; and
 an electron injection layer formed between the electron transport layer and the second electrode.

17. The organic electronic device as claimed in claim 15, wherein the organic light emitting device comprises:
 a hole injection layer formed on the first electrode;
 a hole transport layer formed on the hole injection layer;
 an emission layer formed on the hole transport layer;
 a hole blocking layer formed on the emission layer, wherein the organic layer is the bole blocking layer;
 an electron transport layer formed on the hole blocking layer; and
 an electron injection layer formed between the electron transport layer and the second electrode.

18. The organic electronic device as claimed in claim 14, wherein the compound is selected from the group consisting of:

Compound I

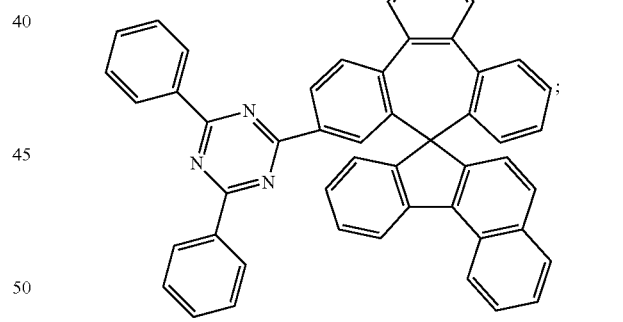

Compound II

Compound III

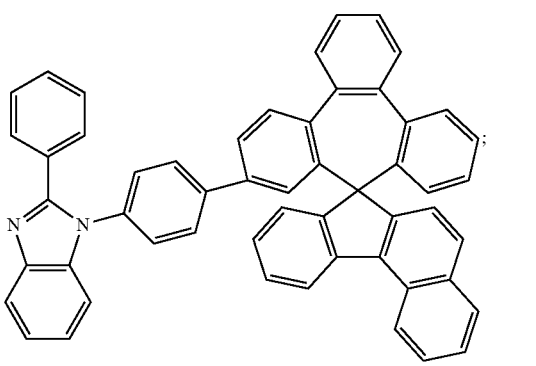

Compound IV
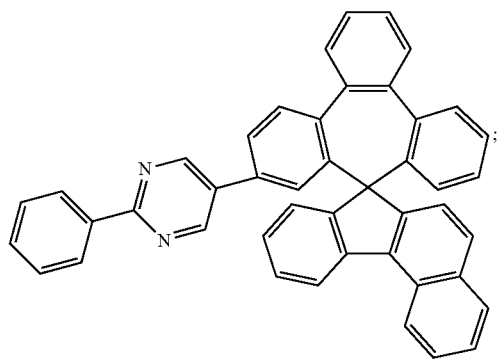
Compound V
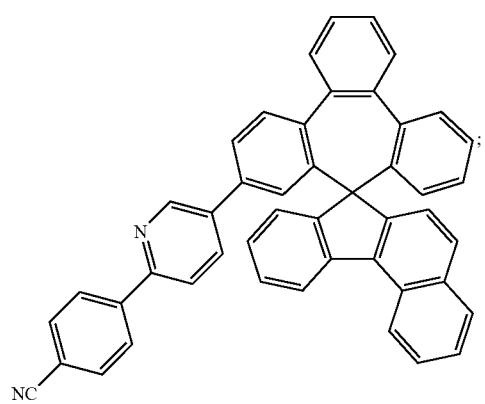
Compound VI
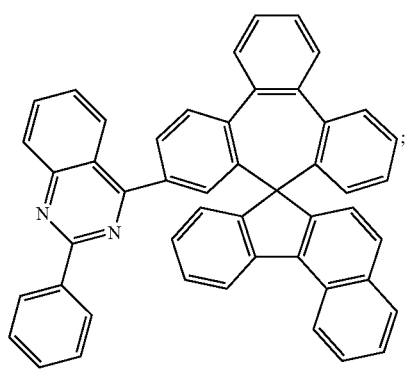
Compound VII
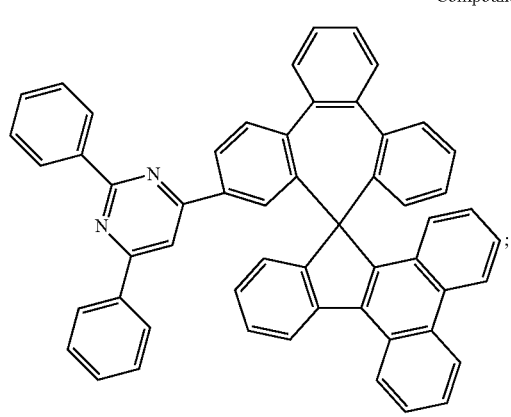
Compound VIII
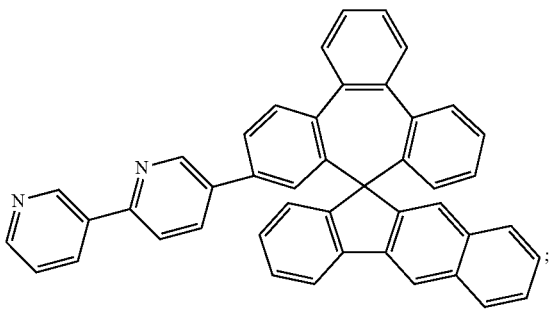
Compound IX
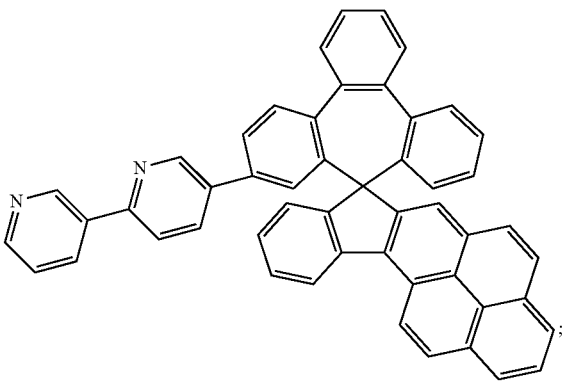
Compound X
(image continues)
Compound XI
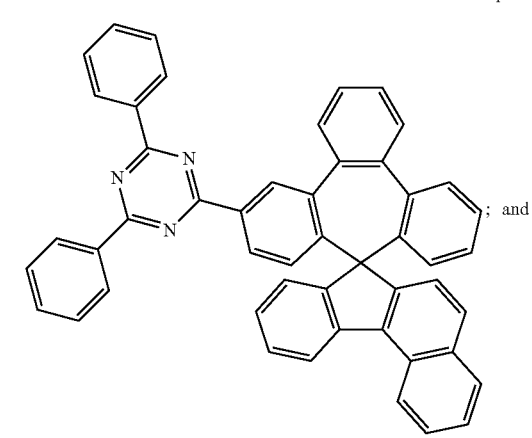
; and -continued
Compound XII
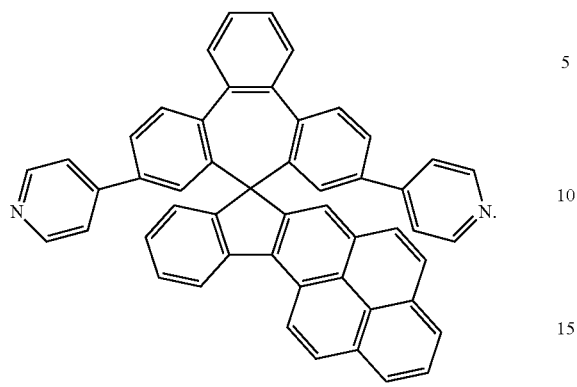
* * * * *